United States Patent
Espling et al.

(10) Patent No.: US 7,846,434 B2
(45) Date of Patent: Dec. 7, 2010

(54) MATERIALS AND METHODS FOR IMPROVED IMMUNOGLYCOPROTEINS

(75) Inventors: Erik Stephen Espling, Seattle, WA (US); Peter Armstrong Thompson, Bellevue, WA (US); Peter Robert Baum, Seattle, WA (US)

(73) Assignee: Trubion Pharmaceuticals, Inc., Seattle, WA (US)

( * ) Notice: Subject to any disclaimer, the term of this patent is extended or adjusted under 35 U.S.C. 154(b) by 0 days.

(21) Appl. No.: 12/082,497

(22) Filed: Apr. 11, 2008

(65) Prior Publication Data

US 2009/0041765 A1 Feb. 12, 2009

Related U.S. Application Data

(63) Continuation-in-part of application No. PCT/US2007/082343, filed on Oct. 24, 2007.

(60) Provisional application No. 60/853,944, filed on Oct. 24, 2006.

(51) Int. Cl.
*A61K 39/395* (2006.01)

(52) U.S. Cl. .................. 424/130.1; 530/387.1

(58) Field of Classification Search ........ None
See application file for complete search history.

(56) References Cited

U.S. PATENT DOCUMENTS

| | | | |
|---|---|---|---|
| 5,605,690 A | 2/1997 | Jacobs et al. | |
| 5,914,111 A | 6/1999 | Wallner et al. | |
| 6,737,056 B1 | 5/2004 | Presta | |
| 2002/0199213 A1 | 12/2002 | Tomizuka et al. | |
| 2003/0031667 A1 | 2/2003 | Deo et al. | |
| 2003/0118592 A1 | 6/2003 | Ledbetter et al. | |
| 2003/0133939 A1 | 7/2003 | Ledbetter et al. | |
| 2003/0194404 A1 | 10/2003 | Greenfeder et al. | |
| 2004/0053366 A1* | 3/2004 | Lo et al. ............ | 435/69.1 |
| 2005/0037421 A1 | 2/2005 | Honda et al. | |
| 2005/0095700 A1 | 5/2005 | Budzowski et al. | |
| 2005/0136049 A1 | 6/2005 | Ledbetter et al. | |
| 2006/0127404 A1 | 6/2006 | Huang et al. | |
| 2007/0020260 A1 | 1/2007 | Presta | |
| 2007/0059306 A1* | 3/2007 | Grosmaire et al. ........ | 424/144.1 |

FOREIGN PATENT DOCUMENTS

| | | |
|---|---|---|
| EP | 404097 | 12/1990 |
| WO | WO-91/10741 | 7/1991 |
| WO | WO-92/01047 | 1/1992 |
| WO | WO-93/11161 | 6/1993 |
| WO | WO-96/34096 | 10/1996 |
| WO | WO-98/24893 | 6/1998 |
| WO | WO-91/17271 | 11/1999 |
| WO | WO-2004/002424 | 1/2004 |
| WO | WO-2005/081687 | 9/2005 |
| WO | WO 2007/028144 * | 3/2007 |
| WO | WO-2007/048122 | 4/2007 |
| WO | WO 2007014278 * | 5/2007 |
| WO | WO-2007/146968 | 6/2007 |
| WO | WO 2007/121354 * | 10/2007 |

OTHER PUBLICATIONS

Biocca et al., Expression and targeting of intracellular antibodies in mammalian cells, *EMBO J.*, 9: 101-8 (1990).
Bird et al., Single-chain antigen-binding proteins, *Science* 242: 423-6 (1988).
Bruggemann et al., Designer mice: the production of human antibody repertoires in transgenic animals., *Year in Immuno.*, 7:33-40 (1993).
Castanospermine from Castanospermum australe seeds. http://www.sigmaaldrich.com/sigma/product%20information%20sheet/c3784pis.pdf (2005).
Caton et al., Influenza virus hemagglutinin-specific antibodies isolated from a combinatorial expression library are closely related to the immune response of the donor, *Proc. Natl. Acad. Sci.* 87:6450-4 (1990).
Chang et al., Targeted gene therapy with CD40Ig to induce long-term acceptance of liver allografts, *Surgery*, 132: 149-56 (2002).
Chothia et al., Canonical structures for the hypervariable regions of immunoglobulins, *J. Mol. Bio.* 196: 901-917 (1987).
Co at el., A humanized antibody specific for the platelet integrin gpIIb/IIIa, *J. Immunol.* 152:2968-76 (1994).
Colby et al., Potent inhibition of huntingtin aggregation and cytotoxicity by a disulfide bond-free single-domain intracellular antibody, *Proc. Natl. Acad. Sci.* 101:17616-21 (2004).
Cortez-Retamozo et al., Efficient cancer therapy with a nanobody-based conjugate., *Cancer Research*, 64:2853-57 (2004).
Desmyter et al., Antigen specificity and high affinity binding provided by one single loop of a camel single-domain antibody, *J. Biol. Chem.* 276: 26285-90 (2001).
Elbein et al., Glycosidase inhibitors: Inhibitors of N-linked oligosaccharide processing. *FASEB J.* 5: 3055-63 (1991).
Ewert et al., Biophysical properties of camelid V(HH) domains compared to those of human V(H)3 domains, *Biochemistry*, 41:3628-36 (2002).
Ferrara et al., Modulation of therapeutic antibody effector functions by glycosylation engineering: influence of Golgi enzyme localization domain and co-expression of heterologous beta1, 4-N-acetylglucosaminyltransferase III and Golgi alpha-mannosidase II, *Biotechnol Bioeng.*, 93: 851-861 (2006).
Genbank Accession No. BC031992, *Homo sapiens* Fc fragment of IgG, low affinity IIb, receptor (CD32), 2006.
Genbank Accession No. BC032634, *Homo sapiens* Fc fragment of IgG, high affinity Ia, receptor (CD64), 2006.
Genbank Accession No. NM021642, *Homo sapiens* Fc fragment of IgG, low affinity IIa, receptor (CD32)(FCGR2A), 2008.
Genbank Accession No. X07934, Human mRNA for Fc gamma receptor (FcRIII, CD16, FcR-lo), 2004.

(Continued)

*Primary Examiner*—Michail A Belyavskyi
(74) *Attorney, Agent, or Firm*—Janet Sleath; Speckman Law Group PLLC

(57) ABSTRACT

Immunoglycoproteins, including antibodies, with improved ADCC and altered glycosylation patterns are provided. Also provided are cell culturing methods and media for producing such immunoglycoproteins, and therapeutic uses of such immunoglycoproteins.

17 Claims, 28 Drawing Sheets

OTHER PUBLICATIONS

Gruber et al., Efficient tumor cell lysis mediated by a bispecific single chain antibody expressed in *Escherichia coli*, *J. Immunol.* 152: 5368 (1994).

Hashim et al., Role of processing of N-linked oligosaccharides in control of immunoglobulin secretion from rat hybridomas. *Mol. Immunol.* 24: 1087-96 (1987).

Hodoniczky et al., Control of recombinant monoclonal antibody effector functions by Fc N-glycan remodeling in vitro, *Biotechnol. Prog.*, 21: 1644-1652 (2005).

Hollinger et al., "Diabodies": small bivalent and bispecific antibody fragments, *Proc. Natl. Acad. Sci.* 90: 6444-8 (1993).

Hu et al., Targeting tissue factor on tumor vascular endothelial cells and tumor cells for immunotherapy in mouse models of prostatic cancer, *Proc. Natl. Acad. Sci.* 98, 12180-5 (2001).

Huston et al., Protein engineering of antibody binding sites: recovery of specific activity in an anti-digoxin single-chain Fv analogue produced in *Escherichia coli*, *Proc. Natl. Acad. Sci.* 85:5879-83 (1988).

Jakobovits et al., Analysis of homozygous mutant chimeric mice: deletion of the immunoglobulin heavy-chain joining region blocks B-cell development and antibody production, *Proc. Natl. Acad. Sci.* 90:2551 (1993).

Jakobovits et al., Germ-line transmission and expression of a human-derived yeast artificial chromosome, *Nature*, 362:255-8 (1993).

Jones et al., Replacing the complementarity-determining regions in a human antibody with those from a mouse, *Nature*, 321:522-525 (1986).

Kanda et al., Comparison of biological activity among nonfucosylated therapeutic IgG1 antibodies with three different N-linked Fc oligosaccharides: the high-mannose, hybrid, and complex types. *Glycobiology.* 17: 104-18 (2006).

Kettleborough, et al., Humanization of a mouse monoclonal antibody by CDR-grafting: the importance of framework residues on loop conformation, *Protein Eng.* 4:773-83 (1991).

Kim et al., Targeting the IL-15 receptor with an antagonist IL-15 mutant/Fc gamma2a protein blocks delayed-type hypersensitivity, *J. Immunol.* 160, 5742-8 (1998).

Landolfi, A chimeric IL-2/Ig molecule possesses the functional activity of both proteins, *J. Immunol.* 146, 915-9 (1991).

Morrison et al., Chimeric human antibody molecules: mouse antigen-binding domains with human constant region domains, *Proc. Natl. Acad. Sci.*, 81: 6851-55 (1984).

Morrison et al., Genetically engineered antibody molecules, *Adv. Immunol.*, 44: 65-92 (1988).

Neri et al., Basal cell and basosquamous carcinomas of the external ear. Immunohistochemical study, *J. Mol. Biol.*, 246: 367-73 (1995).

Olafsen et al., Characterization of engineered anti-p185HER-2 (scFv-CH3)2 antibody fragments (minibodies) for tumor targeting, *Protein Eng. Des Sel.* 17: 315-23 (2004).

Padlan, A possible procedure for reducing the immunogenicity of antibody variable domains while preserving their ligand-binding properties, *Molec. Immun.* 28:489-98 (1991).

Padlan, Anatomy of the antibody molecule, *Molec. Immun.* 31:169-217 (1994).

Rosnet et al., Expression and signal transduction of the FLT3 tyrosine kinase receptor, *Acta. Haemato.*, 95:218-23, (1996).

Rothman et al., Antibody-dependent cytotoxicity mediated by natural killer calls is enhanced by castanospermine-induced alterations of IgG glycosylation. *Mol. Immunol.* 26:1113-23 (1989).

Sayegh et al., CD28-B7 blockade after alloantigenic challenge in vivo inhibits Th1 cytokines but spares Th2, *J. Exp. Med.*, 181, 1869-74 (1995).

Sburlati et al., Synthesis of bisected glycoforms of recombinant IFN-beta by overexpression of beta-1,4-N-acetylglucosaminyltransferase III in Chinese hamster ovary cells, *Biotechnol. Prog.*, 14: 189-192 (1998).

Scatchard et al., *Ann N.Y. Acad. Sci.*, 51:660 (1949).

Schoonjans et al., Fab chains as an efficient heterodimerization scaffold for the production of recombinant bispecific and trispecific antibody derivatives, *J. Immunol.*, 165: 7050-57 (2000).

Shields et al., Lack of Fucose on Human IgG1 N-Linked Oligosaccharide Improves Binding to Human FcγRIII and Antibody-dependent Cellular Toxicity, *J. Biol. Chem.* 277: 26733-26740 (2002).

Shinkawa et al., The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity, *J. Biol. Chem.* 278: 3466-3473 (2003).

Studnicka et al., Human-engineered monoclonal antibodies retain full specific binding activity by preserving non-CDR complementarity-modulating residues, *Protein Eng.*, 7:805-14 (1994).

Taylor et at., In vitro and in vivo activities of OX40 (CD134)-IgG fusion protein isoforms with different levels of immune-effector functions, *J. Leu. Biol.*, 72,522-9 (2002).

Umana et al., Engineered glycoforms of an antineuroblastoma IgG1 with optimized antibody-dependent cellular cytotoxic activity, *Nat Biotechnol.* 17:176-180 (1999).

Verhoeyen et al., Reshaping human antibodies: grafting an antilysozyme activity, *Science*, 239:1534-6 (1988).

Ward et al., Binding activities of a repertoire of single immunoglobulin variable domains secreted from *Escherichia coli*, *Nature*, 341: 544-6 (1989).

Willems et al., Optimizing expression and purification from cell culture medium of trispecific recombinant antibody derivatives, *J. Chromatogr. B Analyt Technol Biomed Life Sci.*, 786: 161-76 (2003).

Zapata et al., Engineering linear F(ab')2 fragments for efficient production in *Escherichia coli* and enhanced antiproliferative activity, *Protein Eng.*, 8:1057-62 (1995).

Zheng et al., Administration of noncytolytic IL-10/Fc in murine models of lipopolysaccharide-induced septic shock and allogeneic islet transplantation, *J. Immunol.*,154, 5590-600 (1995).

Combined International Search Report and Written Opinion of the International Searching Authority, PCT/US2007/082343, dated Apr. 14, 2008.

Kuster, Bernhard et al., "Sequencing of N-Linked Oligosaccharides Directly from Protein Gels: In-Gel Deglycosylation followed by Matrix-Assisted Laser Desorption/Ionization Mass Spectrometry and Normal-Phase High-Performance Liquid Chromatography," Analytical Biochemistry, vol. 250, pp. 82-101 (Jan. 31, 1997).

* cited by examiner

ADCC Activity of v1 015 expressed in the presence of increasing Castanospermine (CS). High affinity V/V 158 FcγR III donor Effect of Castanospermine on TRU-016 Production in Shake Flasks

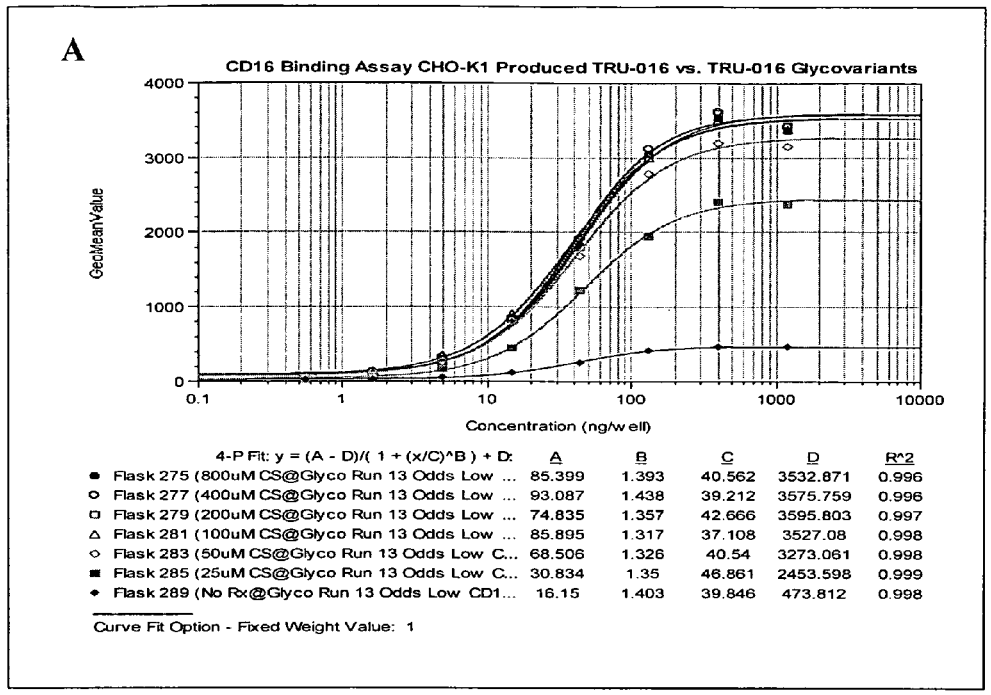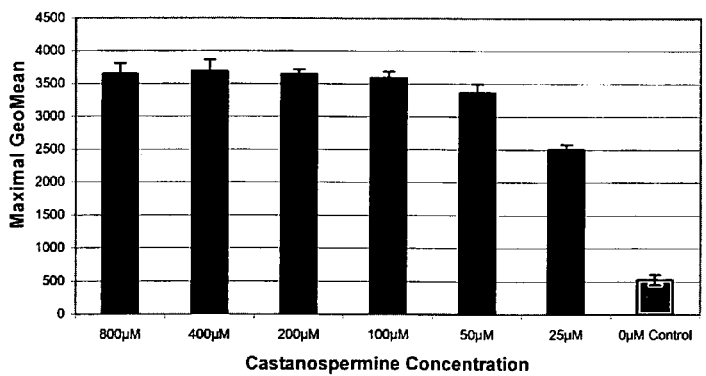
Figure 21

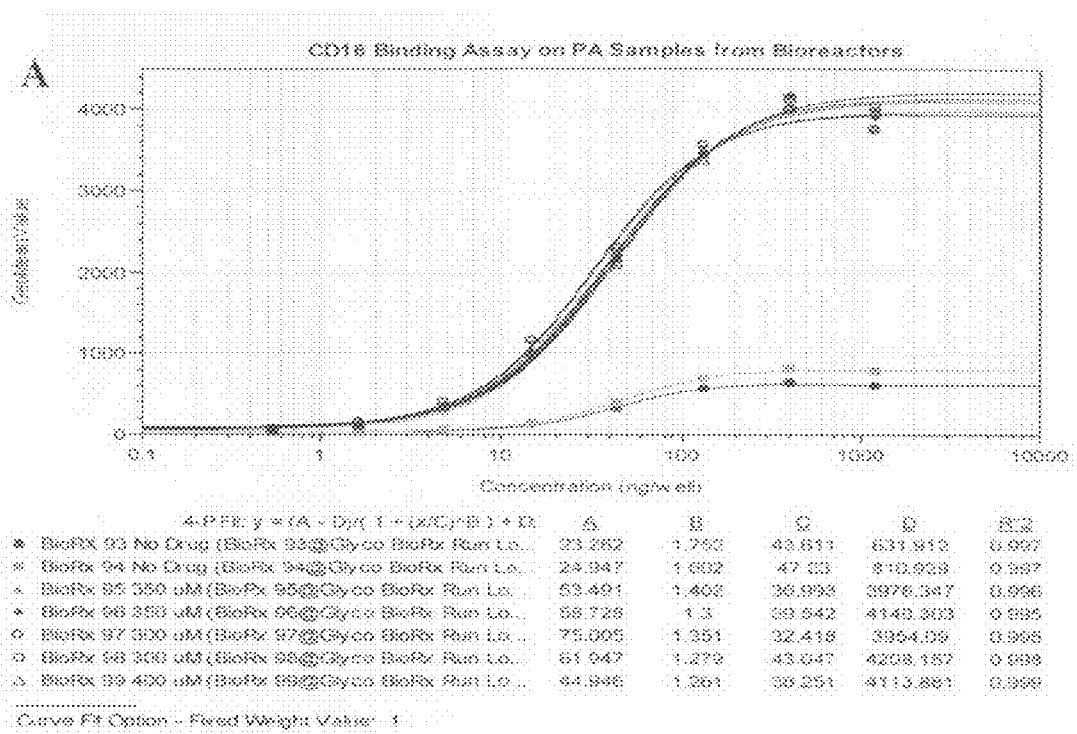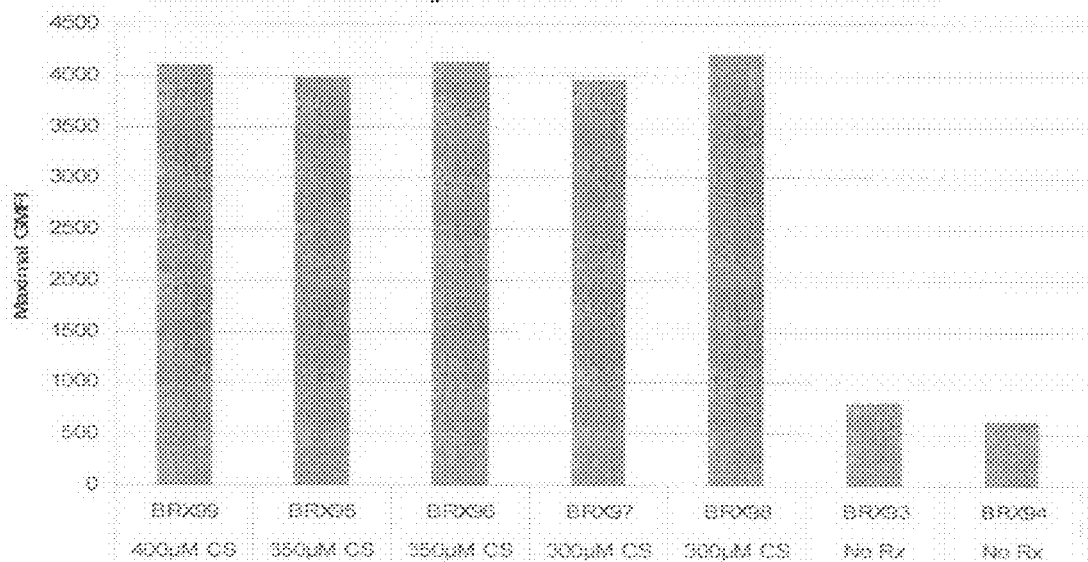
Figure 24

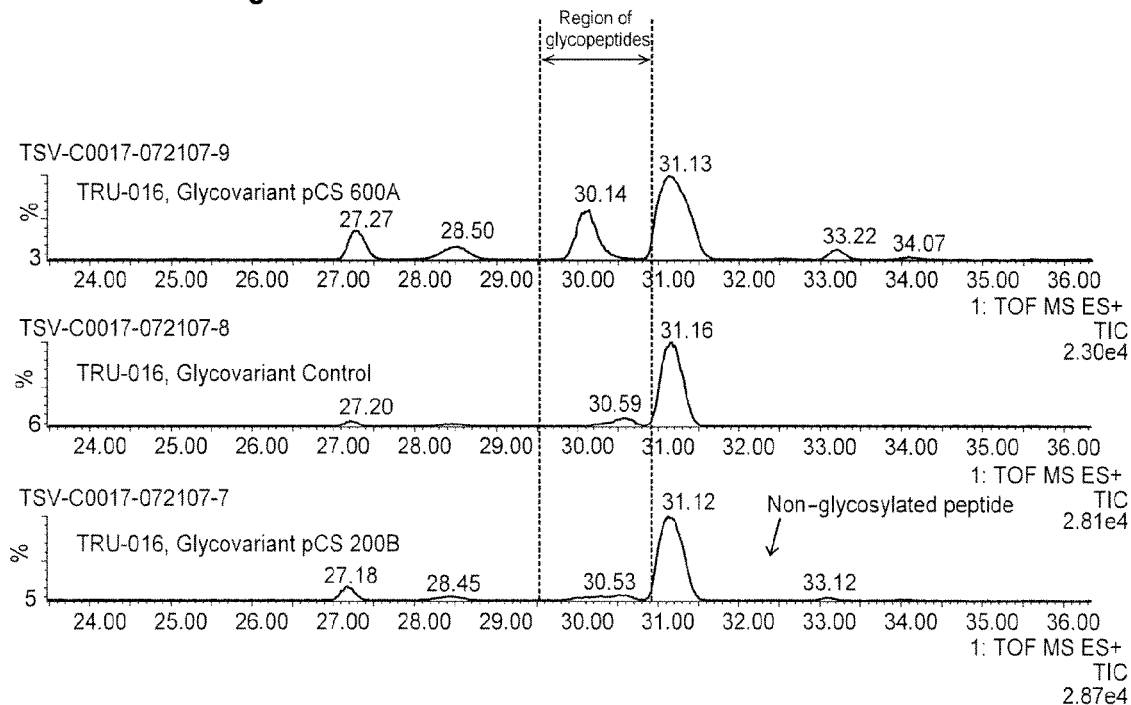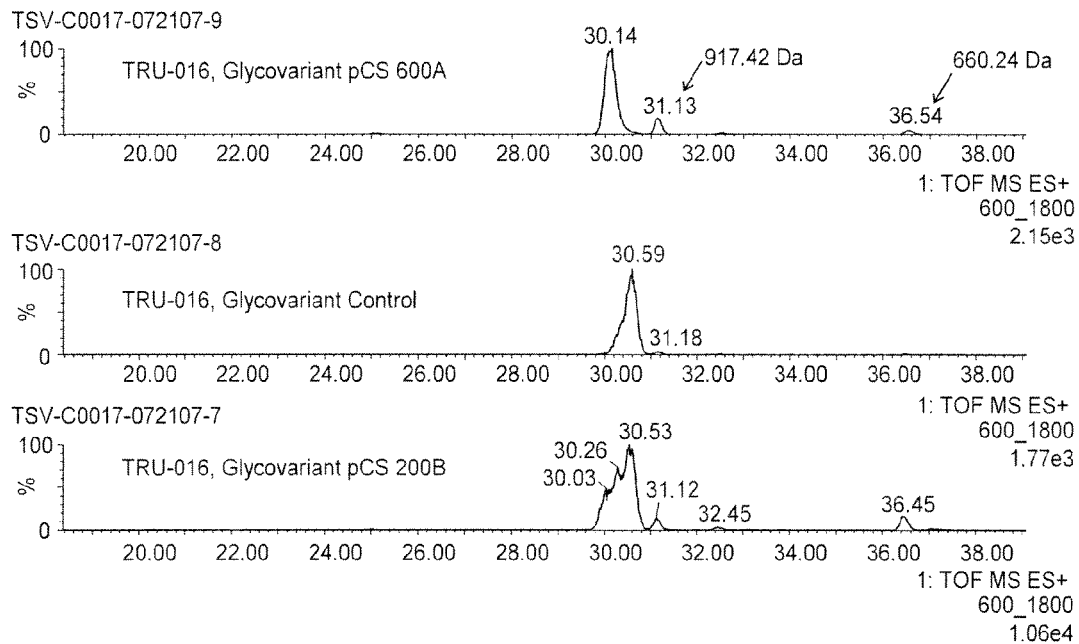
FIGURE 26

MATERIALS AND METHODS FOR IMPROVED IMMUNOGLYCOPROTEINS

CROSS-REFERENCE TO RELATED APPLICATIONS

This application is a continuation in-part of International Patent Application PCT/US2007/082343 filed Oct. 24, 2007, which claims the benefit of prior U.S. provisional application No. 60/853,944 filed Oct. 24, 2006, both of which are hereby incorporated by reference in their entirety.

FIELD OF THE INVENTION

The invention relates to immunoglycoproteins, including antibodies, that have improved properties, including antibody-dependent cell cytotoxicity and glycosylation patterns, cell culturing methods and media for producing such immunoglycoproteins, and uses of such immunoglycoproteins in treatment of disease.

BACKGROUND

Elimination of targeted cell populations with immunopharmaceuticals is an important therapeutic intervention in several indications. The mechanisms of action used by immunopharmaceuticals to effect such elimination of targeted cells can include complement mediated cellular lysis, activation of apoptotic signaling pathways, blockade of signaling pathways required for survival, and antibody-dependent cellular cytotoxicity (ADCC), also referred to as Fc-dependent cellular cytotoxicity. ADCC is a potent mechanism that is believed to be important for the efficacy of many immunopharmaceuticals.

The mechanism for activation of ADCC involves binding of Fc receptors to immunopharmaceutical molecules that are bound to the surface of the target cell. The binding of Fc receptors to immunopharmaceuticals can be mediated by domains within the constant region of immunoglobulins, such as the CH2 and/or CH3 domains. Different types of constant regions may bind different Fc receptors. Examples include the binding of IgG1 Fc domains to cognate Fc receptors CD16 (FcγRIII), CD32 (FcγRII-B1 and -B2), and CD64 (FcγRI), IgA Fc domains to the cognate Fc receptor CD89 (FcαRI), and IgE domains to cognate Fc receptors FcεFR1 and CD23.

Immunopharmaceutical compositions with enhanced Fc receptor binding may exhibit greater potency in ADCC. Reported methods of achieving this with IgG Fc domains include the introduction of amino acid changes and the modification of carbohydrate structures. Modification of carbohydrate structures may be preferable as amino acid changes in the Fc domain may enhance immunogenicity of a pharmaceutical composition. For immunoglobulin molecules it has been demonstrated that attachment of N-linked carbohydrate (oligosaccharide) to Asn-297 of the CH2 domain is critical for ADCC activity. Its removal enzymatically or through mutation of the N-linked consensus site results in little to no ADCC activity. Some studies have reported that the level of ADCC activity for an immunoglobulin molecule is also dependent on the structure of the carbohydrate, but the actual carbohydrate moieties or structure responsible for ADCC have not yet been elucidated. Still less is known about the optimal carbohydrate structure(s) for ADCC of non-immunoglobulin Fc fusion proteins.

In glycoproteins, carbohydrates may attach to the amide nitrogen atom in the side chain of an asparagine in a tripeptide motif Asn-X-Thr/Ser. This type of glycosylation, termed N-linked glycosylation, commences in the endoplasmic reticulum (ER) with the addition of multiple monosaccharides to a dolichol phosphate to form a 14-residue branched carbohydrate complex. This carbohydrate complex is then transferred to the protein by the oligosaccharyltransferase (OST) complex. Before the glycoprotein leaves the lumen of the ER, three glucose molecules are removed from the 14-residue oligosaccharide. The enzymes ER glucosidase I, ER glucosidase II and ER mannosidase are involved in ER processing.

Subsequently, the polypeptides are transported to the Golgi complex, where the N-linked sugar chains are modified in many different ways. In the cis and medial compartments of the Golgi complex, the original 14-saccharide N-linked complex may be trimmed through removal of mannose (Man) residues and elongated through addition of N-acetylglucosamine (GlcNac) and/or fucose (Fuc) residues. The various forms of N-linked carbohydrates generally have in common a pentasaccharide core consisting of three mannose and two N-acetylglucosamine residues. Finally, in the trans Golgi, other GlcNac residues can be added, followed by galactose (Gal) and a terminal sialic acid (Sial). Carbohydrate processing in the Golgi complex is called "terminal glycosylation" to distinguish it from "core glycosylation," which takes place in the ER. The final complex carbohydrate units can take on many forms and structures, some of which have two, three or four branches (termed biantennary, triantennary or tetraantennary). A number of enzymes are involved in Golgi processing, including Golgi mannosidases IA, IB and IC, GlcNAc-transferase I, Golgi mannosidase II, GlcNAc-transferase II, Galactosyl transferase and Sialyl transferase.

One report has suggested that a crucial carbohydrate determinant of FcγRIIIa receptor-mediated ADCC activity is the lack of an alpha-1,6-fucose moiety added to the core N-linked structure (Shinkawa et al., *J Biol Chem.* 2003 Jan. 31; 278(5): 3466-73; see also Shields et al., *J Biol Chem.* 2002 Jul. 26; 277(30):26733-40). The level of another glycoform, bisected N-linked carbohydrate, has also been proposed to be capable of imparting increased ADCC (Umana et al., *Nat. Biotechnol.* 1999 February; 17(2): 176-80) but there is also contradictory evidence (Shinkawa et al., *J Biol Chem.* 2003 Jan. 31; 278 (5):3466-73). A potential solution to this contradictory evidence has been suggested by the finding that increased GnTIII in host cells produces immunoglobulin not only with increased bisected sugar but also lacking the core fucose modification (Ferrara et al., *Biotechnol Bioeng.* 2006 Apr. 5; 93(5):851-61). This agrees with suggestion that fucose alone has the key role in altering ADCC potency and the association with bisected sugar seen by others reflects a linkage in the two modifications in host cells. However, another report in which in vitro treatment of Rituxan and Herceptin antibodies with GnTIII, to increase bisected sugar, resulted in increased ADCC suggests a direct effect of bisected sugar (Hodoniczky et al., *Biotechnol. Prog.*, 2005 November-December 21(6): 1644-52). However, overexpression of Gnt III at very high levels may be toxic to the cell (Umana et al., Biotechnol Prog. 1998 March-April; 14(2):189-92).

Some proposed methods for producing immunoglobulins with lower fucose content have significant drawbacks for manufacture of a biopharmaceutical drug with an optimal ADCC activity for the therapeutic indication. For example, treatment of immunoglobulins with enzymes that remove fucose residues (fucosidases) involves additional costly manufacturing steps with potentially significant economic and drug consistency risks. Molecular engineering of cell lines to knock-out key enzymes involved in the synthesis of fucosylated glycoproteins require special host strains and in current practice do not allow for "tunable" production of drug with varying ADCC potency to optimize efficacy and safety for a therapeutic use. Generation of a comparison non-enhanced ADCC product is expensive and time consuming. The treatment of cell lines with RNAi or antisense molecules to knock down the level of these key enzymes may have unpredictable off-target effects and would be costly if not impractical to implement at manufacturing scale.

Thus, there continues to exist a need for advantageous methods of preparing immunopharmaceuticals with enhanced ADCC as well as for the improved immunopharmaceuticals produced thereby for therapeutic uses.

SUMMARY OF THE INVENTION

The invention provides compositions of immunoglycoproteins with a characteristic N-linked oligosaccharide content and improved properties, including effector functions such as ADCC. The invention also provides uses of such immunoglycoproteins and sterile compositions thereof in treatment of disease, culture media comprising such immunoglycoproteins and/or host cells that produce them, and large scale cell culture methods for improving the properties of such immunoglycoproteins. The immunoglycoprotein compositions of the invention can be characterized, for example, by glucose content or hexose content and/or fucose content of the composition as a whole, depending on the number of N-linked glycosylation sites for potential oligosaccharide linkage, or depending on the number of N-linked oligosaccharides in the composition of immunoglycoprotein molecules. Alternatively, or in addition, the immunoglycoprotein compositions of the invention can be characterized by glucose content, hexose content and/or fucose content of the N-linked oligosaccharides. As yet another alternative, or in addition, the immunoglycoproteins of the invention can be characterized by the glucose, hexose and/or fucose content of one or more major reduced immunoglycoprotein species that represents a certain percentage of the composition.

The invention contemplates compositions comprising recombinant immunoglycoprotein molecules comprising one or more N-linked glycosylation sites for potential linkage of oligosaccharide. In one aspect, the immunoglycoprotein molecules in the composition comprise an N-linked glycosylation site and have a glucose content characterized by a ratio of glucose molecules per said N-linked glycosylation site of at least 1.2. In other exemplary compositions the ratio of glucose molecules per said N-linked glycosylation site is at least about 1.4, 1.5, 1.6, 1.8, 2, 2.2, 2.4, 2.6, or 2.8 or more. The composition of immunoglycoprotein molecules may also be characterized by a hexose content of at least about 9, 9.2, 9.4, 9.6, 9.8, or 10 or more hexoses per said N-linked glycosylation site, and/or a fucose content of less than about 1, 0.8, 0.6, or 0.4 or less, per said N-linked glycosylation site.

In some embodiments, the immunoglycoprotein molecules of the composition comprise one or more CH2-derived domains, and at least one CH2-derived domain is characterized by a ratio of saccharide per N-linked glycosylation site(s) of at least 1.2. In other exemplary compositions at least one CH2-derived domain is characterized by a ratio of glucose molecules per N-linked glycosylation site(s) of at least about 1.4, 1.5, 1.6, 1.8, 2, 2.2, 2.4, 2.6, or 2.8 or more. The CH2-derived domain may also be characterized by a hexose content of at least about 9, 9.2, 9.4, 9.6, 9.8, or 10 or more hexoses per N-linked glycosylation site, and/or a fucose content of less than about 1, 0.8, 0.6, or 0.4 or less, per N-linked glycosylation site.

In some embodiments, the immunoglycoprotein molecules comprise an N-linked glycosylation site, and a certain percentage, e.g., at least about 40%, of the N-linked oligosaccharides at said N-linked glycosylation site have a glucose content of one to three glucose molecules, e.g., 1, 2, or 3. In some embodiments, a certain percentage, e.g., at least about 40%, of the N-linked oligosaccharides at said N-linked glycosylation site in the compositions of the invention have a glucose content of two to three glucose molecules. In exemplary embodiments, such percentage is at least about 45%, 50%, 55%, 60%, 65%, 70%, 75%, 80%, 85%, 90% or at least 95% or more. Thus, for example, in some embodiments, at least 40%, or at least 45%, 50%, 55%, 60%, 65%, 70%, 75%, 80%, 85%, 90% or at least 95% or more of the N-linked oligosaccharides at said N-linked glycosylation site have a glucose content of two glucose molecules. In some embodiments, at least 40%, or at least 45%, 50%, 55%, 60%, 65%, 70%, 75%, 80%, 85%, 90% or at least 95% or more of said N-linked oligosaccharides of said immunoglycoprotein molecules have a glucose content of three glucose molecules.

In some embodiments, the immunoglycoprotein molecules of the composition comprise one or more CH2-derived domains, and at least one CH2-derived domain is characterized by a certain percentage, e.g., at least about 40%, of the N-linked oligosaccharides having a glucose content of one to three glucose molecules, e.g., 1, 2, or 3. In some embodiments, a certain percentage, e.g., at least about 40%, of the N-linked oligosaccharides of said CH2-derived domain have a glucose content of two to three glucose molecules. In exemplary embodiments, such percentage is at least about 45%, 50%, 55%, 60%, 65%, 70%, 75%, 80%, 85%, 90% or at least 95% or more. Thus, for example, in some embodiments, at least 40%, or at least 45%, 50%, 55%, 60%, 65%, 70%, 75%, 80%, 85%, 90% or at least 95% or more of said N-linked oligosaccharides of said CH2-derived domain are linked to two glucose molecules. In some embodiments, at least 40%, or at least 45%, 50%, 55%, 60%, 65%, 70%, 75%, 80%, 85%, 90% or at least 95% or more of said N-linked oligosaccharides of said CH2-derived domain are linked to three glucose molecules.

In some embodiments, a certain percentage, e.g., at least about 40%, of the N-linked oligosaccharides at said a N-linked glycosylation site in the compositions of the invention have a hexose content of at least ten hexoses. In some embodiments, a certain percentage, e.g., at least about 40%, of the N-linked oligosaccharides at said N-linked glycosylation site in the compositions of the invention are characterized by a hexose content of ten hexoses. In some embodiments, such percentage is at least about 45%, 50%, 55%, 60%, 65%, 70%, 75%, 80%, 85%, 90% or at least 95% or more of said N-linked oligosaccharides of said immunoglycoprotein molecules.

In some embodiments, the immunoglycoprotein molecules of the composition comprise one or more CH2-derived domains, and at least one CH2-derived domain is characterized by a certain percentage, e.g., at least about 40%, of the N-linked oligosaccharides of said CH2-derived domain have a hexose content of at least ten hexoses. In some embodiments, a certain percentage, e.g., at least about 40%, of the N-linked oligosaccharides of the CH2-derived domains are characterized by a hexose content of ten hexoses. In some embodiments, such percentage is at least about 45%, 50%, 55%, 60%, 65%, 70%, 75%, 80%, 85%, 90% or at least 95% or more of said N-linked oligosaccharides of said CH2-derived domains.

Any of the preceding compositions of recombinant immunoglycoprotein molecules may exhibit at least about 2-fold, 3-fold, 4-fold or 5-fold higher ADCC or CD16-binding compared to control immunoglycoprotein molecules of the same encoded amino acid sequence produced in CHO-K1 cells in the absence of carbohydrate modifier. In other embodiments, the immunoglycoprotein molecules exhibit at least about 6-fold, about 7-fold, about 8-fold, about 9-fold, about 10-fold, about 20-fold, about 30-fold, about 40-fold, about 50-fold, about 60-fold, about 70-fold, about 80-fold, about 90-fold, about 100-fold or more higher ADCC or CD 16-binding compared to control immunoglycoprotein molecules of the same encoded amino acid sequence produced in CHO-K1 cells in the absence of carbohydrate modifier. Improved binding to the high affinity, low affinity, or advantageously both types of CD16 alleles (V158 high affinity and F158 low affinity) is observed.

Any of the preceding compositions of recombinant immunoglycoprotein molecules may further be characterized by a fucose content wherein at least about 60% of the N-linked oligosaccharides, e.g. N-linked oligosaccharides in the CH2-derived domains, contain no fucose. In related embodiments, the percentage of N-linked oligosaccharides, e.g. N-linked oligosaccharides in the CH2-derived domains, that contain no fucose is at least about 65%, about 70%, about 75%, about 80%, about 85%, about 90%, about 95% or more.

In some embodiments of the invention, such immunoglycoprotein molecules comprising a N-linked glycosylation site in the compositions of the invention exhibit more than one of the foregoing properties, for example, (1) glucose content (e.g., of the CH2-derived domain) characterized by a ratio of glucose molecules per said N-linked glycosylation site of at least 1.2, (2) at least 40% of the N-linked oligosaccharides (e.g., of the CH2-derived domain) at said N-linked glycosylation site have a glucose content of two to three glucose molecules, (3) at least 60% of the N-linked oligosaccharides (e.g., of the CH2-derived domain) at said N-linked glysosylation site have a hexose content of ten hexose molecules, (4) at least 5-fold higher ADCC compared to control immunoglycoprotein molecules of the same encoded amino acid sequence produced in CHO-K1 cells in the absence of carbohydrate modifier, and (5) at least 60% of the N-linked oligosaccharides (e.g., of the CH2-derived domain) at said N-linked glycosylation site contain no fucose.

Exemplary immunoglycoproteins of the invention include immunoglobulins and small, modular immunopharmaceutical (SMIP™) products. Such binding molecules advantageously retain substantially the same properties of binding to target and resulting direct biological activity, but exhibit improved effector-mediated functions.

In some embodiments of the invention, the recombinant immunoglycoprotein molecules, in a reduced state, have a single N-linked glycosylation site. In other embodiments, the recombinant immunoglycoprotein molecules have two, three, four or more N-linked glycosylation sites. In some embodiments of the invention, the immunoglycoprotein molecules are monovalent, while in other embodiments, they are multivalent, e.g., bivalent, trivalent, tetravalent or higher multivalencies. In some embodiments, the immunoglycoprotein molecules are monomeric, while in other embodiments, they are multimeric, e.g., dimeric, trimeric, tetrameric, or higher multimeric. In some embodiments, the immunoglycoprotein molecules are monospecific for a target, while in other embodiments, they are multispecific, e.g., bispecific, trispecific, or higher multispecific in antigen-binding. It is contemplated that in some embodiments, for example, within a multimeric molecule, the N-linked oligosaccharide (e.g., of the CH2-derived domain) on one monomer of the multimer may be different from the N-linked oligosaccharide on another monomer within the same multimer. For example, within an immunoglycoprotein molecule, one N-linked oligosaccharide (e.g., of the CH2-derived domain) may have two glucoses linked thereto, while the other N-linked oligosaccharide may have no glucoses linked thereto.

In another aspect, a method of the invention may involve growing a host cell capable of producing immunoglycoproteins in a volume of at least about 75 or 100 liters of culture medium comprising castanospermine at a concentration between about 25 µM and about 800 µM. In some embodiments, methods involve growing a host cell capable of producing immunoglycoproteins in a volume of at least about 150, 200, 300, 400, 500, 600, 700, 800, 900, 1000, 1500, 2000, 2500, 3000, 3500, 4000, 4500, 5000, 5500, 6000, 6500, 7000, 7500, 8000, or 10,000 or more liters of culture medium comprising a carbohydrate modifier, e.g., castanospermine at a concentration between about 25 µM and about 800 µM. In related embodiments, any of the preceding compositions may comprise immunoglycoprotein molecules and any of the foregoing volumes of culture media, e.g., essentially serum-free media, and optionally further comprise host cells capable of producing the immunoglycoprotein molecules.

In some embodiments, any of the preceding compositions may comprise at least about 50, 75, or 100 g of immunoglycoprotein molecules, optionally with a pharmaceutically acceptable carrier or diluent. In exemplary embodiments, the composition may comprise at least about 125, 150, 175, 200, 300, 400, 500, 600, 700, 800, 900, 1000 or more grams of immunoglycoprotein molecules, optionally with a pharmaceutically acceptable carrier or diluent. Such compositions may be sterile, or may be in a container or kit as described herein.

In another aspect, the invention provides a method for increasing the antibody-dependent cytoxicity (ADCC) of immunoglycoprotein molecules produced by a host cell, by growing the host cell in culture medium comprising castanospermine at a concentration between about 25 and about 800 µM, or between about 100 and about 500 µM, or between about 100 and about 400 µM, or between about 100 and about 300 µM. In exemplary embodiments, the ADCC is increased at least 2-fold, 3-fold, 4-fold or 5-fold.

In related embodiments, the invention provides a method for increasing the CD16 binding of immunoglycoprotein molecules produced by a host cell, by growing the host cell in culture medium comprising castanospermine at a concentration between about 25 and about 800 µM, or between about 100 and about 500 µM, or between about 100 and about 400 µM, or between about 100 and about 300 µM. In exemplary embodiments, the CD16 binding is increased by at least 50%, 75%, 100%, 125%, 150%, 175% or 200%.

In the methods of the invention, cell growth, viability and/or density is not significantly affected (e.g. remains at least 80% or higher of untreated cells). The level of immunoglycoprotein production in the culture medium may be at least 100 µg/mL, 125 µg/mL, or 150 µg/mL.

In any of the preceding embodiments the culture medium may be essentially serum-free, and may include a second carbohydrate modifier.

The invention also contemplates compositions comprising any of the immunoglycoprotein molecules described herein, optionally with a sterile pharmaceutically acceptable carrier or diluent. Such compositions may be administered in methods of killing or inhibiting growth of cancer cells which express on their surface a molecule bound by said immunoglycoprotein molecules, or in methods of depleting cells that express on their surface a molecule bound by said immunoglycoprotein molecules.

In another aspect, methods of the invention may generally involve culturing host cells producing the immunoglycoproteins in culture media containing an appropriate concentration of carbohydrate modifier, e.g. castanospermine, and provide an advantage of improving effector function without significantly affecting cell growth or protein production levels. Exemplary immunoglycoproteins that can be manufactured using the methods of the invention include immunoglobulins and small, modular immunopharmaceutical (SMIP™) products. Such binding molecules prepared according to the methods of the invention advantageously retain substantially the same properties of binding to target and resulting direct biological activity, but exhibit improved effector-mediated functions.

In one aspect, the invention provides a method for improving the antibody-dependent cytoxicity (ADCC) and/or the Fc receptor binding of immunoglycoproteins produced by a host cell. Such methods involve growing the host cell in a volume of at least 750 mL, 1 L, 2 L, 3 L, 4 L, 5 L, 10 L, 15 L, 20 L or more of culture medium comprising a carbohydrate modifier, e.g., castanospermine, at a concentration that increases the ADCC activity and/or Fc receptor binding of a composition of immunoglycoprotein molecules produced by the host cell. While the optimal concentration of such carbohydrate modifier, e.g., castanospermine, depends on the potency of the carbohydrate modifier and the relative modulation of ADCC desired, exemplary final concentrations of carbohydrate modifiers in the culture media are less than 800 μM, or less than 750, 700, 650, 600, 550, 500, 450, 400, 350, 300, 250, 200, 150, 125, 100, 90, 80, 70, 60, 50, 40, 30, 20, or 10 μM.

The relative effect on ADCC may be modulated by altering the concentration or duration of the carbohydrate modifier, e.g., castanospermine, applied to the cell culture, providing an additional advantage compared to conventional methods of improving ADCC by altering glycosylation. ADCC activity may be measured and expressed using assays known in the art and in exemplary embodiments increases by at least 10%, 20%, 30%, 40%, 50%, 60%, 70%, 80%, 90%, 2-fold, 3-fold, 4-fold, 5-fold, 6-fold, 7-fold, 8-fold, 9-fold, 10-fold, 15-fold or 20-fold.

Glycosylation and carbohydrate content is known to affect a variety of immunoglobulin effector-mediated functions, including ADCC, CDC and circulating half-life. The data described herein show that the methods of the invention and the compositions of the invention are surprisingly able to provide immunoglycoproteins that exhibit improved ADCC without affecting CDC or half-life. Thus, in exemplary embodiments, ADCC of the immunoglycoprotein molecule composition is increased but other immunoglobulin-type effector functions, such as complement-dependent cytoxicity (CDC) and/or prolonged circulating half-life, remain similar or are not significantly affected (e.g., less than 2-fold increase or decrease, or less than 50%, 40%, 30%, 20% or 10% increase or decrease).

The Fc receptor binding of the composition of immunoglycoprotein molecules may be determined as the relative ratio of carbohydrate modifier-treated immunoglycoprotein molecules, vs. untreated immunoglycoprotein molecules, that bind to CD16. Exemplary assays are described below in the examples. Fc receptor binding in exemplary embodiments increases by at least 10%, 20%, 30%, 40%, 50%, 60%, 70%, 80%, 90%, 2-fold, 3-fold, 4-fold, 5-fold or 6-fold. An immunoglycoprotein composition produced by host cells treated with carbohydrate modifier, e.g., castanospermine, according to the invention will bind to CD16 (high and low affinity forms, i.e. V or F at amino acid 158) and/or CD32 a or b and/or CD64 with greater affinity in FcR binding assays than immunoglycoprotein compositions produced by host cells not so treated. This increase in Fc receptor binding affinity is shown herein to correlate to an increase in ADCC activity.

The invention also provides methods for altering the carbohydrate content/glycosylation pattern and/or decreasing the fucose content of immunoglycoproteins by growing the host cell in a volume of at least 750 mL, 1 L, 2 L, 3 L, 4 L, 5 L, 10 L, 15 L, 20 L, 50 L, 100 L, 150 L, 200 L, 250 L, 300 L, 350 L, 400 L, 500 L, 600 L, 700 L, 800 L, 900 L, 100 L, 10,000 L or more of culture medium comprising a carbohydrate modifier, e.g., castanospermine, at a concentration that decreases the total fucose content and/or alters the glycosylation pattern of a composition of immunoglycoprotein molecules produced by the host cell. Exemplary final concentrations of carbohydrate modifiers, e.g., castanospermine, in the culture media are less than 800 μM, or less than 750, 700, 650, 600, 550, 500, 450, 400, 350, 300, 250, 200, 150, 125, 100, 90, 80, 70, 60, 50, 40, 30, 20, or 10 μM.

The relative effect on fucose content may also be modulated by altering the concentration or duration of the carbohydrate modifier, e.g., castanospermine, applied to the cell culture. The total fucose content of a composition of the invention may be expressed as the relative ratio or percentage of non-fucosylated immunoglycoprotein molecules to the total number of immunoglycoprotein molecules in a composition. Exemplary compositions contain at least 30%, 40%, 50%, 60%, 65%, 70%, 75%, 80%, 85%, 90%, 95% or more non-fucosylated molecules. The fucose content of an immunoglycoprotein composition produced by host cells treated with carbohydrate modifier, e.g., castanospermine, according to the invention will be reduced at least 2-fold, 3-fold, 4-fold, 5-fold, 6-fold, 7-fold, 8-fold, 9-fold or 10-fold or more compared to compositions produced by host cells not so treated.

In any of the foregoing methods, the host cells may exhibit high levels of growth during exposure to carbohydrate modifiers, e.g., castanospermine. For example, an exemplary population doubling time of CHO cells producing immunoglycoproteins is about 24 hours; a concentration of carbohydrate modifier according to the invention (e.g. a concentration effective to increase ADCC) is not expected to decrease such doubling time. Ideally, an effective concentration of carbohydrate modifier, e.g., castanospermine, does not reduce cell growth by more than 10, 20, 30, 40, 50, 60 or 70% at a time point 72 hours after addition of the carbohydrate modifier.

In any of the foregoing methods, the host cells may exhibit high levels of protein production during exposure to carbohydrate modifiers, e.g., castanospermine. For example, protein production levels in the presence of an effective concentration of carbohydrate modifier, e.g., castanospermine, may be about 50 μg/mL or higher, or about 75, 100, 125, or 150 μg/mL, or higher. Preferably the host cells exhibit both high levels of growth and high levels of protein production.

Any culture media known in the art, including essentially serum-free culture media, may be used. Fed batch, continuous feed, and other types of culturing methods known in the art may also be used with the methods of the invention. The carbohydrate modifiers may be added to the seed train, to the initial batch culture medium, after a rapid growth phase, or continuously with culture medium (e.g. during continuous feeding). For example, the carbohydrate modifier may be added to an early seed train or feedstock at a 10× or 100× concentration, such that subsequent additions of culture media dilute the concentration of carbohydrate modifier to a level that is still effective in achieving improved ADCC of the recombinant products. Alternatively, the carbohydrate modifier at an effective concentration is included in all culture media added to the cells, obviating the need for dilution. In either case, the carbohydrate modifier is added relatively early in the cell culturing process and an effective concentration is maintained throughout the culturing process in order to optimize homogeneity of the immunoglycoprotein. The effect of carbohydrate modifiers is believed to be long-lasting, and can continue to be observed at least 11-12 days after a one-time addition of carbohydrate modifier.

Exemplary carbohydrate modifiers include core glycosylation inhibitors, terminal glycosylation inhibitors, mannosidase inhibitors, and/or early stage carbohydrate modifiers, and optionally include or exclude fucosylation-specific inhibitors, and are described in more detail below. The invention contemplates that combinations of two or more, or three or more carbohydrate modifiers may provide added benefits. Castanospermine is one specifically contemplated carbohydrate modifier.

In another aspect, any of the compositions of the invention provide immunoglycoprotein molecules that preferably have a binding affinity Kd of at least $10^7$ $M^{-1}$, or at least $10^8$ $M^{-1}$, or $10^9$ $M^{-1}$ for a target molecule. Such compositions may comprise one or more sterile pharmaceutically acceptable carriers or diluents.

In a further aspect, the invention provides therapeutic methods involving administration of any of the compositions described herein to subjects that would benefit from such administration, e.g. suffering from a disorder mediated by cells expressing the target molecule, or suffering from a type of cancer in which the cancer cells express the target molecule on their surface. The invention also contemplates use of such compositions in methods of depleting cells expressing the target molecule on their surface. Where the target is CD37, the invention specifically contemplates a method of inhibiting cancer cell growth or destroying cancer cells comprising the step of administering to a subject a composition comprising anti-CD37 SMIP products produced according to the methods of the invention. Similarly, where the target is CD20, the invention specifically contemplates a method of inhibiting cancer cell growth or destroying cancer cells comprising the step of administering to a subject a composition comprising anti-CD20 SMIP products produced according to the methods of the invention. In related embodiments, methods of treating cancer involving arresting or reversing cancer progression are contemplated. The invention further provides methods of treating autoimmune or inflammatory diseases by administering anti-CD37 or anti-CD20 SMIP products produced according to the methods of the invention. In related aspects, the invention contemplates use of the glycoprotein compositions of the invention, optionally comprising a sterile carrier or diluent, in preparation of a medicament for treating any of the diseases or disorders described herein.

Immunoglycoproteins

The term "immunoglycoprotein" refers to a glycosylated polypeptide that binds to a target molecule and contains sufficient amino acid sequence derived from a constant region of an immunoglobulin to provide an effector function, preferably ADCC and/or CDC. Exemplary molecules will contain a sequence derived from a CH2 domain of an immunoglobulin, or CH2 and CH3 domains derived from one or more immunoglobulins. Specific subsets of immunoglycoproteins contemplated for production according to the invention include single chain proteins which optionally dimerize through covalent or non-covalent associations in the hinge and/or CH3 domains. This subset of single chain proteins excludes the typical tetrameric conformation of immunoglobulins (due to the absence of light chains) but includes Fc-ligand or Fc-soluble receptor fusions. Specific examples of single chain proteins include SMIP products.

SMIP products and methods of producing them have been described previously in co-owned U.S. application Ser. No. 10/627,556, and US Patent Publications 2003/133939, 2003/0118592, and 2005/0136049, each of which are incorporated herein by reference in their entirety. Single-Chain Multivalent Binding Proteins with Effector Function are described in International Patent Application No. PCT/US07/71052, filed Jun. 12, 2007 (claiming the benefit of U.S. Ser. No. 60/813,261, filed Jun. 12, 2006 and 60/853,287, filed Oct. 20, 2006), each of which are incorporated herein by reference in their entirety. SMIP products are novel binding domain-immunoglobulin fusion proteins that feature a binding domain for a cognate structure such as an antigen, a counterreceptor or the like; an IgG1, IgA or IgE hinge region polypeptide or a mutant IgG1 hinge region polypeptide having either zero, one or two cysteine residues; and immunoglobulin CH2 and CH3 domains. In one embodiment, the binding domain molecule has one or two cysteine residues. In a related embodiment, it is contemplated that when the binding domain molecule comprises two cysteine residues, the first cysteine, which is typically involved in binding between the heavy chain and light chain variable regions, is not deleted or substituted with an amino acid. SMIPs products are capable of ADCC and/or CDC but may be compromised in their ability to form disulfide-linked multimers. Exemplary SMIP products may have one or more binding regions, such as a binding region of an immunoglobulin superfamily member of a variable light chain and/or variable heavy chain binding region derived from an immunoglobulin. In exemplary embodiments these regions are separated by linker peptides, which may be any linker peptide known in the art to be compatible with domain or region joinder. Exemplary linkers are linkers based on the Gly4Ser linker motif, such as (Gly4Ser)n, where n=3-5.

As described in International Patent Application No. PCT/US07/71052, filed Jun. 12, 2007, incorporated herein by reference in its entirety, multivalent single-chain binding proteins with effector function may comprise a first binding domain derived from an immunoglobulin (e.g., an antibody) or an immunoglobulin-like molecule, a constant sub-region providing an effector function, the constant sub-region located C-terminal to the first binding domain; a scorpion linker located C-terminal to the constant sub-region; and a second binding domain derived from an immunoglobulin (such as an antibody) or immunoglobulin-like molecule, located C-terminal to the constant sub-region; thereby localizing the constant sub-region between the first binding domain and the second binding domain. The single-chain binding protein may be multispecific, e.g., bispecific in that it could bind two or more distinct targets, or it may be monospecific, with two binding sites for the same target. Moreover, all of the domains of the protein are found in a single chain, but the protein may form homo-multimers, e.g., by interchain disulfide bond formation. In some embodiments, the first binding domain and/or the second binding domain is/are derived from variable regions of light and heavy immunoglobulin chains from the same, or different, immunoglobulins (e.g., antibodies).

Scorpion linkers comprise at least about 5 amino acids attached to the immunoglobulin constant sub-region and attached to the second binding domain, thereby localizing the scorpion linker between the constant sub-region and the second binding domain. Typically, the scorpion linker peptide length is between 5-45 amino acids. Scorpion linkers include hinge-like peptides derived from immunoglobulin hinge regions, such as IgG1, IgG2, IgG3, IgG4, IgA, and IgE hinge regions. Preferably, a hinge-like scorpion linker will retain at least one cysteine capable of forming an interchain disulfide bond under physiological conditions. Scorpion linkers derived from IgG1 may have 1 cysteine or two cysteines, and will preferably retain the cysteine corresponding to an N-terminal hinge cysteine of IgG1. Non-hinge-like peptides are also contemplated as scorpion linkers, provided that such peptides provide sufficient spacing and flexibility to provide a single-chain protein capable of forming two binding domains, one located towards each protein terminus (N and C) relative to a more centrally located constant sub-region domain. Exemplary non-hinge-like scorpion linkers include peptides from the stalk region of type II C-lectins, such as the stalk regions of CD69, CD72, CD94, NKG2A and NKG2D.

Exemplary SMIP products that can be produced according to the invention include products that bind CD20 or CD37. SMIP products that bind CD20 or CD37 and that comprise specific binding sequences and/or amino acid modifications are described in co-owned, co-pending U.S. application Ser. Nos. 10/627,556 and 11/493,132, each hereby incorporated by reference in its entirety.

The CH2 domain of immunoglobulins corresponds to amino acids Ala231-Lys340 of the immunoglobulin heavy chain, using Kabat numbering. As used herein, a "CH2-derived domain" means a domain based on or derived from an immunoglobulin CH2 domain that retains one or more effector functions of the domain, e.g. ADCC and/or CDC. Such CH2-derived domains will retain the N-linked glycosylation site at Asn297, using Kabat numbering. Exemplary CH2-derived domains retain at least 30%, 40%, 50%, 60%, 70%, 80%, or 90% amino acid identity to CH2 of an immunoglobulin, e.g. a human immunoglobulin or human consensus immunoglobulin sequence. Regions involved in FcR binding for ADCC and CDC have been evaluated in the art. Regions that may be modified without significantly affecting ADCC are generally disclosed in the art, e.g., U.S. Pat. No. 6,737,056. Insertions, deletions, or substitutions, including conservative substitutions may be made within the CH2 domain provided that it retains effector function and retains the Asn297 N-linked glycosylation site. Methods for engineering and testing such mutations are well known in the art.

Other examples of immunoglycoproteins include binding domain-Ig fusions, wherein the binding domain may be a non-naturally occurring peptide or a fragment of a naturally occurring ligand or receptor. In the case of receptors, fragments of the extracellular domain are preferred. Exemplary fusions with immunoglobulin or Fc regions include: etanercept which is a fusion protein of sTNFRII with the Fc region (U.S. Pat. No. 5,605,690), alefacept which is a fusion protein of LFA-3 expressed on antigen presenting cells with the Fc region (U.S. Pat. No. 5,914,111), a fusion protein of Cytotoxic T Lymphocyte-associated antigen-4 (CTLA-4) with the Fc region [J. Exp. Med., 181, 1869 (1995)], a fusion protein of interleukin 15 with the Fc region [J. Immunol., 160, 5742 (1998)], a fusion protein of factor VII with the Fc region [Proc. Natl. Acad. Sci. USA, 98, 12180 (2001)], a fusion protein of interleukin 10 with the Fc region [J. Immunol., 154, 5590 (1995)], a fusion protein of interleukin 2 with the Fc region [J. Immunol., 146, 915 (1991)], a fusion protein of CD40 with the Fc region [Surgery, 132, 149 (2002)], a fusion protein of Flt-3 (fins-like tyrosine kinase) with the antibody Fc region [Acta. Haemato., 95, 218 (1996)], a fusion protein of OX40 with the antibody Fc region [J. Leu. Biol., 72, 522 (2002)], other CD molecules [e.g., CD2, CD30 (TNFRSF8), CD95 (Fas), CD106 (VCAM-1), CD137], adhesion molecules [e.g., ALCAM (activated leukocyte cell adhesion molecule), cadherins, ICAM (intercellular adhesion molecule)-1, ICAM-2, ICAM-3], cytokine receptors [e.g., interleukin-4R, interleukin-5R, interleukin-6R, interleukin-9R, interleukin-10R, interleukin-12R, interleukin-13Rα1, interleukin-13Rα2, interleukin-15R, interleukin-21R], chemokines, cell death-inducing signal molecules [e.g., B7-H1, DR6 (Death receptor 6), PD-1 (Programmed death-1), TRAIL R1], costimulating molecules [e.g., B7-1, B7-2, B7-H2, ICOS (inducible co-stimulator)], growth factors [e.g., ErbB2, ErbB3, ErbB4, HGFR], differentiation-inducing factors (e.g., B7-H3), activating factors (e.g., NKG2D), signal transfer molecules (e.g., gp130).

Yet other examples of immunoglycoproteins include antibodies. The term "antibody" herein is defined to include fully assembled antibodies, monoclonal antibodies, polyclonal antibodies, multispecific antibodies (e.g., bispecific antibodies), antibody fragments that can bind antigen (e.g., Fab', F'(ab)2, Fv, single chain antibodies, diabodies), and recombinant peptides comprising the forgoing as long as they exhibit the desired antigen-binding activity. Multimers or aggregates of intact molecules and/or fragments, including chemically derivatized antibodies, are contemplated. Antibodies of any isotype class or subclass, including IgG, IgM, IgD, IgA, and IgE, IgG1, IgG2, IgG3, IgG4, IgA1 and IgA2, are contemplated. Different isotypes have different effector functions; for example, IgG1 and IgG3 isotypes have antibody-dependent cellular cytotoxicity (ADCC) activity.

An "immunoglobulin" or "native antibody" is a tetrameric glycoprotein composed of two identical pairs of polypeptide chains (two "light" and two "heavy" chains). The amino-terminal portion of each chain includes a "variable" ("V") region of about 100 to 110 or more amino acids primarily responsible for antigen recognition. Within this variable region, the "hypervariable" region or "complementarity determining region" (CDR) consists of residues 24-34 (L1), 50-56 (L2) and 89-97 (L3) in the light chain variable domain and 31-35 (H1), 50-65 (H2) and 95-102 (H3) in the heavy chain variable domain as described by Kabat et al., Sequences of Proteins of Immunological Interest, 5th Ed. Public Health Service, National Institutes of Health, Bethesda, Md. (1991)] and/or those residues from a hypervariable loop (i.e., residues 26-32 (L1), 50-52 (L2) and 91-96 (L3) in the light chain variable domain and 26-32 (H1), 53-55 (H2) and 96-101 (H3) in the heavy chain variable domain as described by [Chothia et al., J. Mol. Biol. 196: 901-917 (1987)].

The carboxy-terminal portion of each chain contains a constant region. Light chains have a single domain within the constant region. Thus, light chains have one variable region and one constant region domain. Heavy chains have several domains within the constant region. The heavy chains in IgG, IgA, and IgD antibodies have three constant region domains, which are designated CH1, CH2, and CH3, and the heavy chains in IgM and IgE antibodies have four constant region domains, CH1, CH2, CH3 and CH4. Thus, heavy chains have one variable region and three or four constant regions.

The heavy chains of immunoglobulins can also be divided into three functional regions: the Fd region (a fragment comprising VH and CH1, i.e., the two N-terminal domains of the heavy chain), the hinge region, and the Fc region (the "fragment crystallizable" region, derived from constant regions and formed after pepsin digestion). The Fd region in combination with the light chain forms an Fab (the "fragment antigen-binding"). Because an antigen will react stereochemically with the antigen-binding region at the amino terminus of each Fab the IgG molecule is divalent, i.e., it can bind to two antigen molecules. The Fc region contains the domains that interact with immunoglobulin receptors on cells and with the initial elements of the complement cascade. Thus, the Fc fragment is generally considered responsible for the effector functions of an immunoglobulin, such as complement fixation and binding to Fc receptors.

The term "monoclonal antibody" as used herein refers to an antibody obtained from a population of substantially homogeneous antibodies, i.e., the individual antibodies comprising the population are identical except for possible naturally occurring mutations or alternative post-translational modifications that may be present in minor amounts, whether produced from hybridomas or recombinant DNA techniques. Nonlimiting examples of monoclonal antibodies include murine, chimeric, humanized, or human antibodies, or variants or derivatives thereof.

Humanizing or modifying antibody sequence to be more human-like is described in, e.g., Jones et al., Nature 321:522 525 (1986); Morrison et al., Proc. Natl. Acad. Sci., U.S.A., 81:6851 6855 (1984); Morrison and Oi, Adv. Immunol., 44:65 92 (1988); Verhoeyer et al., Science 239:1534 1536 (1988); Padlan, Molec. Immun. 28:489 498-(1991); Padlan, Molec. Immunol. 31(3):169 217 (1994); and Kettleborough, C. A. et al., Protein Eng. 4(7):773 83 (1991); Co, M. S., et al. (1994), J. Immunol. 152, 2968-2976); Studnicka et al. Protein Engineering 7: 805-814 (1994); each of which is incorporated herein by reference.

One method for isolating human monoclonal antibodies is the use of phage display technology. Phage display is described in e.g., Dower et al., WO 91/17271, McCafferty et al., WO 92/01047, and Caton and Koprowski, Proc. Natl. Acad. Sci. USA, 87:6450-6454 (1990), each of which is incorporated herein by reference. Another method for isolating human monoclonal antibodies uses transgenic animals that have no endogenous immunoglobulin production and are engineered to contain human immunoglobulin loci. See, e.g., Jakobovits et al., Proc. Natl. Acad. Sci. USA, 90:2551 (1993); Jakobovits et al., Nature, 362:255-258 (1993); Bruggermann et al., Year in Immuno., 7:33 (1993); WO 91/10741, WO 96/34096, WO 98/24893, or U.S. patent application publication nos. 20030194404, 20030031667 or 20020199213; each incorporated herein by reference.

Antibody fragments may be produced by recombinant DNA techniques or by enzymatic or chemical cleavage of intact antibodies. "Antibody fragments" comprise a portion of an intact full length antibody, preferably the antigen binding or variable region of the intact antibody, and include multispecific (bispecific, trispecific, etc.) antibodies formed from antibody fragments. Nonlimiting examples of antibody fragments include Fab, Fab', F(ab')2, Fv [variable region], domain antibody (dAb) [Ward et al., Nature 341:544-546, 1989], complementarity determining region (CDR) fragments, single-chain antibodies (scFv) [Bird et al., Science 242:423-426, 1988, and Huston et al., Proc. Natl. Acad. Sci. USA 85:5879-5883, 1988, optionally including a polypeptide linker; and optionally multispecific, Gruber et al., J. Immunol. 152: 5368 (1994)], single chain antibody fragments, diabodies [EP 404,097; WO 93/11161; and Hollinger et al., Proc. Natl. Acad. Sci. USA, 90:6444-6448 (1993)], triabodies, tetrabodies, minibodies [Olafsen, et al., Protein Eng Des Sel. 2004 April; 17(4):315-23], linear antibodies [Zapata et al., Protein Eng., 8(10):1057-1062 (1995)]; chelating recombinant antibodies [Neri et al., J Mol Biol. 246:367-73, 1995], tribodies or bibodies [Schoonjans et al., J Immunol. 165:7050-57, 2000; Willems et al., J Chromatogr B Analyt Technol Biomed Life Sci. 786:161-76, 2003], intrabodies [Biocca, et al., EMBO J. 9:101-108, 1990; Colby et al., Proc Natl Acad Sci USA. 101:17616-21, 2004], nanobodies [Cortez-Retamozo et al., Cancer Research 64:2853-57, 2004], an antigen-binding-domain immunoglobulin fusion protein, a camelized antibody [Desmyter et al., J. Biol. Chem. 276:26285-90, 2001; Ewert et al., Biochemistry 41:3628-36, 2002; U.S. Patent Publication Nos. 20050136049 and 20050037421], a VHH containing antibody, mimetibodies [U.S. Patent Publication Nos. 20050095700 and 20060127404; WO 04/002424 A2; WO 05/081687 A2], or variants or derivatives thereof, and polypeptides that contain at least a portion of an immunoglobulin that is sufficient to confer specific antigen binding to the polypeptide, such as a CDR sequence, as long as the antibody retains the desired antigen-binding activity.

The term "variant" when used in connection with antibodies refers to polypeptide sequence of an antibody that contains at least one amino acid substitution, deletion, or insertion in the variable region or the portion equivalent to the variable region, provided that the variant retains the desired target binding affinity or biological activity. In addition, the antibodies of the invention may have amino acid modifications in the constant region to modify effector function of the antibody, including half-life or clearance, ADCC and/or CDC activity. Such modifications can enhance pharmacokinetics or enhance the effectiveness of the antibody in treating cancer, for example. In the case of IgG1, modifications to the constant region, particularly the hinge or CH2 region, may increase or decrease effector function, including ADCC and/or CDC activity. In other embodiments, an IgG2 constant region is modified to decrease antibody-antigen aggregate formation. In the case of IgG4, modifications to the constant region, particularly the hinge region, may reduce the formation of half-antibodies.

The term "derivative" when used in connection with antibodies refers to antibodies covalently modified by conjugation to therapeutic or diagnostic agents, labeling (e.g., with radionuclides or various enzymes), covalent polymer attachment such as pegylation (derivatization with polyethylene glycol) and insertion or substitution by chemical synthesis of non-natural amino acids. Derivatives of the invention will retain the binding properties of underivatized molecules of the invention. Conjugation of cancer-targeting antibodies to cytotoxic agent, for example, radioactive isotopes (e.g., I131, I125, Y90 and Re186), chemotherapeutic agents, or toxins, may enhance destruction of cancerous cells.

An immunoglycoprotein that is "specific" for a target molecule binds to that target with a greater affinity than any other target. Immunoglycoproteins of the invention may have affinities for their targets of a Ka of at least about $10^4$ $M^{-1}$, or alternatively of at least about $10^5$ $M^{-1}$, $10^6$ $M^{-1}$, $10^7$ $M^{-1}$, $10^8$ $M^{-1}$, $10^9$ $M^{-1}$, or $10^{10}$ $M^{-1}$. Such affinities may be readily determined using conventional techniques, such as by using a BIAcore instrument or by radioimmunoassay using radiolabeled target antigen. Affinity data may be analyzed, for example, by the method of Scatchard et al., Ann N.Y. Acad. Sci., 51:660 (1949).

Carbohydrate Modifiers

A "carbohydrate modifier" is a small organic compound, preferably of molecular weight <1000 daltons, that inhibits the activity of an enzyme involved in the addition, removal, or modification of sugars that are part of a carbohydrate attached to a polypeptide. Glycosylation is an extremely complex process that takes place in the endoplasmic reticulum ("core glycosylation") and in the Golgi bodies ("terminal glycosylation").

Other polypeptide-based or polynucleotide-based repressors of glycosylation enzymes, including RNAi or antisense that inhibits activity of early stage carbohydrate modifiers, are useful according to the invention but are excluded from the definition of "carbohydrate modifier."

As used herein, "early stage carbohydrate modifier" refers to an inhibitor of one or more of the glycosylation steps prior to addition of N-acetylglucosamine to mannose, including ER glucosidase I, ER glucosidase II, ER mannosidase, Golgi mannosidase IA, Golgi mannosidase IB, Golgi mannosidase IC and GlcNAc-transferase I.

Subsequent glycosylation steps include Golgi mannosidase II, GlcNAc-transferase II, galactosyl transferase and sialyl transferase, fucosyl transferase, and fucokinase.

Exemplary carbohydrate modifiers include any of the following. Castanospermine is believed to be a glucosidase I and II inhibitor. Deoxyfuconojirimycin is a fucosidase inhibitor. 6-Methyl-tetrahydro-pyran-2H-2,3,4-triol has been reported in vitro to inhibit phosphorylation of L-fucose, the first step in biosynthesis of GDP-L-Fucose. 6,8a-diepicastanospermine is a reported fucosyltransferase inhibitor. 1-N-iminosugars A and B (also known as 1-Butyl-5-methyl-piperidine-3,4-diol hydrochloride and 5-Methyl-piperidine-3,4-diol hydrochloride, respectively) have been reported to be fucosyltransferase inhibitors. Deoxymannojirimycin (DMJ) is an ER mannosidase I inhibitor. Kifunensine (Kf) is an ER mannosidase I inhibitor. Swainsonine (Sw) is a golgi mannosidase II inhibitor. Monensin (Mn) is an inhibitor of intracellular protein transport between ER and Golgi that interferes with elongation of core oligosaccharide.

Data described herein show that a variety of glycosidase and/or mannosidase inhibitors provide one or more of desired effects of increasing ADCC activity, increasing Fc receptor binding, and altering glycosylation pattern.

In exemplary embodiments, castanospermine (MW 189.21) is added to the culture medium to a final concentration of about 200 µM (corresponding to about 37.8 µg/mL), or concentration ranges greater than about 10, 20, 30, 40, 50, 60, 70, 80, 90, 100, 110, 120, 130, 140, or 150 µM, and up to about 300, 275, 250, 225, 200, 175, 150, 125, 100, 75, 60, or 50 µg/mL. For example, ranges of 10-50, or 50-200, or 50-300, or 100-300, or 150-250 µM are contemplated.

In other exemplary embodiments, DMJ, for example DMJ-HCl (MW 199.6) is added to the culture medium to a final concentration of about 200 µM (corresponding to about 32.6 µg DMJ/mL), or concentration ranges greater than about 10, 20, 30, 40, 50, 60, 70, 80, 90, 100, 110, 120, 130, 140, or 150 µM, and up to about 300, 275, 250, 225, 200, 175, 150, 125, 100, 75, 60, or 50 µg/mL. For example, ranges of 10-50, or 50-200, or 50-300, or 100-300, or 150-250 µM are contemplated.

In other exemplary embodiments, kifunensine (MW 232.2) is added to the culture medium to a final concentration of about 10 µM (corresponding to about 2.3 µg/mL), or concentration ranges greater than about 0.5, 1, 2, 3, 4, 5, 6, 7, 8, 9 or 10 µM, and up to about 50, 45, 40, 35, 30, 25, 20, 19, 18, 17, 16, 15, 14, 13, 12, or 11 µM. For example, ranges of 1-10, or 1-25, or 1-50, or 5-10, or 5-25, or 5-15 µM are contemplated.

Recombinant Constructs, Cells and Culturing Methods

As used herein, "host cell" specifically excludes rodent hybridomas but includes any other cell that is capable of glycosylation (i.e. addition of carbohydrate to an amino acid of a polypeptide) and that has been modified through recombinant means to express increased levels of a protein product. Progeny of host cells that retain the recombinant modification and the ability to express the protein product are included within the term "host cell".

Exemplary elements of expression vectors or regulatory sequences may include an origin of replication, a promoter, an operator, or other elements that mediate transcription and translation. Promoters can be constitutive or active and may further be cell type specific, tissue specific, individual cell specific, event specific, temporally specific or inducible. Event specific promoters are active or up regulated only upon the occurrence of an event. In addition to the promoter, repressor sequences, negative regulators, or tissue-specific silencers may be inserted to reduce non-specific expression. Other elements include internal ribosome binding sites, a transcription terminator sequence, including a polyadenylation sequence, splice donor and acceptor sites, and an enhancer, a selectable marker and the like.

The culture medium can include any necessary or desirable ingredients known in the art, such as carbohydrates, including glucose, essential and/or non-essential amino acids, lipids and lipid precursors, nucleic acid precursors, vitamins, inorganic salts, trace elements including rare metals, and/or cell growth factors. The culture medium may be chemically defined or may include serum, plant hydrolysates, or other derived substances. The culture medium may be essentially or entirely serum-free or animal-component free. "Essentially serum-free" means that the medium lacks any serum or contains an insignificant amount of serum. Exemplary supplementary amino acids depleted during cell culture include asparagine, aspartic acid, cysteine, cystine, isoleucine, leucine, tryptophan, and valine.

Commercially available lipids and/or lipid precursors include choline, ethanolamine, or phosphoethanolamine, cholesterol, fatty acids such as oleic acid, linoleic acid, linolenic acid, methyl esters, D-alpha-tocopherol, e.g. in acetate form, stearic acid; myristic acid, palmitic acid, palmitoleic acid; or arachidonic acid. Essential amino acids include Arginine, Histidine, Isoleucine, Leucine, Lysine, Methionine, Phenylalanine, Threonine, Tryptophan and Valine. Non-essential amino acids include Alanine, Asparagine, Aspartate, Cysteine, Glutamate, Glutamine, Glycine, Proline, Serine, and Tyrosine. Commercially available inorganic or trace elements, supplied as appropriate salts, include sodium, calcium, potassium, magnesium, copper, iron, zinc, selenium, molybdenum, vanadium, manganese, nickel, silicon, tin, aluminum, barium, cadmium, chromium, cobalt, germanium, potassium, silver, rubidium, zirconium, fluoride, bromide, iodide and chloride. The medium may also optionally include a nonionic surfactant or surface-active agent to protect the cells from the mixing or aeration. The culture medium may also comprise buffers such as sodium bicarbonate, monobasic and dibasic phosphates, HEPES and/or Tris. The culture medium may also comprise inducers of protein production, such as sodium butyrate, or caffeine.

The invention also provides methods for producing an immunoglycoprotein comprising culturing a host cell in any of the culture media or under any of the conditions described herein. Such methods may further include the step of recovering the immunoglycoprotein from the host cells or culture medium. The carbohydrate modifier may be included in the initial culture medium, or may be added during the initial growth phase or at later phases. When the recombinant protein is secreted into the medium, the medium can be harvested periodically and replaced with fresh medium through several harvest cycles.

Although CHO cells, which are widely used for therapeutic protein production, are preferred, any host cells known in the art to produce glycosylated proteins may be used, including yeast cells, plant cells, plants, insect cells, and mammalian cells. Exemplary yeast cells include *Pichia*, e.g. *P. pastoris*, and *Saccharomyces* e.g. *S. cerevisiae*, as well as *Schizosaccharomyces pombe, Kluyveromyces, K. Zactis, K. fragilis, K. bulgaricus, K. wickeramii, K. waltii, K. drosophilarum, K. themotolerans*, and *K. marxianus; K. yarrowia; Trichoderma*

*reesia, Neurospora crassa, Schwanniomyces, Schwanniomyces occidentalis, Neurospora, Penicillium, Totypocladium, Aspergillus, A. nidulans, A. niger, Hansenula, Candida, Kloeckera, Torulopsis,* and *Rhodotorula*. Exemplary insect cells include *Autographa californica* and *Spodoptera frugiperda*, and *Drosophila*. Exemplary mammalian cells include varieties of CHO, BHK, HEK-293, NS0, YB2/3, SP2/0, and human cells such as PER-C6 or HT1080, as well as VERO, HeLa, COS, MDCK, NIH3T3, Jurkat, Saos, PC-12, HCT 116, L929, Ltk-, WI38, CV1, TM4, W138, Hep G2, MMT, a leukemic cell line, embryonic stem cell or fertilized egg cell.

The cells may be cultured in any culture system and according to any method known in the art, including T-flasks, spinner and shaker flasks, roller bottles and stirred-tank bioreactors. Anchorage-dependent cells can also be cultivated on microcarrier, e.g. polymeric spheres, that are maintained in suspension in stirred-tank bioreactors. Alternatively, cells can be grown in single-cell suspension. Culture medium may be added in a batch process, e.g. where culture medium is added once to the cells in a single batch, or in a fed batch process in which small batches of culture medium are periodically added. Medium can be harvested at the end of culture or several times during culture. Continuously perfused production processes are also known in the art, and involve continuous feeding of fresh medium into the culture, while the same volume is continuously withdrawn from the reactor. Perfused cultures generally achieve higher cell densities than batch cultures and can be maintained for weeks or months with repeated harvests.

Determination of Oligosaccharide Characteristics

Oligosaccharide content and characteristics of the immunoglycoprotein compositions of the invention can be determined using means known in the art. For example, oligosaccharides can be released from the immunoglycoprotein by enzymatic digestion with PNGase-F under denaturing conditions. The oligosaccharides can then be derivatized with a fluorescent modifier and resolved by normal phase chromatography coupled with fluorescence detection. Major species can be analyzed by MALDI-TOF.

The presence of N-linked glycosylation sites that are available for linkage of oligosaccharides can be determined by methods known in the art. For example, mass differences between glycosylated immunoglycoprotein and unglycosylated recombinant immunoglycoprotein (e.g., expressed recombinantly in a bacterial cell that does not glycosylate protein) provides information on the total mass of saccharide added via glycosylation. Individual mutation of theoretical N-linked glycosylation sites (the tripeptide consensus motif Asn-X-Thr/Ser) to destroy the motif, followed by comparison of the mass of the nonmutated immunoglycoprotein to the mutated immunoglycoprotein, can provide information on whether the site is available for glycosylation. If the hypothetical site is a potential N-linked glycosylation site, destruction of the motif should yield a reduction in the carbohydrate content of the immunoglycoprotein.

Monosaccharide composition analysis can be carried out generally as follows. Monosaccharides are released by acid hydrolysis, then derivitized with a fluorescent modifier and resolved by reverse phase chromatography coupled with fluorescence detection, and quantified using labeled monosaccharide standards. Results can be expressed as the mole ratio of each monosaccharide to protein. From this information, the ratio of saccharide to N-glycosylation site can be calculated.

Immunoglycoproteins contain sufficient amino acid sequence derived from a constant region of an immunoglobulin to provide an effector function, preferably ADCC and/ or CDC. This amino acid sequence derived from the constant region comprises an N-linked glycosylation site at the position corresponding to Asn297, using Kabat numbering. Thus, exemplary molecules will contain a sequence derived from a CH2 domain of an immunoglobulin that includes the Asn297.

Oligosaccharide characteristics of a particular N-linked glycosylation site can be determined by producing a fragment containing that N-linked glycosylation site via enzymatic digestion, and analyzing the oligosaccharide content of the fragment. For example, the ratio of oligosaccharide or monosaccharide from a CH2-derived domain to N-linked glycosylation site(s) in this same CH2-derived domain can be determined as follows. Proteolytic fragments of the immunoglycoprotein can be produced by enzymatic digestion. Subsequent LCMS analysis of the resolved peptides (MS analysis of peptide map), with comparison to the peptide map of a deglycosylated molecule, will provide identification of the specific peptides which contain the glycosylation site. The glycan content at each N-linked site can then be deduced by glycoprofiling, in which the known peptide mass is subtracted from the determined glycopeptide mass and the result analyzed by comparison to the mass of known glycan structures. In addition, specific regions (e.g., in the case of multiple glycosylation sites) of the intact molecule can be separated by enzymatic digest then resolved and collected by HPLC. These individual sites can then be analyzed for glycan content by MS, monosaccharide analysis and oligosaccharide analysis.

In addition, specific monosaccharide branching or content can be determined as follows. Mono or oligosaccharides can be released using specific enzymes that only recognize certain sugars or branching patterns. The sugars released can be labeled and resolved.

LCMS Glycoprofiling can be carried out as generally follows. Glycoprofiling from the single N-linked glycosylation site can be performed by comparison of native vs. de-glycosylated sample in both whole mass and glycopeptide LCMS analysis. Samples are reduced to the monomeric form and analyzed by ESI-TOF. GlycoMod can be used to identify the glycan species.

Use of Immunoglycoproteins

The immunoglycoproteins of the invention are useful as therapeutics to treat diseases mediated by the target molecule, or, for example, as cytolytic agents to kill cancer cells that have the target molecule expressed or associated with the cell surface.

"Treatment" or "treating" refers to either a therapeutic treatment or prophylactic or preventative treatments. A therapeutic treatment may improve at least one symptom of disease in an individual receiving treatment or may delay worsening of a progressive disease in an individual, or prevent onset of additional associated diseases. An improved response is assessed by evaluation of clinical criteria well-known in the art for the disease state.

A "therapeutically effective dose" or "effective dose" of an immunoglycoprotein refers to that amount of the compound sufficient to result in amelioration of one or more symptoms of the disease being treated. When applied to an individual active ingredient, administered alone, a therapeutically effective dose refers to that ingredient alone. When applied to a combination, a therapeutically effective dose refers to combined amounts of the active ingredients that result in the therapeutic effect, whether administered in combination, serially or simultaneously. The doses may be administered based on weight of the patient, e.g., at a dose of 0.01 to 50 mg/kg, and may be administered on a daily or weekly basis, or every 2 weeks, every 3 weeks, or once a month.

To administer the immunoglycoproteins of the invention to humans or test animals, it is preferable to formulate the molecule in a composition comprising one or more pharmaceutically acceptable carriers or diluents, preferably sterile carriers or diluents if the composition is for parenteral administration. The phrase "pharmaceutically or pharmacologically acceptable" refer to molecular entities and compositions that do not produce allergic, or other adverse reactions when administered using routes well-known in the art, as described below. "Pharmaceutically acceptable carriers" include any and all clinically useful solvents, dispersion media, coatings, antibacterial and antifungal agents, isotonic and absorption delaying agents and the like. Generally, compositions are also essentially free of pyrogens, as well as other impurities that could be harmful to the recipient.

Immunoglycoproteins may be administered orally, topically, transdermally, parenterally, by inhalation spray, vaginally, rectally, or by intracranial injection. The term parenteral as used herein includes subcutaneous injections, intravenous, intramuscular, intracisternal injection, or infusion techniques. Administration by intravenous, intradermal, intramusclar, intramammary, intraperitoneal, intrathecal, retrobulbar, intrapulmonary injection and or surgical implantation at a particular site is contemplated as well.

In one embodiment, administration is performed at the site of a cancer or affected tissue needing treatment by direct injection into the site or via a sustained delivery or sustained release mechanism, which can deliver the formulation internally. For example, biodegradable microspheres or capsules or other biodegradable polymer configurations capable of sustained delivery of a composition (e.g., a soluble polypeptide, antibody, or small molecule) can be included in the formulations of the invention implanted near the cancer Therapeutic compositions may also be delivered to the patient at multiple sites. The multiple administrations may be rendered simultaneously or may be administered over a continuous period of time.

Injection of aqueous solutions are preferred. Aqueous compositions can be lyophilized for storage and reconstituted in a suitable carrier prior to use. This technique has been shown to be effective with conventional immunoglobulins. Any suitable lyophilization and reconstitution techniques can be employed. It will be appreciated by those skilled in the art that lyophilization and reconstitution can lead to varying degrees of activity loss and that use levels may have to be adjusted to compensate.

In all cases the form must be sterile and must be fluid to the extent that easy syringability exists. The proper fluidity can be maintained, for example, by the use of a coating, such as lecithin, by the maintenance of the required particle size in the case of dispersion and by the use of surfactants. It must be stable under the conditions of manufacture and storage and may be preserved against the contaminating action of microorganisms, such as bacteria and fungi. The prevention of the action of microorganisms can be brought about by various antibacterial and antifungal agents, for example, parabens, chlorobutanol, phenol, sorbic acid, thimerosal, and the like. In many cases, it will be desirable to include isotonic agents, for example, sugars or sodium chloride.

In addition, the properties of hydrophilicity and hydrophobicity of the compositions contemplated for use in the invention are well balanced, thereby enhancing their utility for both in vitro and especially in vivo uses, while other compositions lacking such balance are of substantially less utility. Specifically, compositions contemplated for use in the invention have an appropriate degree of solubility in aqueous media which permits absorption and bioavailability in the body, while also having a degree of solubility in lipids which permits the compounds to traverse the cell membrane to a putative site of action.

Also contemplated in the present invention is the administration of an immunoglycoprotein composition in conjunction with a second agent.

As an additional aspect, the invention includes kits or articles of manufacture which comprise one or more compounds or compositions packaged in a manner which facilitates their use to practice methods of the invention. In one embodiment, such a kit includes a immunoglycoprotein described herein, optionally with a second therapeutic agent, packaged in a container such as a sealed bottle or vessel, with a label affixed to the container or included in the package that describes use of the compound or composition in practicing the method. Preferably, the compound or composition is packaged in a unit dosage form. The kit may further include a device suitable for administering the composition according to a specific route of administration or for practicing a screening assay. Preferably, the kit contains a label that describes use of the composition.

The invention further contemplates the use of the immunoglycoproteins of the invention in the manufacture of a medicament for the inhibition or prevention or treatment of a disease, condition, or disorder in a subject characterized or mediated by the target to which the immunoglycoprotein binds.

BRIEF DESCRIPTION OF THE DRAWINGS

FIG. 21 depicts the results of an assay for simultaneous binding of CHO-K1 produced TRU-016 and CS-generated glycovariants thereof to CD37 and FcγRIIIa (CD16). Concentrations of CS utilized for generation of the tested glycovariants are as indicated. Results are depicted as both the raw curve data (A) as well as in a bar graph form that indicates the maximal geometric mean fluorescence intensity achieved by each glycovariant and the TRU-016 control (B).

FIG. 24 depicts an assay for simultaneous binding of DG44 CHO produced TRU-016 and CS-generated glycovariants thereof to CD37 and FcγRIIIa (CD16). These samples represented PA samples purified from bioreactor runs. Concentrations of CS utilized for generation of the tested glycovariants are as indicated. Results are depicted as both the raw curve data (A) as well as in a bar graph form that indicates the maximal geometric mean fluorescence intensity achieved by each glycovariant and the TRU-016 control (B).

FIG. 26 depicts results obtained from LCMS tryptic digest glycoprofiling of TRU-016 and CS-generated glycovariants thereof. The top frame shows that section of the chromatograms in which the glycopeptides elute and includes all detected peaks. The bottom frame is the same data, but shows only those peaks which correspond to the mass of the glycopeptide.

DETAILED DESCRIPTION OF THE INVENTION

Examples

Example 1

Production of SMIP Products

TRU-016

Figure 1:
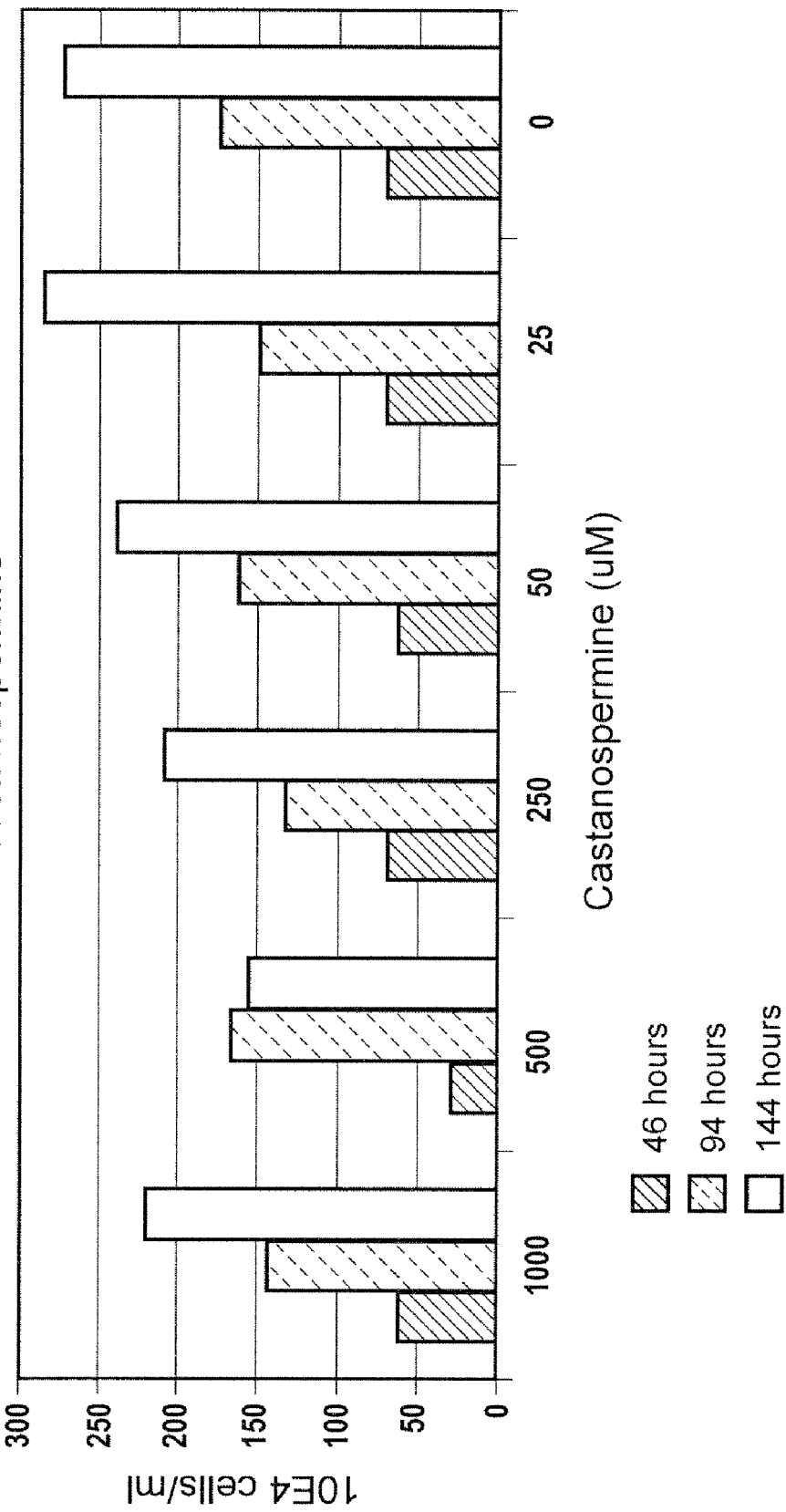
FIG. 1 depicts cell growth of CHO cells expressing TRU-016 grown in cell media with various concentrations of castanospermine, as shown by cell counts of cells/ml.

CD37-specific SMIPs are described in co-owned U.S. application Ser. No. 10/627,556 and U.S. Patent Publication Nos. 2003/133939, 2003/0118592 and 2005/0136049, each incorporated by reference herein in its entirety. An exemplary SMIP, TRU-016, is produced as described below. As used herein, TRU-016 refers to any CD37-specific SMIP.

TRU-016 [G28-1 scFv VH11S (SSC-P)H WCH2 WCH3] is a recombinant single chain protein that binds to the CD37 antigen. The nucleotide and amino acid sequences of TRU-016 are respectively set out in SEQ ID NOS: 1 and 2. Additional sequences are set forth in co-owned, concurrently filed U.S. patent application Ser. No. 12/437,507 [Entitled "B-CELL REDUCTION USING CD37-SPECIFIC AND CD20-SPECIFIC BINDING MOLECULES", hereby incorporated by reference in its entirety. The binding domain was based on the G28-1 antibody sequence previously disclosed in the patent publications listed in the preceding paragraph, which disclosure is incorporated herein by reference. The binding domain is connected to the effector domain, the CH2 and CH3 domains of human IgG1, through a modified hinge region. This TRU-016 exists as a dimer in solution.

TRU-016 is produced by recombinant DNA technology in a Chinese hamster ovary (CHO) mammalian cell expression system. TRU-016 SMIPs are purified from CHO culture supernatants by Protein A affinity chromatography. Using dPBS, a 50 mL rProtein A FF sepharose column (GE Healthcare rProtein A Sepharose FF, Catalog #17-0974-04) is equilibrated at 5.0 mls/min (150 cm/hr) for 1.5 column volumes (CV). The culture supernatant is loaded to the rProtein A Sepharose FF column at a flow rate of 1.7 mls/min using the AKTA Explorer 100 Air (GE healthcare AKTA Explorer 100 Air, Catalog #18-1403-00), capturing the recombinant TRU-016. The column is washed with dPBS for 5 Column Volumes (CV), then 1.0 M NaCl, 20 mM Sodium Phosphate, pH 6.0, and then with 25 mM NaCl, 25 mM NaOAc, pH 5.0. These washing steps remove nonspecifically bound CHO host cell proteins from the rProtein A column that contribute to product precipitation after elution.

The recombinant TRU-016 is eluted from the column with 100 mM Glycine, pH 3.5. 10 mL fractions of the eluted product were recovered and the eluted product was then brought to pH 5.0 with 20% of the eluted volume of 0.5 M 2-(N-Morpholino)ethanesulfonic acid (MES) pH 6.0. This eluted product is concentrated to approximately 25 mg/mL TRU-016 and filter sterilized.

Purified protein is then subjected to GPC size exclusion chromatography (SEC) to achieve further purification of the TRU-016 (dimer) molecule from higher molecular weight aggregates. Using dPBS, an XK 50/100 column (GE healthcare XK 50/100 empty chromatography column, Catalog #18-8753-01) containing 1 L of Superdex 200 FF sepharose is equilibrated at 12.6 mls/min (38 cm/hr) for 1.5 column volumes (CV). A maximum volume of 54 mls (3% CV) of sample is applied to the column. The column continues to run at 12.6 ml/min and the eluted protein is fractionated in 40 mL fractions. Each fraction is analyzed for product quality using an analytic HPLC, and the eluted fractions are pooled for >95% POI (non-aggregated) TRU-016. This resultant pool is filter sterilized at 0.22 µm. The material is then concentrated and formulated with 20 mM sodium phosphate and 240 mM sucrose, at pH 6.0.

An alternative method for purification of the glycovariant is as follows. TRU-016 SMIPS are purified from CHO culture supernatants by Protein A affinity chromatography. Using dPBS, a 1 mL MabSelect affinity chromatography column (GE Healthcare Hitrap MabSelect, catalog #28-4082-53) is equilibrated at 1.0 mL/min for 7 column volumes (CV). The culture supernatant is loaded on to the MabSelect column at a flowrate of 1.0 mL/min using the Akta Explorer 100 Air (GE Healthcare, Akta Explorer 100 Air, catalog #18-1403-00) capturing the recombinant TRU-016. The column is washed with dPBS for 20 CV, then with 20 mM Sodium Phosphate, 1.0 M NaCl, pH 7.0 for 5 CV and then with dPBS for 3 CV.

The recombinant TRU-016 is eluted from the column with 10 mM Citrate, pH 3.5 and the column is stripped with 10 mM Citrate 3.0 for 8 CV. Following the strip the column is re-equilibrated for 5 CV with dPBS. The protein is collected into fractions during elution which are pooled based upon absorbance and this pooled material is brought to pH 5.0 with an addition of approximately 400 µL of 0.55 M 2-(N-Morpholin) ethanesulfonic acid (MES) pH 6.0 per 5 mL of elution. This neutralized eluate is filter sterilized and stored at 2-8° C. The samples from this purification method are referred to as PA samples.

Experiments may be performed to confirm that the binding specificity of the parent antibody to the CD37 cell surface receptor is preserved in TRU-016. Human PBMCs are isolated over LSM density gradients and incubated with unconjugated TRU-016 and PE-conjugated anti-human CD19. Cells are washed and incubated with 1:100 FITC GAH IgG (Fc specific) for 45 minutes on ice. Cells are washed and analyzed by two-color flow cytometry on a FACsCalibur instrument using Cell Quest software. Cells are gated for B lymphocytes or non-B lymphocytes by CD19 staining.

With increasing concentrations of TRU-016, the FITC signal on the B lymphocyte (CD19 positive gate) increases rapidly from 0.01-1.0 µg/ml, until reaching saturation at approximately 1 µg/mL or a mean fluorescence intensity (MFI) of 1000. In contrast, the staining of the non-B lymphocyte population is detectable, but very low, and increases slowly with increasing concentration of scFvIg.

TRU-015

CD20-specific SMIPs are prepared similarly. CD20-specific SMIPs are described in co-owned US Patent Publications 2003/133939, 2003/0118592 and 2005/0136049, each incorporated by reference herein in its entirety. An exemplary SMIP, TRU-015, is described below.

TRU-015 is a recombinant single chain protein that binds to the CD20 antigen. The nucleotide and amino acid sequences of TRU-015 are respectively set out in SEQ ID NOS: 3 and 4. The binding domain was based on a publicly available human CD20 antibody sequence. The binding domain is connected to the effector domain, the CH2 and CH3 domains of human IgG1, through a modified CSS hinge region. TRU-015 exists as a dimer in solution.

TRU-015 comprises the 2e12 leader peptide cloning sequence from amino acids 1-23 of SEQ ID NO: 4; the 2H7 murine anti-human CD20 light chain variable region with a lysine to serine (VHL11S) amino acid substitution at residue 11 in the variable region, which is reflected at position 34 in SEQ ID NO: 4; an asp-gly$_3$-ser-(gly$_4$ser)$_2$ linker, beginning at residue 129 in SEQ ID NO: 4; the 2H7 murine anti-human CD20 heavy chain variable region, which lacks a serine residue at the end of the heavy chain region, i.e., changed from VTVSS to VTVS; a human IgG1 Fc domain, including a modified hinge region comprising a (CSS) sequence, and wild type CH2 and CH3 domains.

Example 2

Culturing Host Cells with Carbohydrate Modifier

CHO cells transfected with TRU-016 or TRU-015 cDNA were cultured in shake flasks or wave bags with varying concentrations of various carbohydrate modifiers generally according to the procedures described below.

For shake flask runs, log phase host cells were seeded in shake flasks at 100,000 cells/ml with carbohydrate modifier at the concentration to be tested, and optionally with methotrexate (MTX) @ 50 nM.

Cells were seeded at 3×10$^6$/mL in 1350 mL of Ex-Cell 302 culture media (SATC Biosciences; with added non-essential amino acids, pyrucate, L-glutamine, pen/strep, HT Supplement and insulin, all from Invitrogen) at t=0 and brought to 5 L total volume at T>=72 hours. The cells were incubated at 37° C. and 5% carbon dioxide and monitored for growth and viability daily starting at day 6-7. Supernatants were typically harvested at day 10-12 when cell viability dropped below 60%.

Na-Azide was added to 0.02%, cells were removed by centrifugation and supernatant was filter sterilized through a 0.22 uM filter. Some assays described in other examples herein were performed on the supernatants as indicated, while other assays were performed on material that underwent further protein A purification. For wave bag runs, log phase host cells were seeded into 5 L wave bags at 100,000-200,000 cells/ml in 10-20% conditioned Ex-Cell 302 media (SATC Biosciences; with added non-essential amino acids, pyrucate, L-glutamine, pen/strep, HT Supplement and insulin, all from Invitrogen) with carbohydrate modifier at the concentration to be tested. Cells were incubated at 37° C. and 5% carbon dioxide and monitored daily for growth and viability. Supernatants were typically harvested at day 11-12 or when cell viability dropped below 50%.

Cells were removed by centrifugation in a Sorvall Legend at 3000 rpm (1932 rcf) for 20 minutes, the supernatant was filter sterilized. Some assays described in other examples herein were performed on the supernatants as indicated, while other assays were performed on material that underwent further protein A purification.

TRU-016 produced by cells cultured with varying concentrations of various carbohydrate modifiers is assayed for CD16 binding, ADCC, CDC, pharmacokinetic parameters and in vivo activity as described below.

Figure 2:
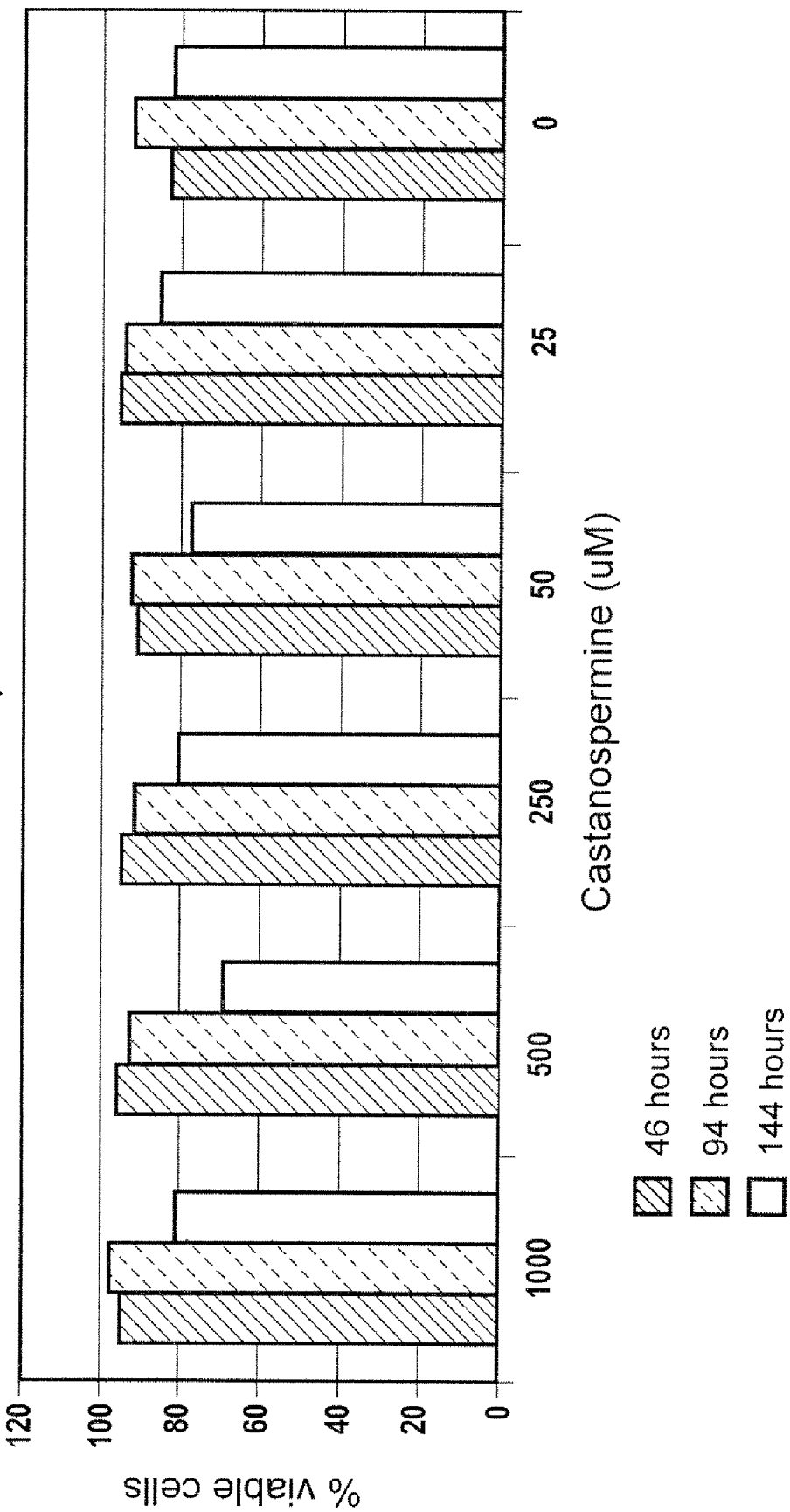
FIG. 2 depicts cell viability of CHO cells expressing TRU-016 grown in cell media with various concentrations of castanospermine, as shown by % of live cells.
Figure 3:
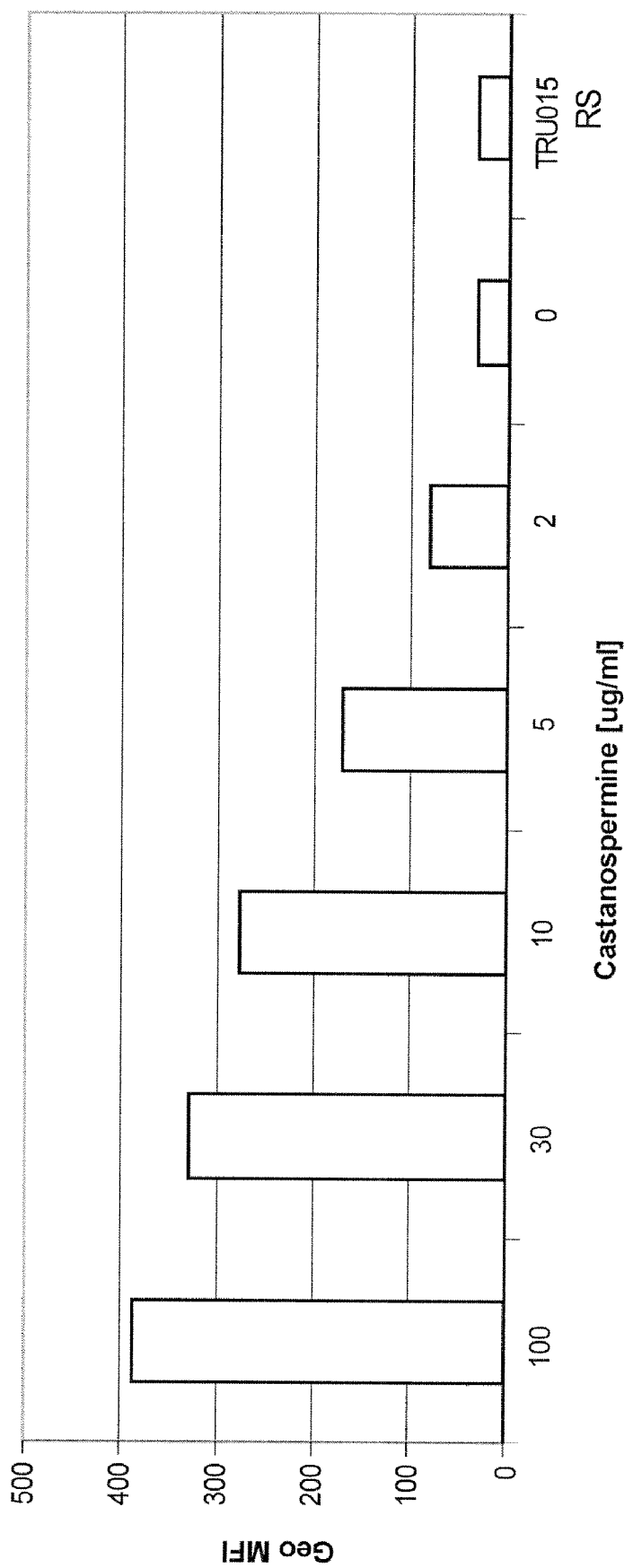
FIG. 3 depicts CD16 binding of TRU-015 produced by cells cultured in the presence of varying concentrations of castanospermine and shows geometric mean fluorescent intensity vs. castanospermine concentration.
Figure 4:
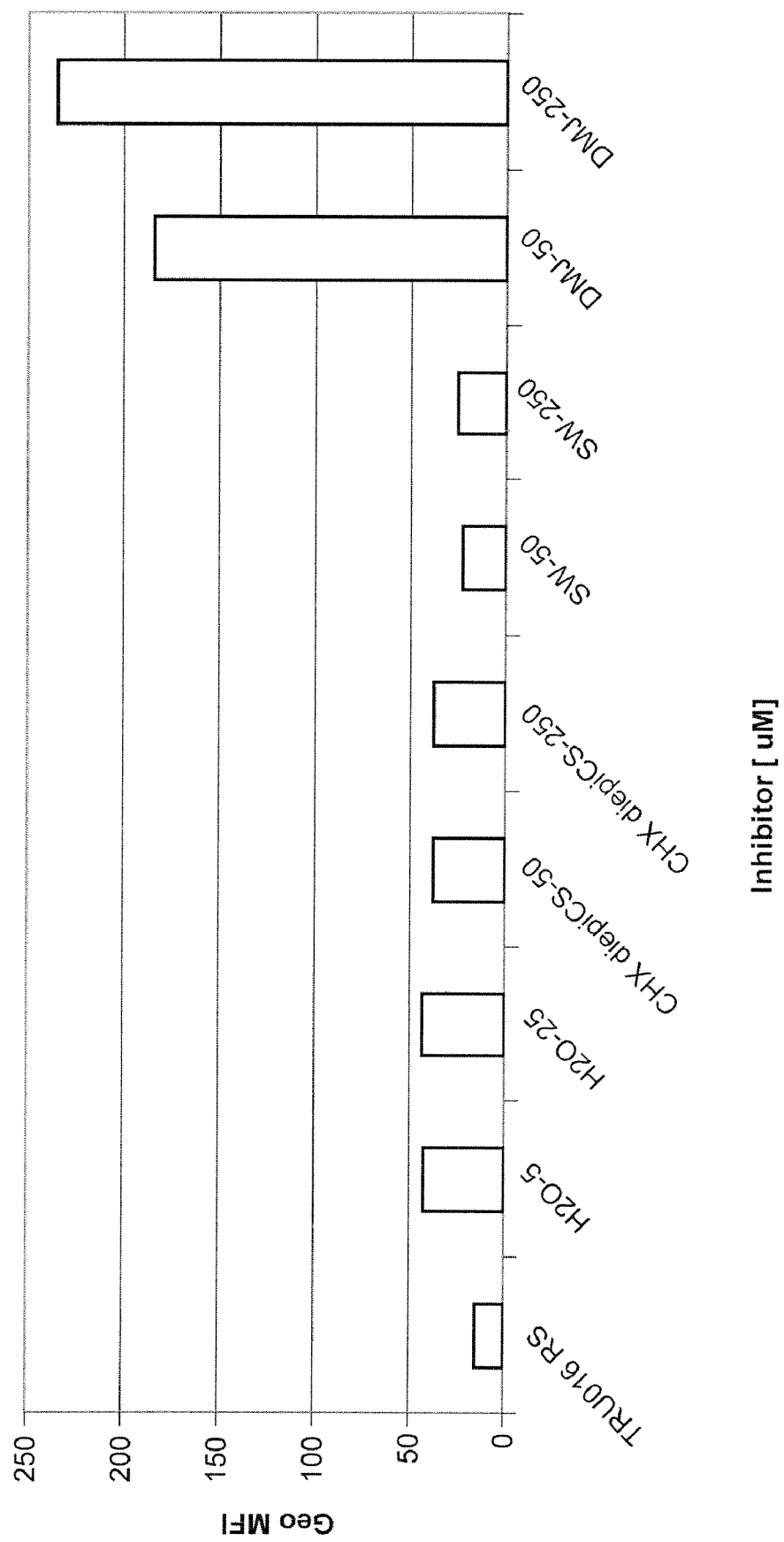
FIG. 4 depicts CD16 binding, as shown by geometric mean fluorescent intensity, of TRU-016 produced by cells cultured in the presence of various concentrations of 6,8a-diepi-castanospermine, swainsonine, or deoxymannojirimycin (DMJ).
Figure 5:
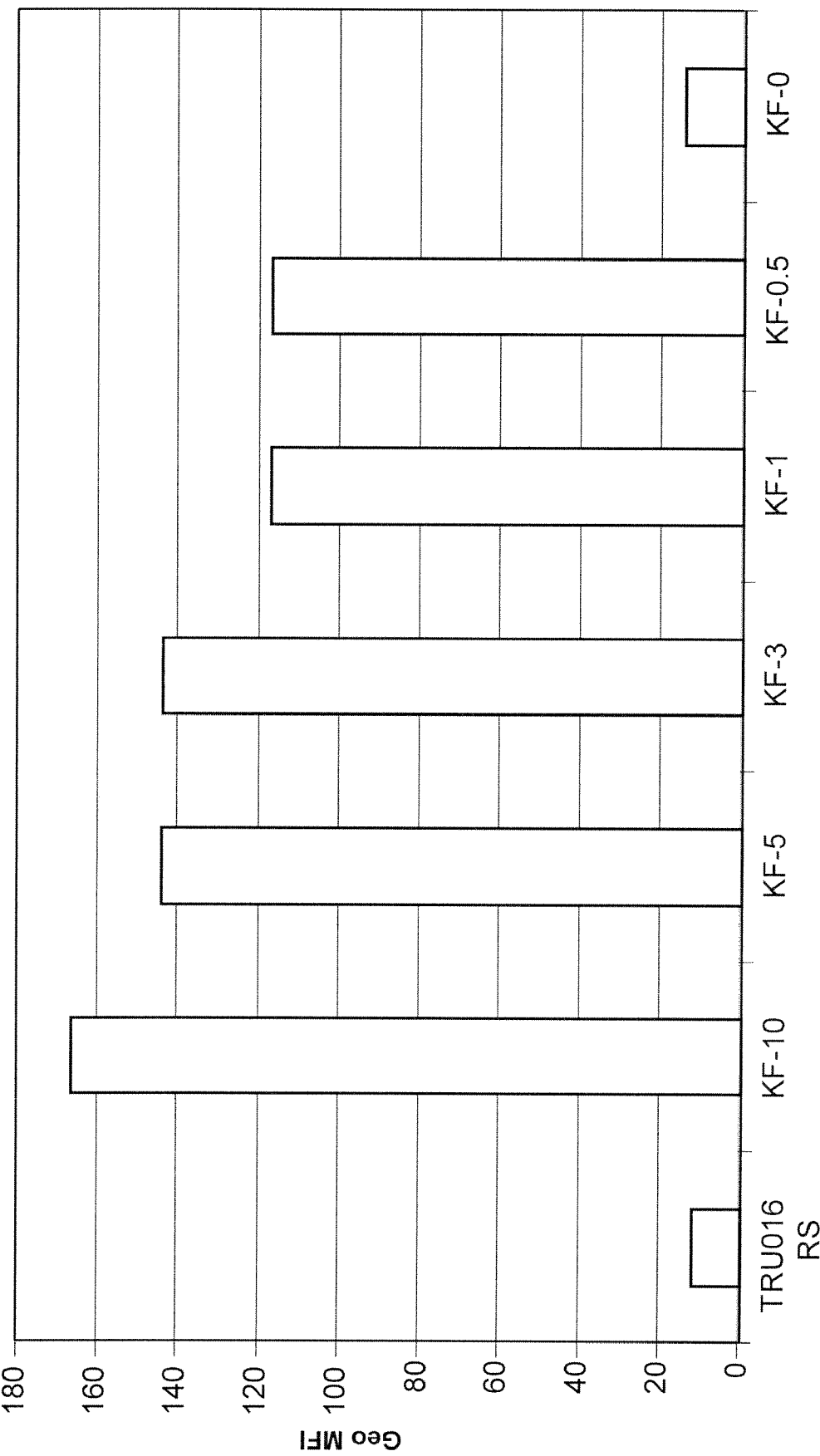
FIG. 5 depicts CD16 binding, as shown by mean fluorescent intensity, of TRU-016 produced by cells cultured in the presence of varying concentrations of kifunensine.
Figure 6:
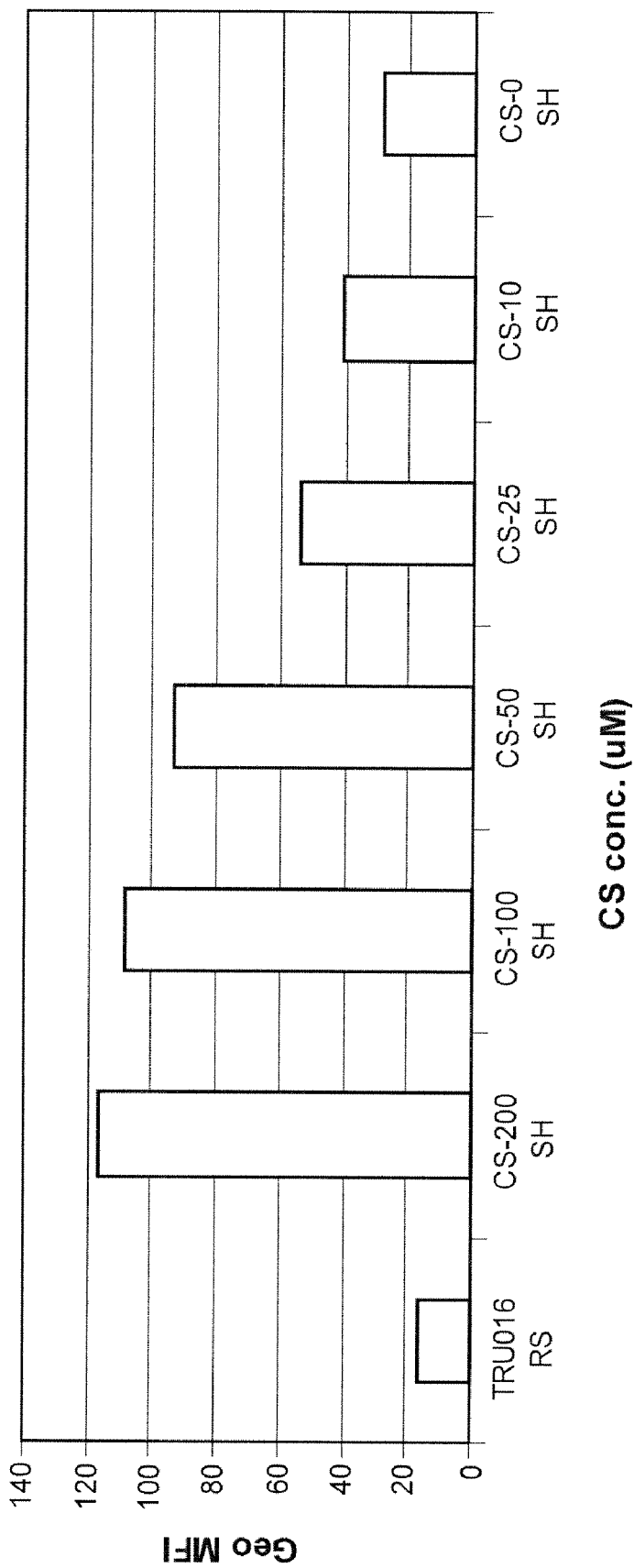
FIG. 6 depicts CD16 binding, as shown by mean fluorescent intensity, of Protein A-purified TRU-016 produced by cells cultured in the presence of varying concentrations of castanospermine.
Figure 7:
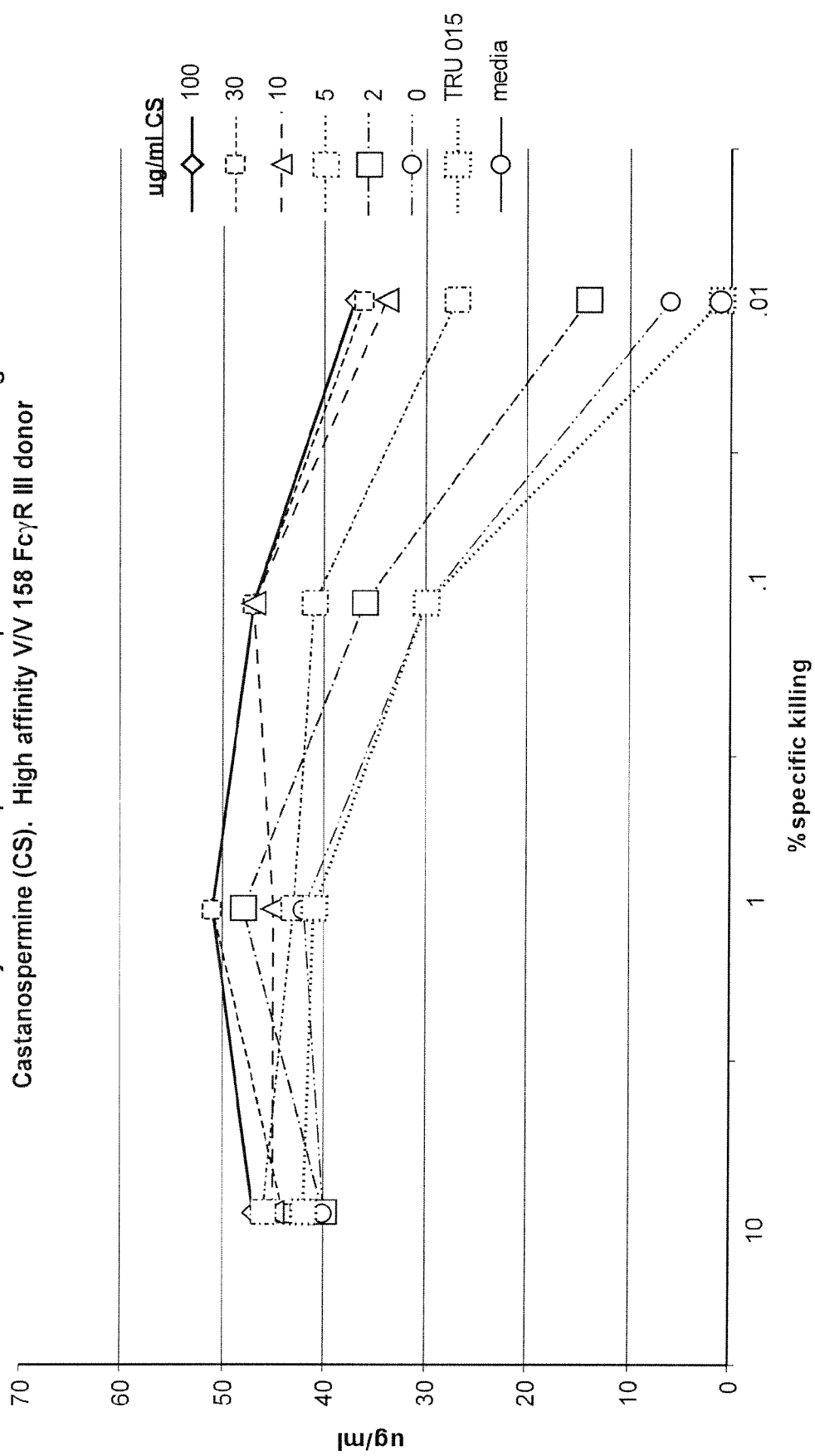
FIGS. 7 and 8 depict ADCC of TRU-015 measured using PBMC of high affinity and low affinity donors, respectively, and plots concentration of TRU-015 added vs. % specific killing.
Figure 8:
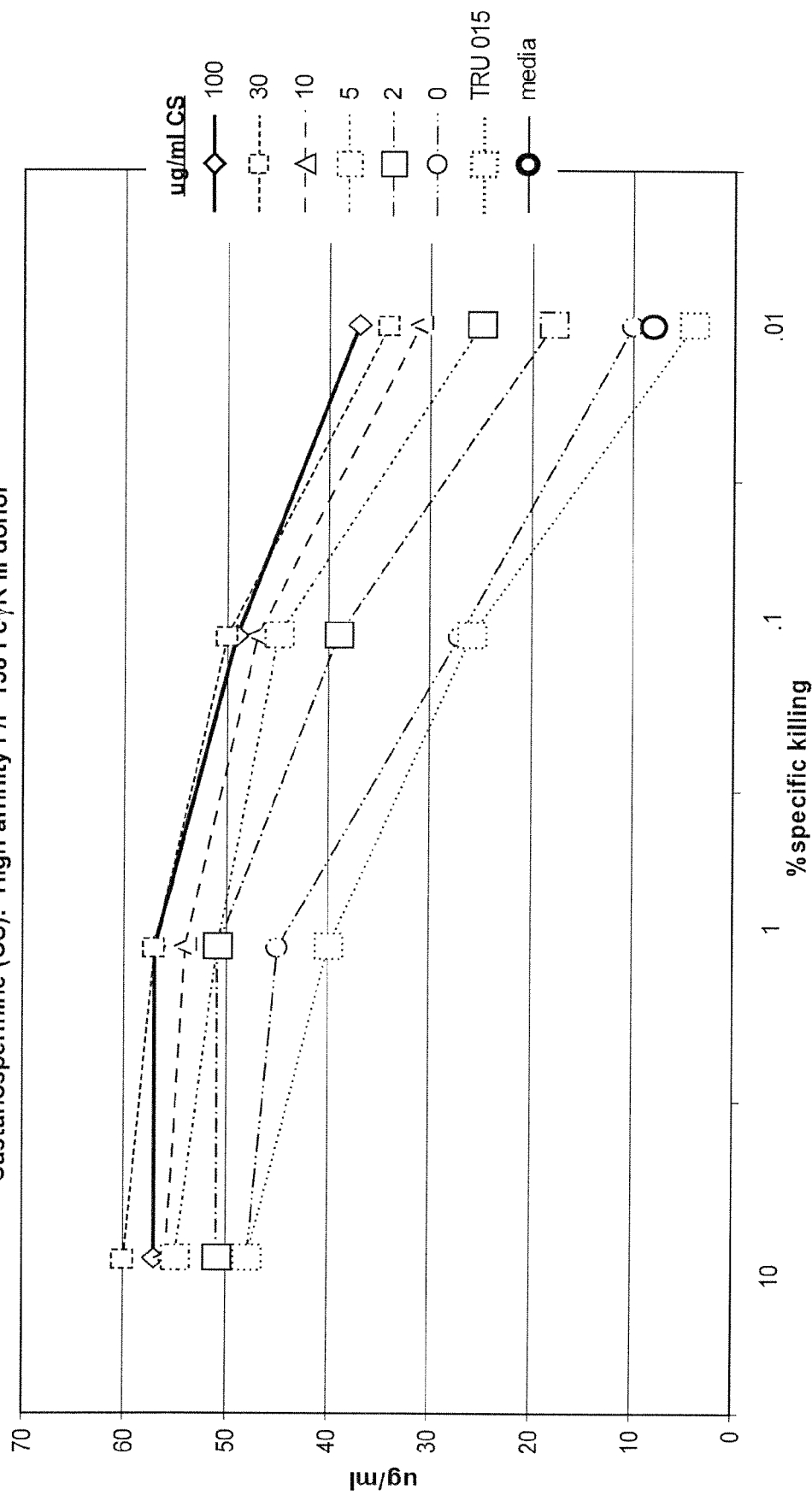
Figure 9:
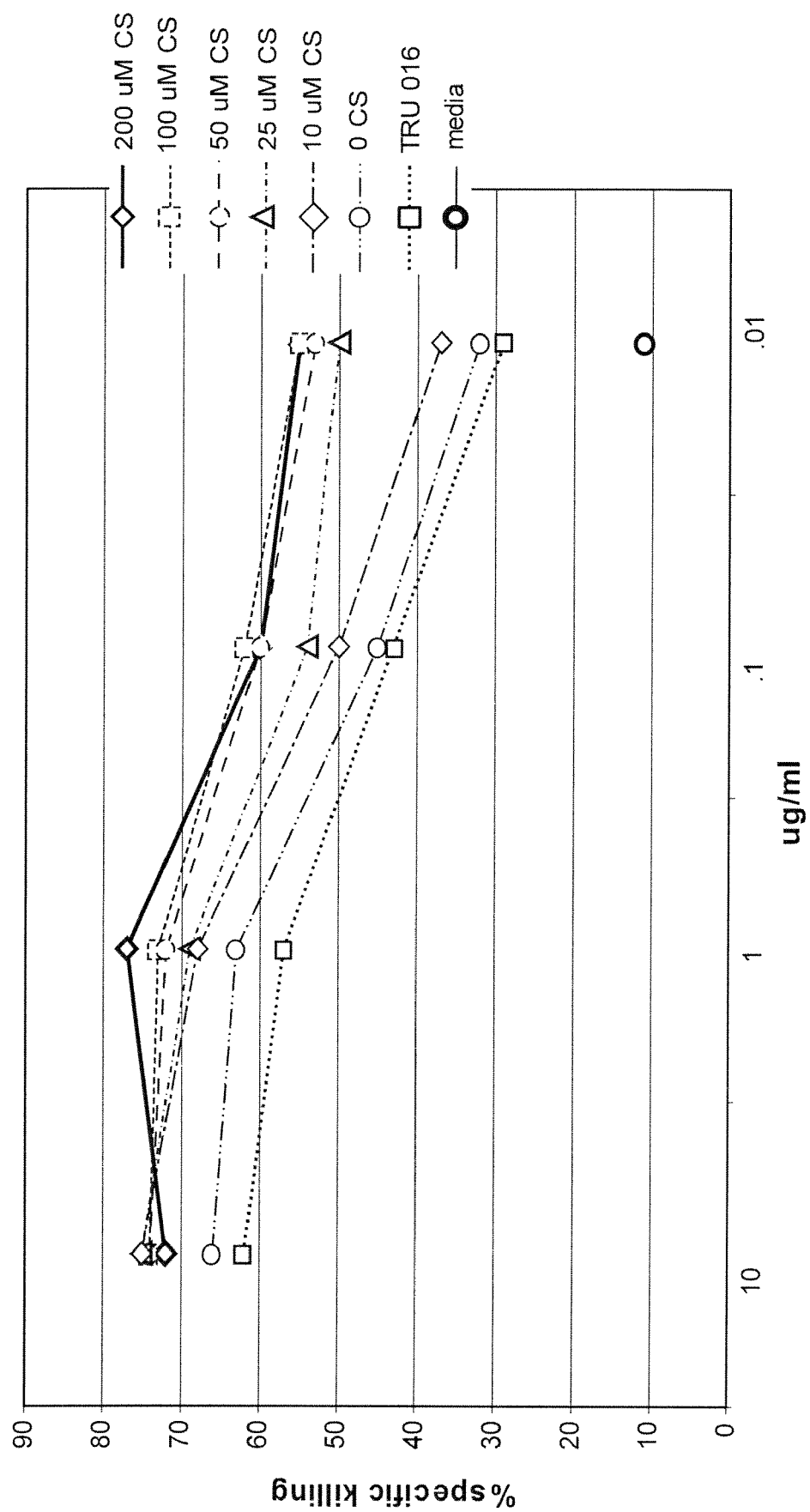
FIG. 9 depicts ADCC of TRU-016 produced by cells cultured in the presence of varying concentrations of castanospermine, and plots % specific killing vs. concentration of TRU-016 added.
Figure 10:
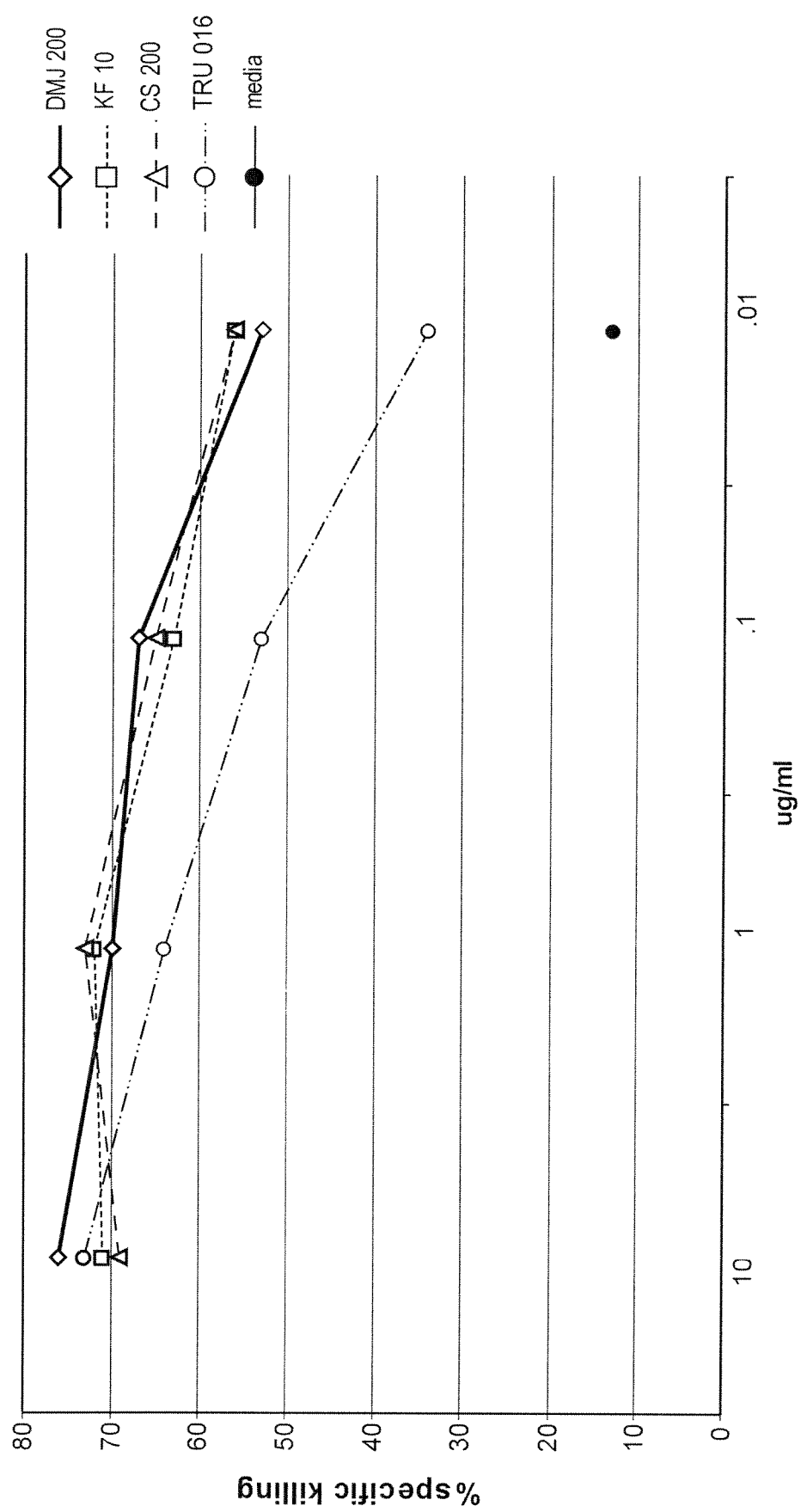
FIG. 10 depicts ADCC of TRU-016 produced by cells cultured in the presence of various carbohydrate modifiers, and plots % specific killing vs. concentration of TRU-016 added.

FIGS. 1 and 2 are representative and show that treatment with the carbohydrate modifier castanospermine at concentrations up to 1000 μM did not affect cell counts or percent cell viability over all time periods sampled (up to 144 hours).

Example 3

Binding to FcRs

The immunoglycoproteins produced according to Example 2 were assayed in vitro for binding to soluble Ig-fusion versions of Fcγ receptors, in which the extracellular domain of a receptor is fused to murine IgG2a Fc.

The soluble Fcγ receptor materials were generated by fusing the extracellular domain of Fcγ Receptors I (Genbank Acc. No. BC032634), IIa (Genbank Acc. No. NM_021642), IIb (Genbank Acc. No. BC031992), and III-V158 (high affinity allele) (Genbank Acc. No. X07934) and III-F158 (low affinity allele), respectively, to a murine IgG2a Fc with a Pro to Ser mutation at residue 238 (MIgG2aP238S). For both forms of Fcγ RIII (CD16), an HE4 leader was cloned onto CD16 amino acids 1-178 and then fused to MIgG2aP238S.

The assays were carried out as follows. 500,000 WIL2-S cells (a B lymphoma cell line that expresses CD37 as well as CD20 on its surface) were incubated on ice in a Costar 96 well plate with 5 μg/ml of either TRU-015 or TRU-016 for 45 minutes in phosphate buffered saline (PBS) with 1% fetal bovine serum (FBS). Unbound TRU-015 or TRU-016 was removed by spinning the cells, washing with diluent (PBS+1% FBS) and spinning again at 1200 rpm in a Sorvall Legend RT for 2 minutes. The cells were then incubated with the desired FcγR-MIg fusion in the same diluent at a concentration of 1 μg/ml on ice for 45 minutes.

The complexes (WIL2-S cells/SMIP/FcγR-MIg) were then incubated with PE conjugated AffiniPure F(Ab')$_2$ Goat Anti-Mouse IgG [Jackson Immunoresearch] (a mouse Fc-specific antibody with minimal cross reactivity with human Fc) at a 1:100 dilution. The cells were analyzed by one-color flow cytometry on a FACsCalibur using CellQuest software (Becton Dickinson).

If TRU-016 supernatants from Example 2 were used in this assay instead of purified TRU-016 protein, the SMIP concentration in the supernatant was quantified by direct staining of WIL2-S cells with diluted supernatant along with a TRU-016 standard. TRU-016 was detected by staining with FITC conjugated F(Ab')$_2$ Goat Anti-Human (gamma) [Caltag H10101] at a 1:50 dilution.

Binding to either the low affinity allele and high affinity allele were determined to correlate similarly to ADCC activity. An increase in CD16 (low or high affinity allele) binding was correlated to an increase in ADCC activity.

Representative results are displayed in FIGS. 3-6.

TRU-015 purified protein produced by CHO cells cultured in media containing 0, 2, 5, 10, 30 or 100 μg/mL castanospermine was tested for CD16 binding (low affinity allele). Representative results of geometric mean fluorescence intensity are displayed in FIG. 3 and show a dose-dependent increase in CD16 binding at increasing concentrations of castanospermine in the culture media.

TRU-016 supernatant produced by CHO cells cultured in media containing 6,8a-diepicastanospermine at a concentration of 50 or 250 μM, swainsonine at a concentration of 50 or 250 μM, or deoxymannojirimycin (DMJ) at a concentration of 50 or 250 μM was tested for CD16 binding. Representative results of mean fluorescence intensity are displayed in FIG. 4 and show that both concentrations of DMJ increased CD16 binding. Although no effect was seen for 6,8a-diepicastanospermine or swainsonine at these concentrations, further tests with purified protein are carried out to determine effect.

TRU-016 supernatant produced by CHO cells cultured in media containing kifunensine at a concentration of 0, 0.5, 1, 3, 5, or 10 μM was tested for CD16 binding. Representative results of mean fluorescence intensity are displayed in FIG. 5 and show that kifunensine was much more potent than DMJ at increasing CD16 binding and greatly increased CD16 binding even at the lowest concentration, 0.5 μM.

Protein A-purified TRU-016 produced by CHO cells cultured in media containing 0, 10, 25, 50, 100 or 200 μM castanospermine was tested for CD16 binding. Representative results of mean fluorescence intensity are displayed in FIG. 6 and show a dose-dependent increase in CD 16 binding at increasing concentrations of castanospermine in the culture media.

Example 4

ADCC Activity

To determine the ADCC activity of purified TRU-016, labeled BJAB B cells were used as targets and human peripheral blood mononuclear cells (PBMC) as effector cells. BJAB B cells ($10^7$ cells) were labeled with 500 μCi/mL $^{51}$Cr sodium chromate for 2 hours at 37° C. in IMDM/10% FBS. PBMCs were isolated from heparinized, human whole blood by fractionation over Lymphocyte Separation Media (LSM, ICN Biomedical) gradients. Reagent samples were added to RPMI media with 10% FBS and serial dilutions of each reagent were prepared. The $^{51}$Cr labeled BJAB were added at $2\times10^4$ cells/well. The PBMCs were then added at $5\times10^5$ cells/well for a final ratio of 25:1 effectors (PBMC):targets (BJAB). Reactions were set up in quadruplicate wells of a 96 well plate. Serial dilutions of TRU-016 were added to wells at a final concentration ranging from 10 ng/mL to 20 μg/mL as indicated in the figures. Reactions were allowed to proceed for 6 hours at 37° C. in 5% $CO_2$ prior to harvesting and counting. CPM released was measured on a Packard TopCounNXT from 50 μl dried culture supernatant. Percent specific killing was calculated by subtracting (cpm [mean of quadruplicate samples] of sample−cpm spontaneous release)/(cpm maximal release−cpm spontaneous release)×100, and data were plotted as % specific killing versus TRU-016 concentration.

Representative results are displayed in FIGS. 7-10.

TRU-015 purified protein produced by CHO cells cultured in media containing 0, 2, 5, 10, 30 or 100 μg/mL castanospermine was tested for ADCC measured using PBMC from high affinity (V/V158) and low affinity (F/F158) CD16 donors. Representative results of % specific killing are displayed in FIGS. 7 and 8 (high affinity and low affinity donors, respectively) and show a dose-dependent increase in ADCC activity at increasing concentrations of castanospermine in the culture media.

TRU-016 purified protein produced by CHO cells cultured in media containing 0, 10, 25, 50, 100 or 200 μM castanospermine was tested for ADCC. Representative results of % specific killing are displayed in FIG. 9 and show a dose-dependent increase in ADCC activity at increasing concentrations of castanospermine in the culture media.

TRU-016 purified protein produced by CHO cells cultured in media containing 200 μM DMJ, 10 μM kifenunsine or 200 μM castanospermine was tested for ADCC. Representative results of % specific killing are displayed in FIG. 10 and show that all of these concentrations of carbohydrate modifiers improved ADCC of the immunoglycoproteins produced by the CHO cells.

Example 5

CDC Activity

To determine the CDC activity of TRU-016 purified protein produced according to Example 2, Ramos B cells were suspended in Iscoves (Gibco/Invitrogen, Grand Island, N.Y.) at $5\times10^5$ cells/well in 75 µl. TRU-016 (75 µl) were added to the cells at twice the concentrations indicated. Binding reactions were allowed to proceed for 45 minutes prior to centrifugation and washing in serum-free Iscoves. Cells were resuspended in Iscoves with human serum (containing complement) at various concentrations. The cells were incubated 60 minutes at 37° C. Cells were washed by centrifugation and resuspended in staining media with 0.5 µg/ml propidium iodide. Samples were incubated 15 minutes at room temperature in the dark prior to analysis by flow cytometry using a FACsCalibur and CellQuest software (Becton Dickinson).

Figure 15:
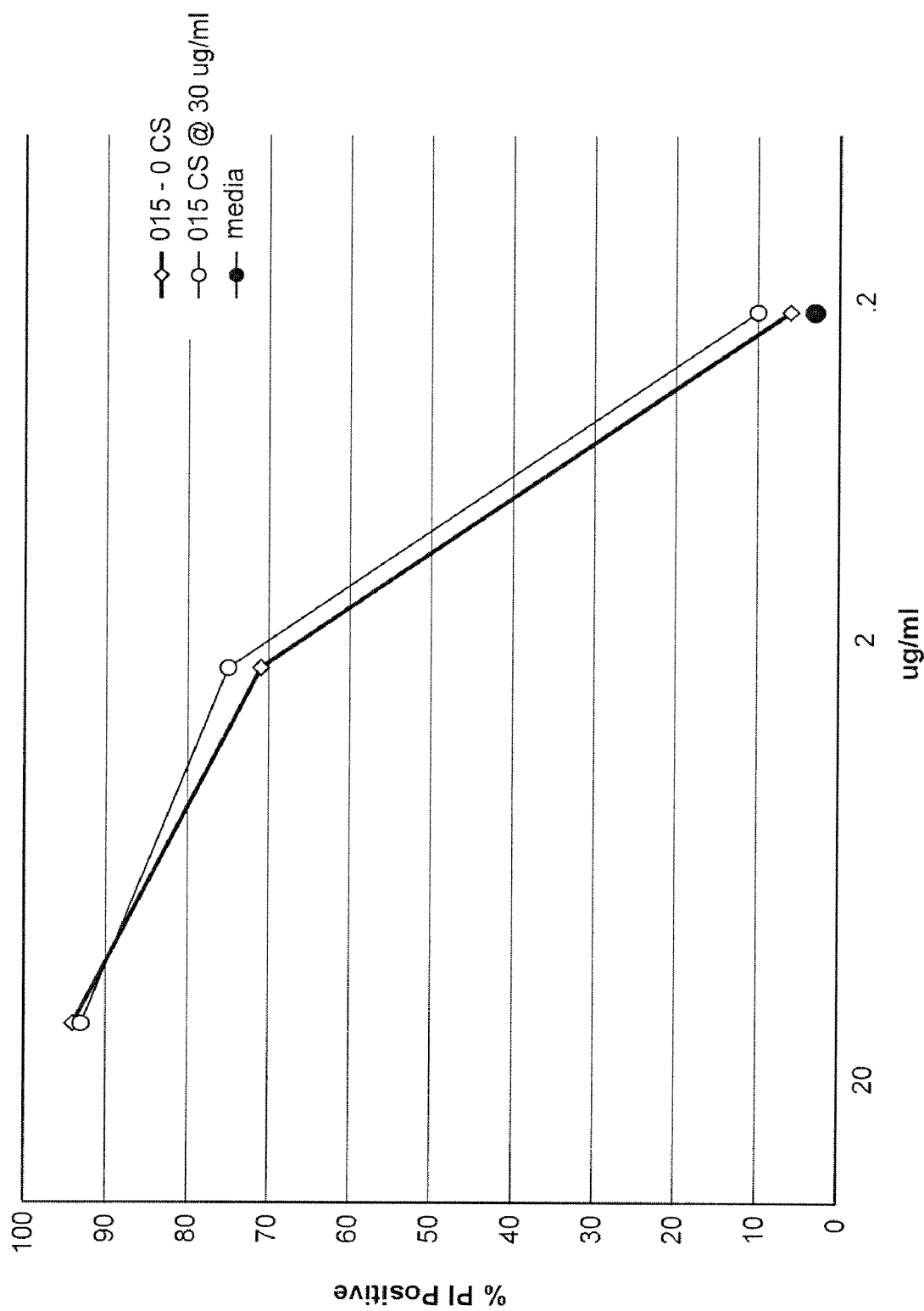
FIG. 15 depicts CDC of TRU-015 produced by cells cultured in the presence of castanospermine, and plots % propidium iodide positive (dead cells) vs. concentration of TRU-015 test protein.

TRU-015 purified protein produced by untreated CHO cells, or CHO cells treated with 30 µg/ml castanospermine was tested for CDC activity. Results are displayed in FIG. 15.

Figure 16:
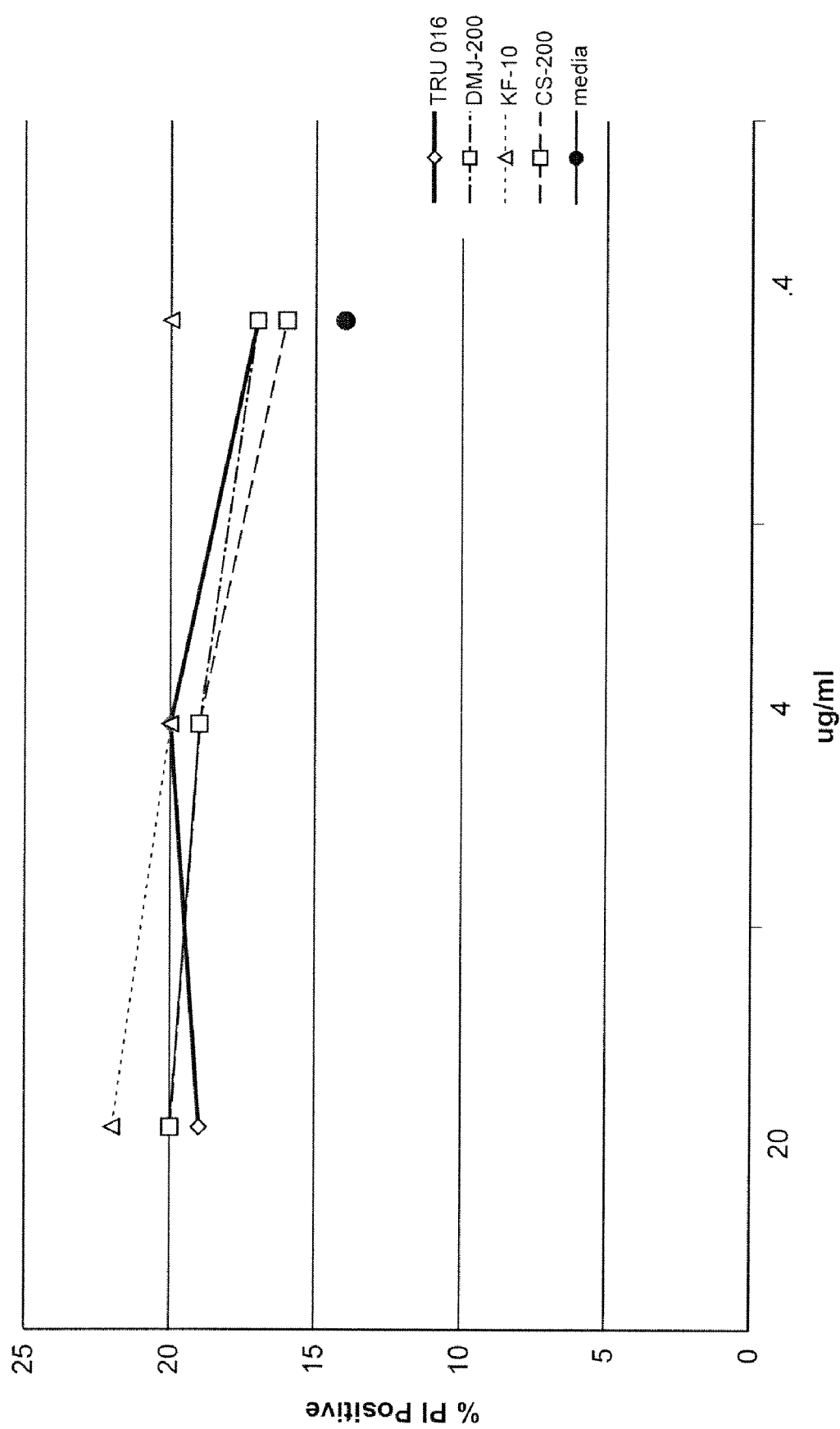
FIG. 16 depicts CDC of TRU-016 produced by cells cultured in the presence of various carbohydrate modifiers, and plots % propidium iodide positive (dead cells) vs. concentration of TRU-016 test protein.

TRU-016 purified protein produced by untreated CHO cells, or CHO cells cultured in media containing 200 µM DMJ, 10 µM kifenunsine or 200 µM castanospermine, was tested for CDC activity. Results are displayed in FIG. 16.

These results show that CDC for carbohydrate-modified TRU-015 or TRU-016 was similar to the CDC of corresponding protein produced by untreated CHO cells, indicating that the presence of carbohydrate modifier in the culture medium of the host cells had no significant effect on CDC of the immunoglycoprotein produced by the host cells.

Example 6

Pharmacokinetic Profile

Female BALB/c mice were injected i.v. with 200 µg of TRU-016 test protein (TRU-016 produced by untreated CHO cells or by CHO cells treated with 200 µM DMJ, 10 M kifenunsine or 200 µM castanospermine) at time 0. Serum samples were collected (3 mice per time point) at 15 min, 2, 6, 24, 48, 72, 96, and 192 hours post injection.

The serum concentration of each TRU-016 test sample was determined in a FACS-based binding assay using the CD37+ Ramos human cell line. CD37+ Ramos cells ($5\times10^5$ cells/well) were incubated in 96 well flat bottom plates along with the serum sample to be tested. Spiked serum samples were used for the standard curves. Cells were incubated at 4° C. for an hour and washed before addition of the detection antibody. Binding of TRU-016 test protein to CD37+ Ramos cells was detected using a fluorescein-conjugated goat anti-human IgG Fcγ fragment-specific antibody. Standard curves were used to construct a binding curve as a function of antigen concentration. Briefly, standard curves consisted of various known concentrations of the TRU-016 test protein spiked into normal mouse serum diluted 1:20 in FACS buffer. The standard curves were run in duplicate on each plate. Mean fluorescence intensities (MFI) from the FACS analysis were imported into Softmax Pro software and were used to calculate serum concentrations of the TRU-016 test protein.

Figure 11:
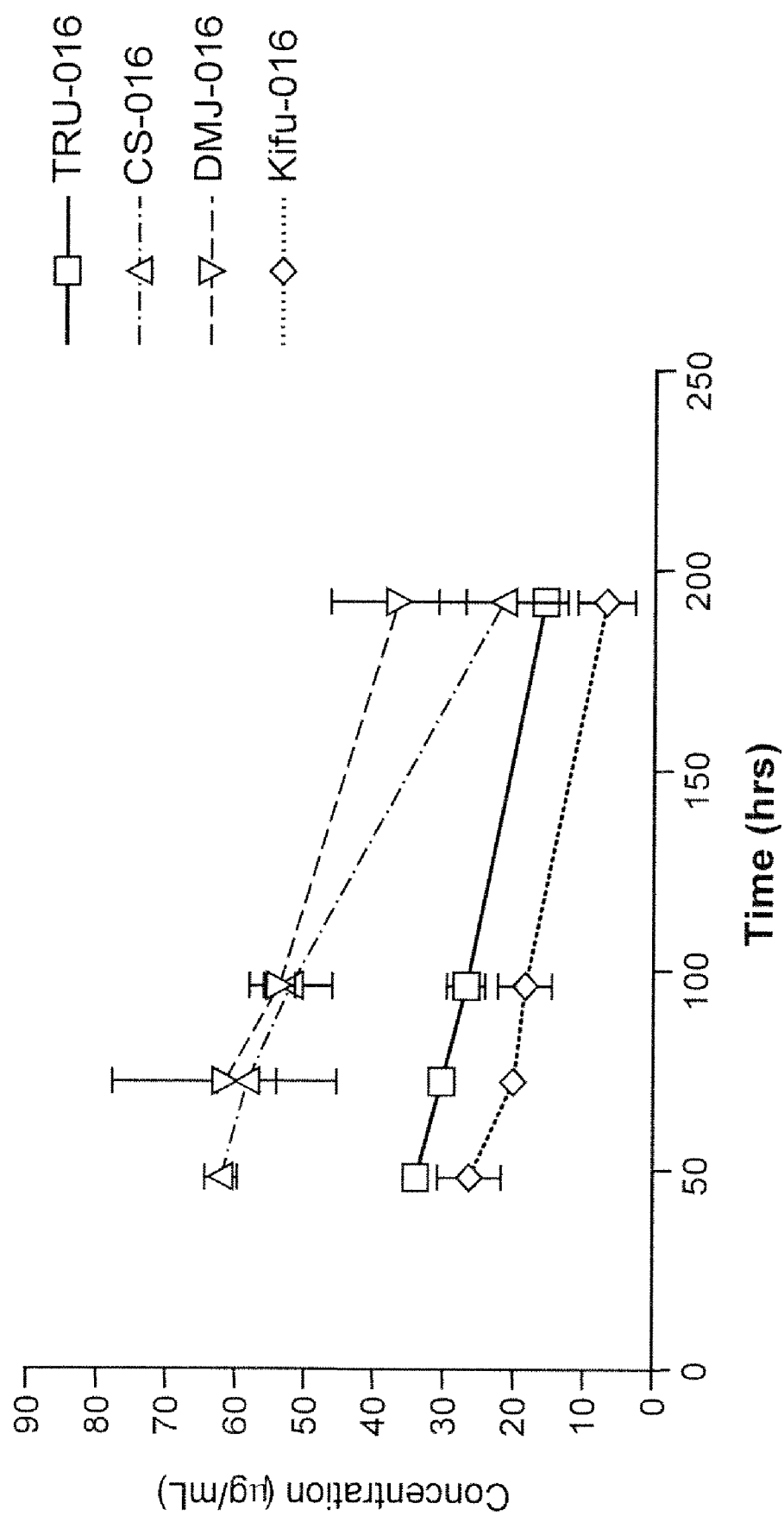
FIG. 11 depicts pharmacokinetic data in mice administered TRU-016 produced by cells cultured in the presence of various carbohydrate modifiers.

Results of the pharmacokinetic study showed that TRU-016 produced by CHO cells cultured in media containing 200 µM DMJ, 10 µM kifenunsine or 200 µM castanospermine (displayed in FIG. 11) when administered to mice exhibited a pharmacokinetic profile similar to TRU-016 produced by untreated CHO cells, indicating that carbohydrate modifier in the culture medium of the host cells had no significant effect on half-life or other pharmacokinetic parameters.

Figure 12:
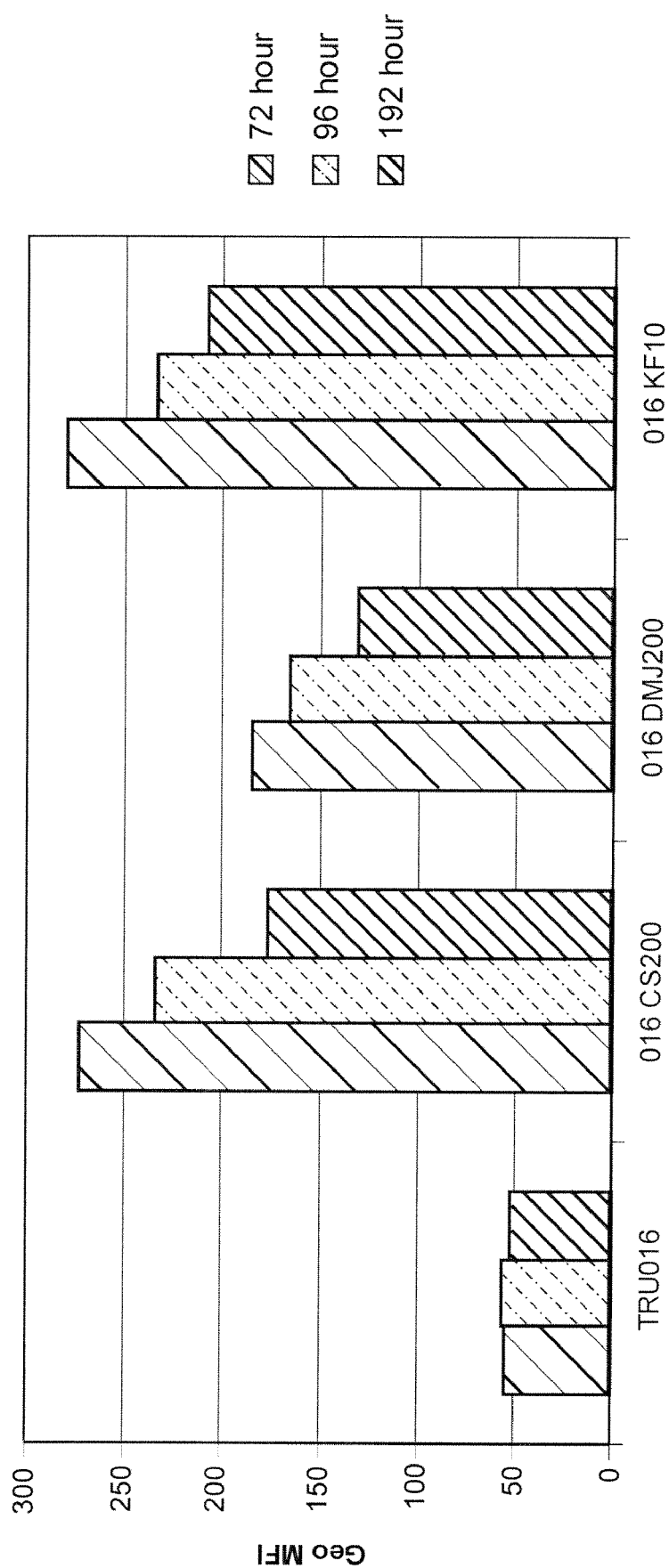
FIG. 12 depicts CD16 binding of TRU-016 in sera of mice administered the TRU-016 produced by cells treated with various carbohydrate modifiers.

Repeating the CD16 assays on sera containing TRU-016 obtained from the mice at 48, 72, 96 and 192 hours after administration of TRU-016 showed that the sera retained its increased CD16 binding activity at all time points tested. Results are shown in FIG. 12.

Example 7

Carbohydrate-Modified Immunoglycoprotein Activity In Vivo

Nude mice are administered $5\times10^6$ Ramos cells subcutaneously on day 0 and injected intravenously with 200 µg control human IgG or TRU-016 test protein produced by CHO cells treated with 200 µM DMJ, 10 µM kifenunsine or 200 µM castanospermine on days 0, 2, 4, 6, and 8. Mice typically develop tumors within 6 days and die shortly thereafter. Tumors are measured three times weekly with digital calipers and LabCat software, and tumor volume is calculated as ½[length×(width)]². Body weight is also determined once a week.

Mice are sacrificed when the tumor reaches 1500 mm³ in size (1200 mm³ on Fridays). Mice are also sacrificed if ulceration of a tumor occurs, the tumor inhibits the mobility of animal, or if weight loss equals or exceeds 20%.

Figure 13:
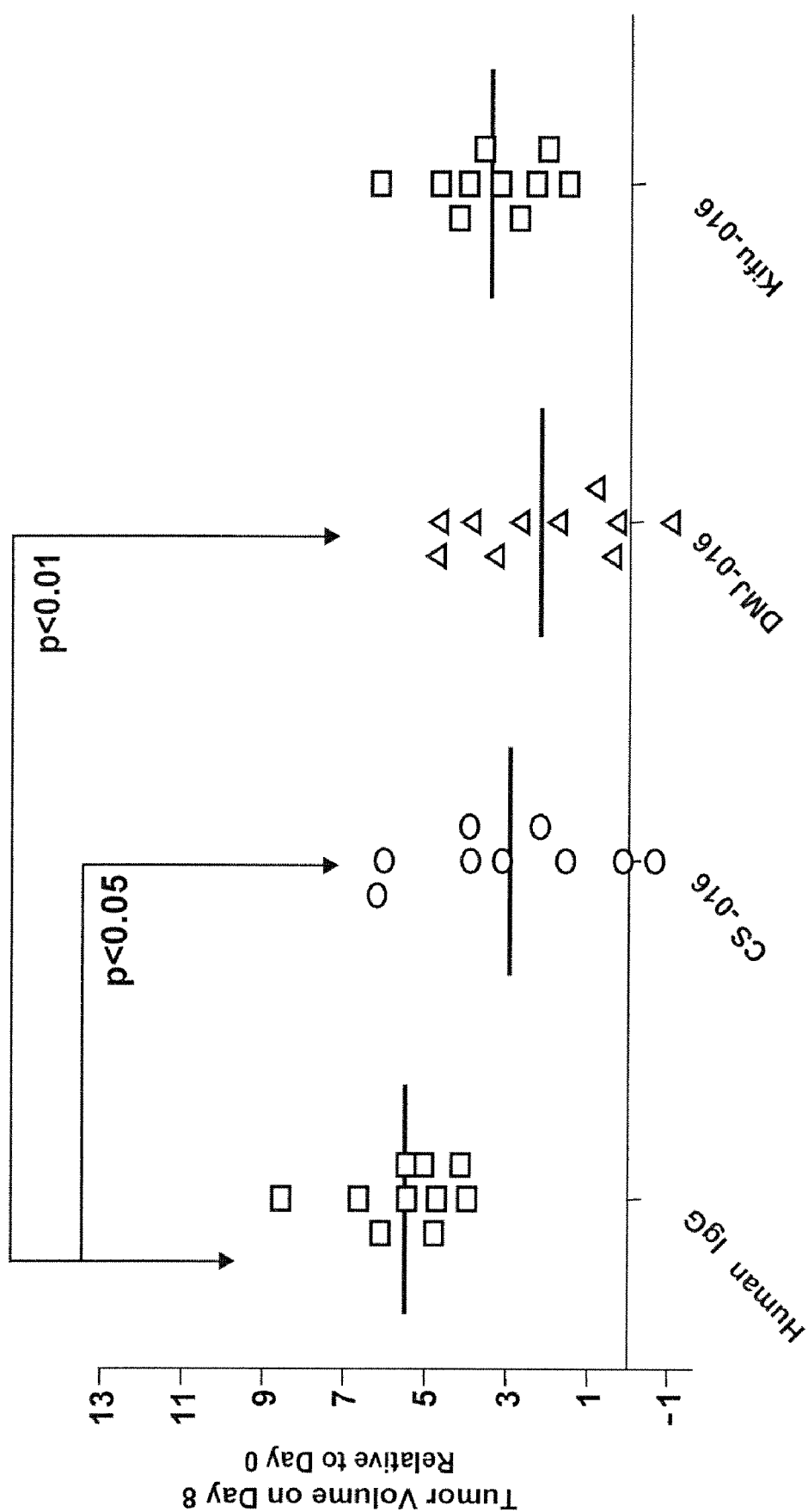
FIG. 13 depicts relative tumor volume at 8 days in mice implanted with tumor cells and administered TRU-016 produced from cells treated with various carbohydrate modifiers, or untreated cells.
Figure 14:
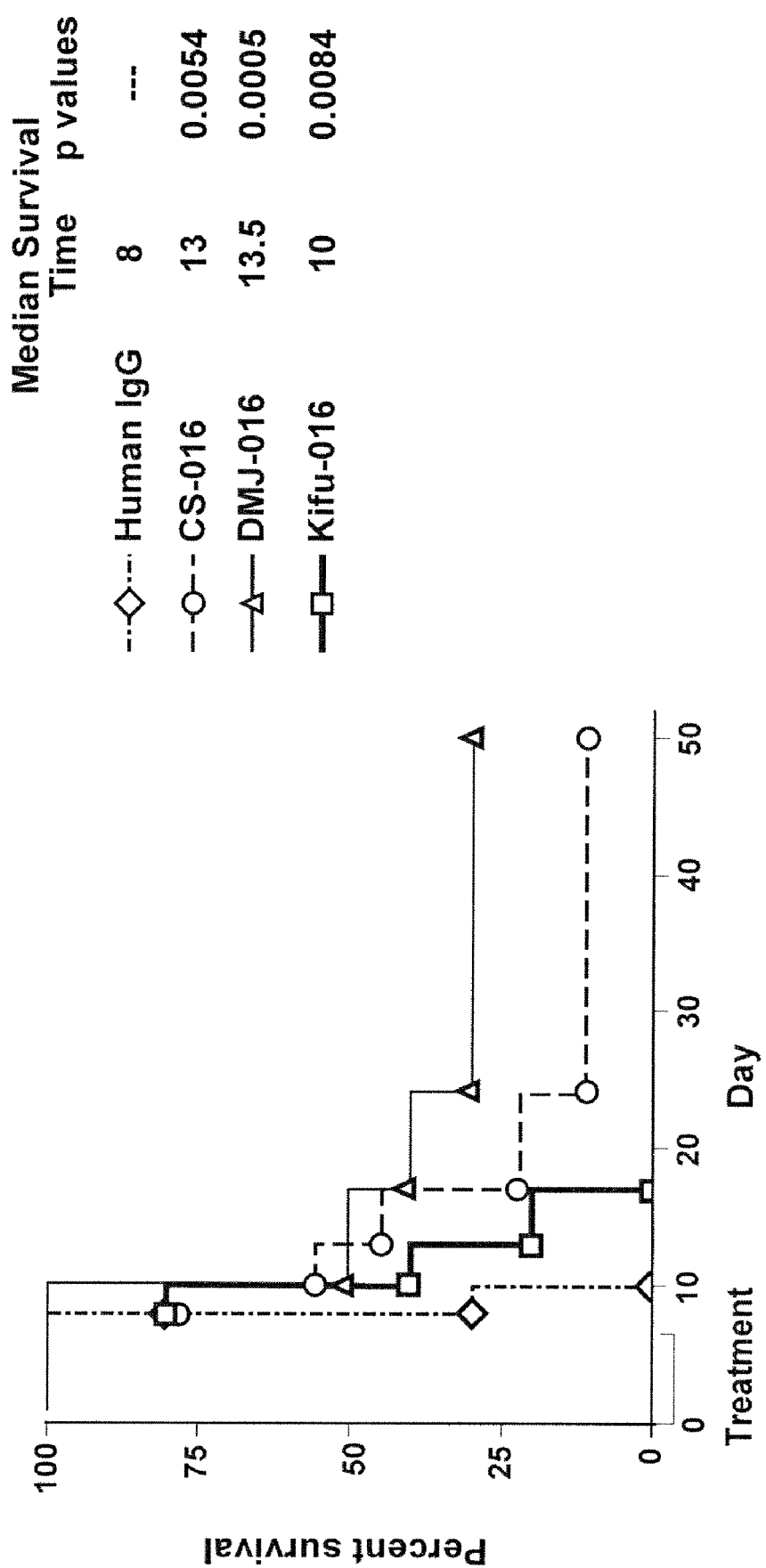
FIG. 14 depicts % survival of mice implanted with tumor cells and administered TRU-016 produced from cells treated with various carbohydrate modifiers, or untreated cells.

Interim results for relative tumor volume at day 8 after the study was initiated are shown in FIG. 13. Data on % survival after the initiation of study are shown in FIG. 14 and below in Table 1.

TABLE 1

| Group | Median Survival Time (Days)* | p value |
|---|---|---|
| HuIgG | 8 | — |
| CS TRU-016 | 13 | 0.0054 |
| DMJ TRU-016 | 13.5 | 0.0005 |
| Kifu TRU-016 | 10 | 0.0084 |

*Values for each of the carbohydrate-modified TRU-016 are significantly different from that of the huIgG treated control group.

Results of this in vivo study showed that TRU-016 produced by CHO cells treated with 200 µM DMJ, 10 µM kifenunsine or 200 µM castanospermine was able to reduce tumor volume and increase mean survival time in an animal model of cancer.

Example 8

Effect of Castanospermine at Varying Concentrations on Protein Production

Further experiments were performed to determine the effect of castanospermine concentration on cell viability, density and specific protein production of TRU-016.

Prior to initiation of the experiments, DG44 CHO cells transfected with TRU-016 were grown in shake flasks in Ex-Cell™ 302 CHO serum-free media (SAFC Biosciences) supplemented with 1× non-essential amino acids (MediaTech), 1× sodium pyruvate (MediaTech), 4 mM L-glutamine (MediaTech), 500 nM methotrexate (MP Biomedicals) and 1 mg/L recombinant insulin (Recombulin-GIBCO/Invitrogen Corp.) at 37° C. and 5% carbon dioxide in a humidified incubator. A 200 mM stock concentration of castanospermine (Alexis Biochemicals) was prepared by dilution of the castanospermine in sterile, distilled/deionized water (MediaTech) and filtration through a 13 mm Acrodisc® with a 0.2 μm HT Tuffryn membrane (Pall Corporation). Stock solution was aliquoted into sterile, O-ringed, 0.5 mL microcentrifuge tubes (Fisherbrand, Fisher Scientific) and frozen at −20° C. Approximately 1 hour prior to initiation of experiments, needed aliquots were thawed at room temperature and the contents of each vial mixed well by vortexing.

For each experiment, cells in log phase growth were seeded in the above medium into a total volume of 60 mL in 250 mL shaker flasks at a density of 200,000 cells/mL and CS added at the concentration to be tested. Final CS concentrations of 800 μM, 400 μM, 200 μM, 100 μM, 50 μM, 25 μM and 0 μM were each tested in duplicate flasks. All cultures were incubated at 37° C. and 5% carbon dioxide in a humidified incubator and monitored at least every other day for viable cell density and overall cell viability.

Cultures were harvested on day 8 when overall cell viability was 50-70% (Expt. 1) and 30-50% (Expt. 2). Cells and cellular debris were removed by centrifugation in a Sorvall Super T21 at 3000 rpm for 20 minutes after which the supernatant was sterile filtered through a Millipore Steriflip unit with a 0.22 μm Millipore Express Plus membrane and stored at 2-8° C. until purification.

Figure 17:
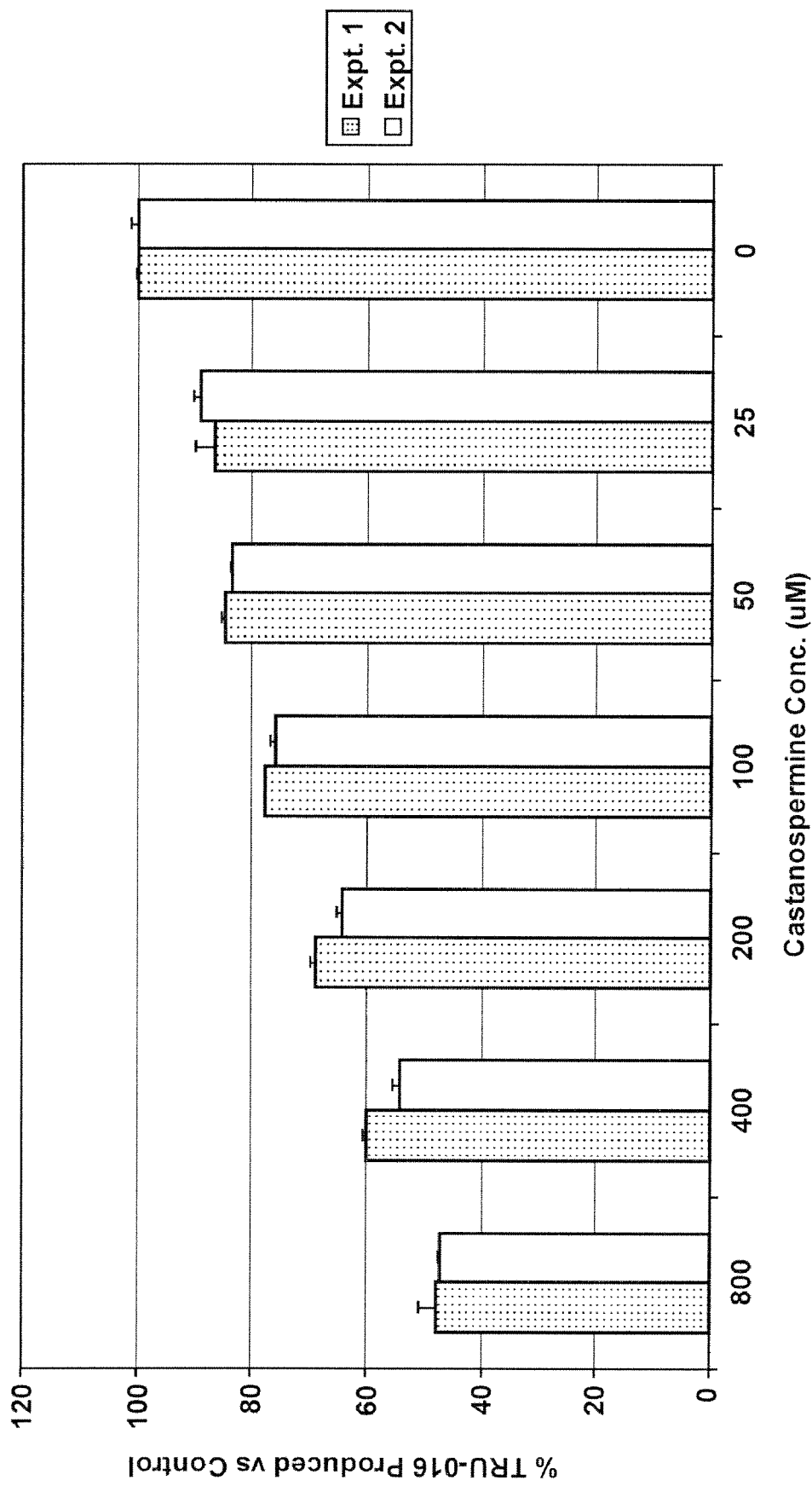
FIG. 17 depicts relative specific protein production of TRU-016 over a range of castanospermine concentrations.

Although cell viability and growth did not appear to be significantly affected as indicated by each sample's integral cell area (ICA), Table 2, increasing concentrations of castanospermine appeared to reduce immunoglycoprotein production. Results are shown in FIG. 17 and in Table 2 below. Concentrations of 400 μm and 800 μm CS are shown to reduce TRU-016 protein production by approximately 40%-55% respectively.

TABLE 2

| CS Conc. (μM) | Viability at Harvest (%) | Average TRU-016 Produced (ug/mL) ± SD | ICA[a] 10⁶ cells * days/mL | Specific Productivity[b] (pg/cell/day) |
|---|---|---|---|---|
| 800 | 70.6 | 99.65 ± 6.1 | 23.9 | 3.99 |
| 800 | 65.2 |  | 23.8 | 4.36 |
| 400 | 68.2 | 124.93 ± 1.4 | 22.4 | 5.53 |
| 400 | 65.7 |  | 23.0 | 5.48 |
| 200 | 55.5 | 143.53 ± 1.4 | 21.9 | 6.60 |
| 200 | 51.1 |  | 22.0 | 6.47 |
| 100 | 54.4 | 161.83 ± 0.1 | 21.6 | 7.48 |
| 100 | 54.6 |  | 21.6 | 7.49 |
| 50 | 49.4 | 176.63 ± 1.0 | 21.6 | 8.15 |
| 50 | 50.0 |  | 21.4 | 8.27 |
| 25 | 53.9 | 180.31 ± 6.6 | 21.4 | 8.22 |
| 25 | 54.5 |  | 21.1 | 8.78 |
| 0 | 65.1 | 208.24 ± 0.3 | 22.4 | 9.29 |
| 0 | 62.6 |  | 21.7 | 9.62 |

[a]Integral Cell Area (ICA) ICA = ((VCC$_n$ + VCC$_{n+1}$)/2) × (t$_{n+1}$ − t$_n$)
where
VCC$_n$ = viable cell density at time n
VCC$_{n+1}$ = viable cell density at time n + 1
units: 10⁶ cells * days/mL
[b]Specific Productivity = total amount produced (ug/mL)/ICA units: pg/cell/day Example 9

Assay for Simultaneous Binding of TRU-016 to CD37 and FcγRIIIa (CD16)

Experiments were performed to determine the effect of castanospermine concentration on functional activity of TRU-016 as measured by its binding to FcγRIIIa and its binding to target antigen CD37.

TRU-016 produced as described in Example 8 was tested in the following assay, which simultaneously evaluates the ability of the TRU-016 binding domain to bind to a CD37 expressing target cell and the ability of the Fc portion of the TRU-016 SMIP to bind a fusion protein of human CD16 and murine IgG Fc.

The target cell utilized is the Daudi (ATCC CRL-213) cell line. Daudi cells are a human B-lymphoblastoid cell line derived from a Burkitt's lymphoma and express high levels of CD37. The custom soluble CD16:MuIgGFc fusion protein is human CD16 (low affinity polymorphism) linked to a murine IgG Fc.

The appropriate number of Daudi cells (350,000/well times the number of wells) is aliquoted and centrifuged at 250×g for 5 minutes at 15° C. The supernatant is removed. One percent cold paraformaldehyde is prepared by diluting the 4% stock from USB (USB US19943) 1:4 with FACS Buffer. FACS Buffer is prepared by adding 2% FBS (Gibco) to Dulbecco's PBS (Invitrogen) (v/v) and sterile filtering with a 0.22 μm filter. FACS Buffer is stored and used at 4° C. The cells are resuspended in 1% paraformaldehyde (a volume equal to 50 μL/well times the number of wells) and plated out in a round bottom 96-well plate. The cells are incubated for 30 minutes at 4° C. Following this incubation the cells are washed by adding 150 μL of FACS Buffer to each well, centrifuging at 250×g for 3 minutes at 15° C. and the supernatant removed. The cells are resuspended in 50 μL of FACS Buffer. TRU-016 is diluted in FACS Buffer, at concentrations ranging from saturation to background levels (24 μg/mL-0.011 μg/mL), added to the appropriate wells, 50 μL/well, and the cells incubated for 25 minutes at 4° C. The CD16:MuIgGFc fusion protein is diluted in FACS Buffer to a saturating level (20 μg/ml) and added to the assay (50 μL/well) and incubated for an additional 30 minutes at 4° C. to form a complex with the TRU-016 that has bound to the cell surface. Any unbound reagents are removed from the well by centrifuging at 250×g for 3 minutes at 15° C., removing the supernatant and then washing 3 times with 200 μL/well of FACS Buffer. The cells are then incubated with a fluorophore (R-phycoerythrin, Jackson 115-116-071) tagged F(ab')2 antibody, specific to murine Fc (and selected to be minimally reactive to human Fc). This antibody will bind to the MuIgGFc portion of the CD16:MuIgGFc fusion protein. The antibody is diluted 1:200 in FACS Buffer and 100 μL is added to each well. The plate is incubated at 4° C. in the dark for 45 minutes. Any unbound R-PE is removed by adding 150 μL of FACS Buffer to each well and centrifuging at 250×g for 3 minutes at 15° C. followed by removal of supernatant. This is followed by a second wash with 200 μL/well FACS Buffer, centrifuging at 250×g for 3 minutes at 15° C. and removal of supernatant. The cells are resuspended with 200 μL/well 1% paraformaldehyde and stored at 4° C. overnight.

Each sample's bound fluorescence is measured on a BD FACSCalibur flow cytometry system and analyzed with Cell Quest Pro software (Becton Dickinson, ver 5.2). The GeoMean fluorescence intensity for each sample is plotted relative to the TRU-016 concentration. A dose response is generated and fit to a 4-parameter logistic (4-PL) curve using SoftMax Pro software (Molecular Devices, ver 5.0.1). Titrations of TRU-016 are utilized to create a dose response curve of test and reference material for comparison. The "D"-parameter (Maximal curve asymptote) is used as reference for comparison of treated and untreated samples. An increase in the "D" value represents in increase in the binding activity for the corresponding sample.

Figure 18:
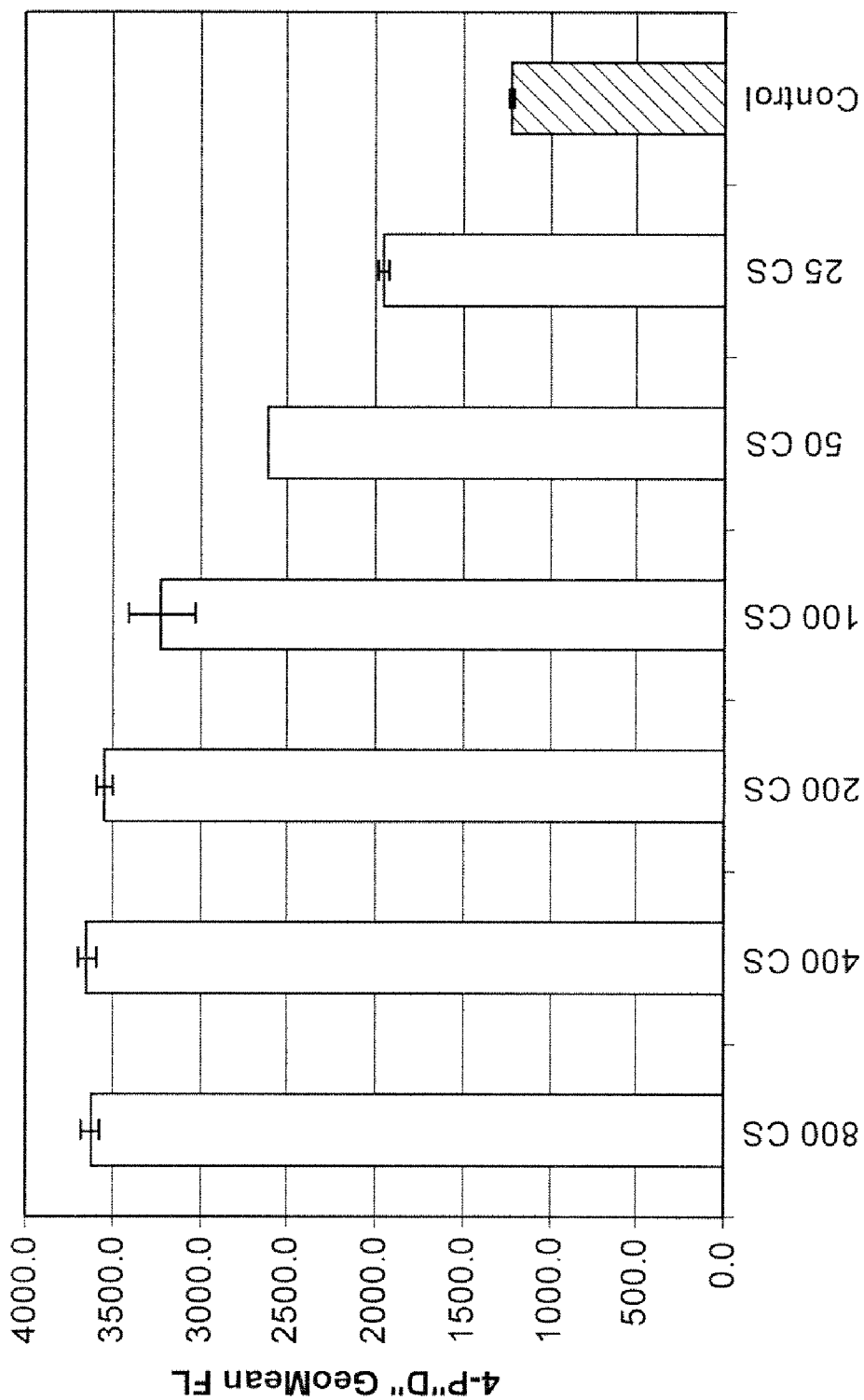
FIG. 18 depicts the results of an assay for simultaneous binding of TRU-016 to CD37 and FcγRIIIa (CD16) over a range of castanospermine concentrations.

Results of the experiment are displayed in FIG. 18 and show a dose-dependent binding response relative to concentration of CS up to 400 µM, at which point the binding appears to level off.

To demonstrate that the enhanced binding of CS treated TRU-016 samples to CD16 was not in part due to enhanced binding of the molecules to CD37, the above assay was repeated except that after addition and incubation of treated or untreated TRU-016 samples in the assay plate, unbound TRU-016 is removed from the well by centrifuging at 250×g for 3 minutes at 15° C., removing the supernatant and then washing 3 times with 200 µL/well of FACS buffer. The cells are then incubated with a FITC-conjugated goat anti-human IgG Fc specific antibody (Caltag H10501). This antibody will bind to the Fc region of the human IgG chain of TRU-016 bound to the cells. The antibody is diluted 1:50 in FACS buffer and 100 µL is added to each well. The plate is incubated at 4° C. in the dark for 45 minutes. Any unbound FITC-labeled antibody is removed by adding 100 µL of FACS buffer to each well, centrifuging at 250×g for 3 minutes at 15° C. followed by removal of supernatant. This is followed by a second wash with 200 µL/well FACS buffer. The cells are resuspended with 200 µL/well 2% paraformaldehyde and stored at 4° C. overnight. Each sample's bound fluorescence is measured on a BD FACSCalibur flow cytometry system and analyzed using Cell Quest Pro software (Becton Dickinson, ver 5.2). The GeoMean fluorescence intensity for each sample is plotted relative to the TRU-016 concentration. A dose response curve is generated and fit to a 4-parameter logistic (4-PL) curve using the SoftMax Pro software (Molecular Devices, ver 5.0.1). Titrations of TRU-016 are utilized to create a dose response curve of the untreated control and CS treated samples for comparison.

Figure 19:
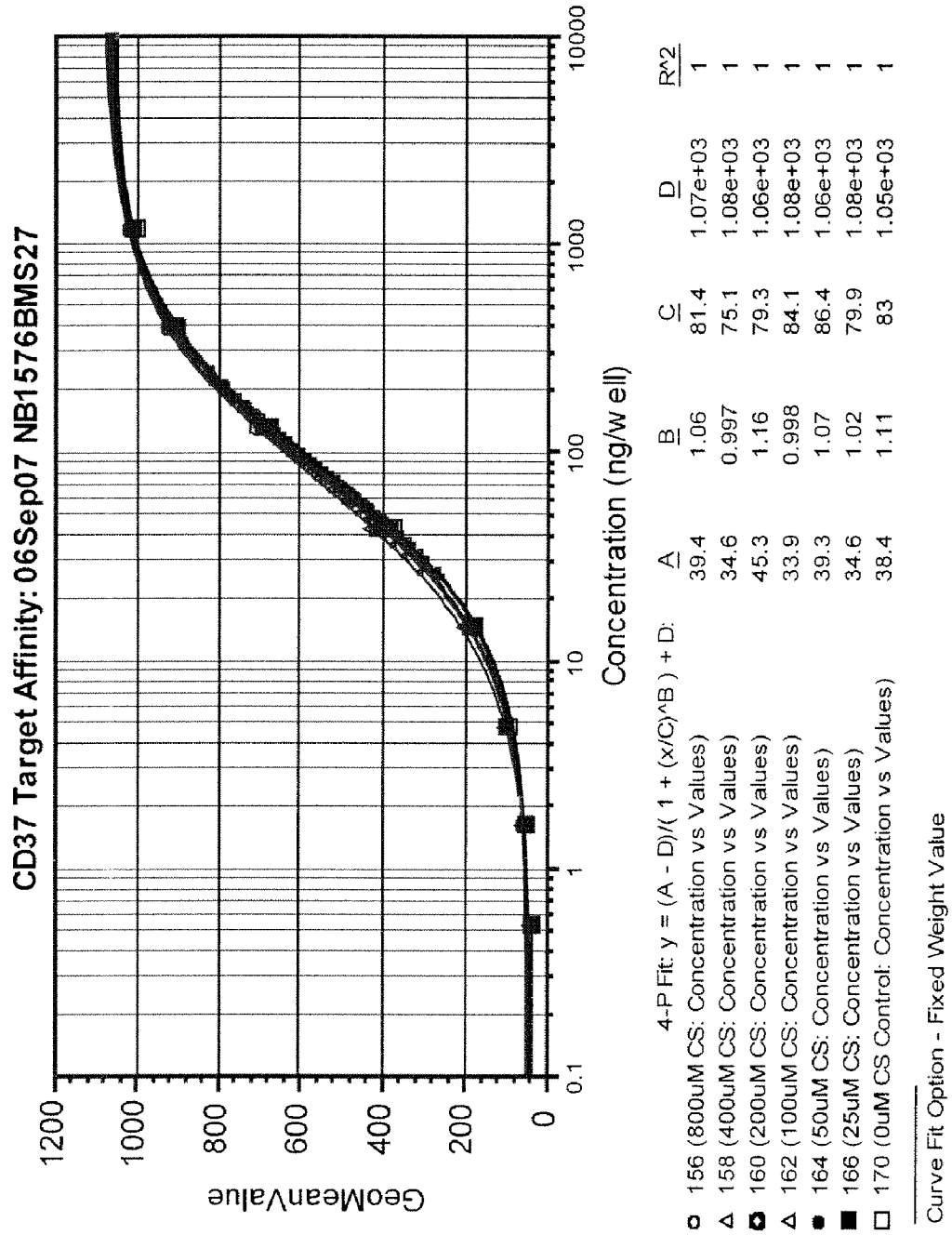
FIG. 19 depicts dose response binding curves of TRU-016 to CD37-expressing cells for a range of castanospermine concentrations.

As shown in FIG. 19, the dose response binding curves to CD37 expressing cells for all CS treated samples were essentially identical to each other and to the untreated TRU-016 sample, indicating that treatment with CS did not alter the binding of TRU-016 to its specific target antigen.

Example 10

Antibody Dependent Cellular Cytotoxicity (ADCC) Assay

Experiments were performed to determine the effect of castanospermine concentration on functional activity of TRU-016 as measured by ADCC activity.

TRU-016 produced as described in Example 8 is incubated with the CD37-expressing Daudi cancer B-cell line in conjunction with primary human peripheral blood lymphocytes (PBL's) effector cells to assess ADCC activity.

Daudi target cells ($5 \times 10^6$) are added to a 15 ml conical tube and then centrifuged at 250×g for 5 minutes at 20° C. and the supernatant removed. The cell pellet is resuspended by the addition of 0.3 mCi Chromium-51 ($^{51}$Cr, GE Healthcare, CJ51). The cells are incubated for 75 minutes at 37° C. with 5% $CO_2$, allowing the cells to incorporate the radioactive isotope. The cells are then washed three times to remove any unincorporated $^{51}$Cr. This is done by adding 10 mL of complete media—IMDM (Gibco) with 10% FBS (Gibco)—to the tube, centrifuging at 250×g for 5 minutes at 20° C. followed by removal of supernatant. The final resuspension is in 11.5 mL of complete media. TRU-016 is diluted in complete media, at concentrations that are able to generate maximal to background levels of cell lysis (500 ng/mL-0.005 ng/mL). These titrations are plated out, 50 µL/well, in a round bottom 96 well plate. The $^{51}$Cr labeled target cells are added to the dose titrations of TRU-016 at 50 µL/well and the control wells (control media without TRU-016). PBL's are isolated from fresh heparinized whole blood by density gradient centrifugation using Lymphocyte Separation Media as per protocol (LSM, MP Biomedical, 50494/36427). PBL effector cells are added, 100 µL/well, to the wells at a ratio of between 25:1-30:1 (effector: target). The assay is incubated for 4.5-5 hours at 37° C., 5% $CO_2$. The effector cells lyse the target cells relative to the TRU-016 concentration, releasing a proportional amount of $^{51}$Cr into the assay supernatant. Following the incubation the plate is centrifuged at 250×g for 3 minutes at 20° C. A 25 µL volume of cell-free supernatant is removed from all wells to a scintillation plate (Perkin Elmer 6005185) and dried overnight. The amount of $^{51}$Cr isotope in each well of the scintillation plate is measured using a Topcount plate reader (Perkin Elmer, C9904VO). The data are expressed as percent of specific release. Specific release is calculated as:

(Sample value−Spontaneous value)/(Maximum value−Spontaneous value)*100%

Spontaneous=amount of $^{51}$Cr released from target cell only

Maximum release=amount of $^{51}$Cr released from targets treated with detergent lysing agent Background Control=amount of $^{51}$Cr released from target cells+effector cells(No TRU-016)

Figure 20:
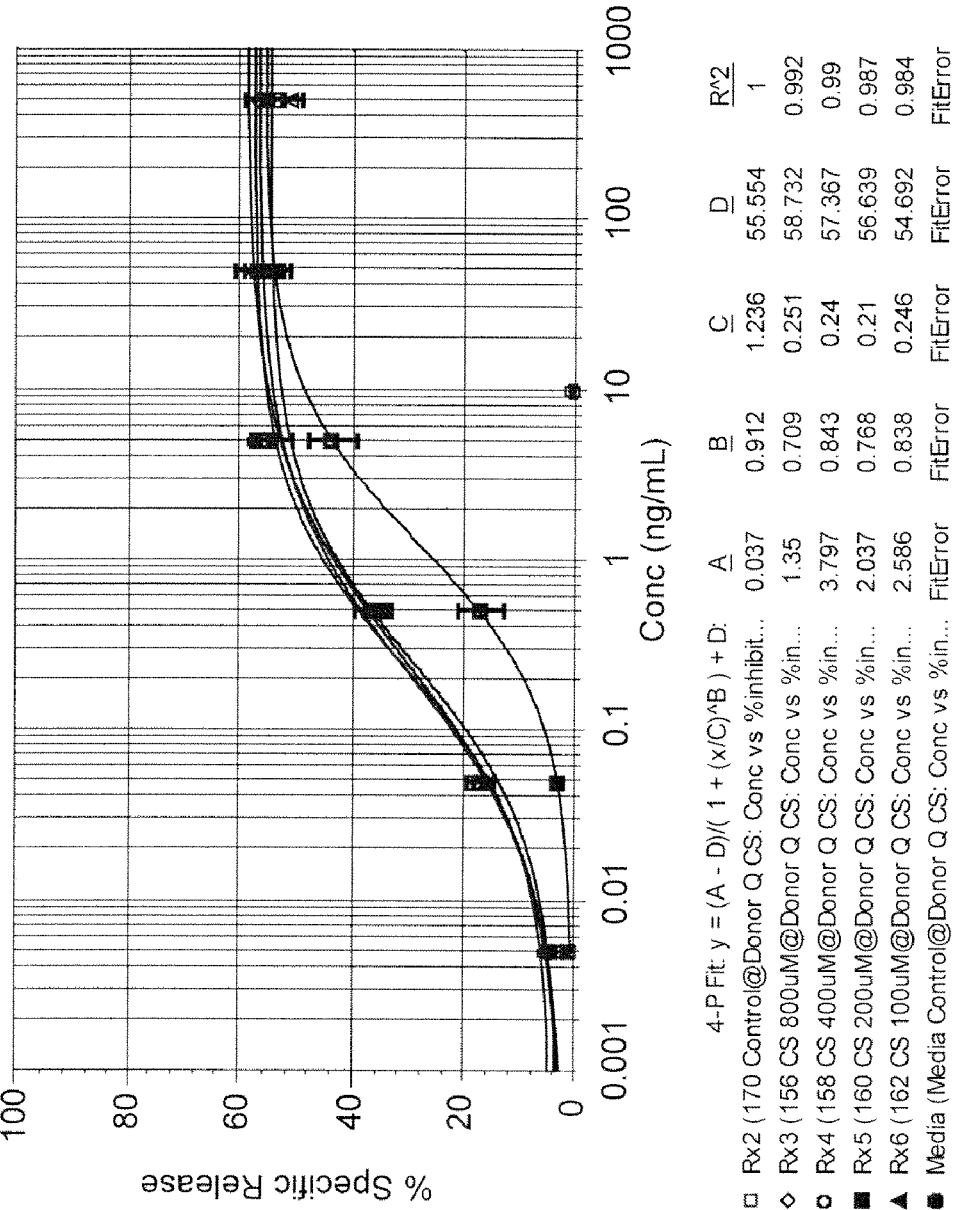
FIG. 20 depicts ADCC activity curves of TRU-016 over a range of castanospermine concentrations.

A dose response is generated and fit to a 4-parameter logistic curve using SoftMax Pro software (Molecular Devices, ver 5.0.1). Titrations of TRU-016 are utilized to create dose response curves of test and reference material for comparison. The EC50 values for the treated articles are compared to the untreated control (no CS) to determine the percent increase in ADCC activity. The Table below summarizes the data displayed in FIG. 20. The data indicate that the ADCC activity of TRU-016, treated with CS over a range of 100 µM-800 µM final concentration, is significantly increased relative to untreated TRU-016.

TABLE 3

| Sample ID | Donor Q High 1:17 | Donor N Low 1:17 | Donor AF Heterozygous 1:25 | Donor AF Heterozygous 1:13 |
|---|---|---|---|---|
| Control CS 0 µM | 1.24 | 2.60 | 0.23 | 0.37 |
| CS 100 µM | 0.25 (502%) | 0.70 (370%) | 0.03 (728%) | n/a |
| CS 200 µM | 0.21 (589%) | 0.54 (479%) | n/a | 0.06 (579%) |
| CS 400 µM | 0.24 (515%) | 0.53 (492%) | n/a | 0.08 (440%) |
| CS 800 µM | 0.25 (492%) | 0.63 (414%) | n/a | 0.08 (451%) |

Ratio 1:X = Target to Effector (PBMC freshly isolated from whole blood)
Donors are homozygous high affinity (High), homozygous low affinity (Low), or Heterozygous for CD16 allele.

Example 11

Effect of Castanospermine at Varying Concentrations on CHO-K1 TRU-016 Protein Production Further experiments were performed to determine the effect of castanospermine concentration on cell viability, density and specific protein production of TRU-016 in, an alternate cell line (CHO-K1) producing TRU-016.

Prior to initiation of the experiments, CHO-K1 cells transfected with TRU-016 (CAS029f053) were grown in vented shake flasks in CD-CHO chemically-defined media (GIBCO- Invitrogen) supplemented with 25 uM methionine sulfoximine (MSX) at 37° C. and 5% carbon dioxide in a humidified incubator. Shaker speed was set at 125 RPM. A 400 mM stock concentration of castanospermine (Alexis Biochemicals) was prepared by dilution of the CS in sterile, distilled/deionized water (MediaTech) followed by filtration through a 13 mm Acrodisc® with a 0.2 μm HT Tuffryn membrane (Pall Corporation). Stock solution was aliquoted into sterile, O-ringed, 0.5 mL microcentrifuge tubes (Fisherbrand, Fisher Scientific) and frozen at −20° C. Approximately 1 hour prior to initiation of experiments, needed aliquots were thawed at room temperature and the contents of each vial mixed well by vortexing.

For the experiment, cells in log phase growth were seeded in the above medium into a volume of 60 mL in 250 mL shaker flasks at a density of 220,000 cells/mL and CS added at the concentration to be tested. Final CS concentrations of 800 μM, 400 μM, 200 μM, 100 μM, 50 μM, 25 μM and 0 μM were each tested in duplicate flasks. All shake flasks were incubated on a shaker platform set at 125 RPM at 37° C. and 5% carbon dioxide in a humidified incubator. Cultures were monitored at least every other day for viable cell density and overall cell viability.

Cultures were harvested on day 10 when overall cell viability was 49-62%. Cells and cellular debris were removed by centrifugation in a Sorvall Super T21 at 3000 rpm for 20 minutes after which the supernatant was sterile filtered through a Millipore Steriflip unit with a 0.22 μm Millipore Express Plus membrane and stored at 4° C. until purified.

Inclusion of castanospermine in the cultures in the final concentration range of 25-800 μM did not appear to significantly affect, positively or negatively, overall cell viability or growth as indicated by each test sample's integral cell area (ICA) compared to that of the control samples (Table 4). Interestingly, the presence of castanospermine had only a very weak suppressive effect on the production of TRU-016 with no more than a 7.5% decrease relative to control noted (Table 4), even at the highest concentration of 800 μM. In fact, the maximal suppressive effect of CS on TRU-016 production was reached at 200 μM and remained essentially the same at higher concentrations of CS. Average specific productivity of the cells at each concentration of CS was essentially the same and very similar to that observed with the control cultures (Table 4) suggesting that CS had no significant effect on this property.

TABLE 4

| Flask # | Test Condition | Viability at Harvest (%) | Average TRU-016 Produced (μg/mL) ± SD | Average TRU-016 Produced as a % of Control ± SD | Average ICA ($10^6$ cells * days/mL) ± $SD^a$ | Average Specific Productivity (pg/cell/day) ± $SD^b$ |
|---|---|---|---|---|---|---|
| 275 | CS - 800 μM | 58.1 | 401.14 ± 4.1 | 92.5 ± 1.0 | 37.6 ± 1.0 | 10.68 ± 0.40 |
| 276 | CS - 800 μM | 59.7 | | | | |
| 277 | CS - 400 μM | 56.1 | 401.22 ± 13.3 | 92.6 ± 3.1 | 37.6 ± 0.3 | 10.68 ± 0.28 |
| 278 | CS - 400 μM | 62.4 | | | | |
| 279 | CS - 200 μM | 61.8 | 401.93 ± 5.0 | 92.7 ± 1.2 | 40.1 ± 2.3 | 10.04 ± 0.69 |
| 280 | CS - 200 μM | 56.4 | | | | |
| 281 | CS - 100 μM | 61.2 | 408.60 ± 6.9 | 94.3 ± 1.6 | 39.0 ± 0.4 | 10.48 ± 0.07 |
| 282 | CS - 100 μM | 55.1 | | | | |
| 283 | CS - 50 μM | 49.4 | 422.84 ± 27.8 | 97.5 ± 6.4 | 41.6 ± 0.9 | 10.18 ± 0.45 |
| 284 | CS - 50 μM | 61.3 | | | | |
| 285 | CS - 25 μM | 57.7 | 419.36 ± 11.1 | 96.7 ± 2.6 | 40.8 ± 0.4 | 10.29 ± 0.18 |
| 286 | CS - 25 μM | 53.0 | | | | |
| 289 | CS - 0 μM | 56.7 | 433.50 ± 10.2 | 100.0 ± 2.4 | 40.4 ± 0.0 | 10.73 ± 0.24 |
| 290 | CS - 0 μM | 57.3 | | | | |

$^a$Integral Cell Area (ICA) = (($VCC_n$ + $VCC_{n+1}$)/2) × ($t_{n+1}$ − $t_n$)
where
$VCC_n$ = viable cell density at time n and $VCC_{n+1}$ = viable cell density at time n + 1.
Units = $10^6$ cells * days/mL
$^b$Specific Productivity = total amount produced (ug/mL)/ICA. Units = pg/cell/day Example 12

Assay for Simultaneous Binding of CHO-K1 Produced TRU-016 and TRU-016 Glycovariants to CD37 and FcγRIIIa (CD16)

An experiment was performed to determine the effect of castanospermine modification of the N-linked oligosaccharide on TRU-016 with regard to the functional activity of the molecule as measured by its binding to FcγRIIIa (CD16) and its binding to target antigen CD37. The experiment was performed as detailed in Example 9 with each of the CS treated samples and controls described in Example 11 and the results graphically represented in FIG. 21. As shown in FIG. 21, CS induced a dose-dependent improvement in TRU-016 glycovariant binding to CD16 that became maximal (approximately 7-fold) at CS concentrations of 100 μM or greater.

Figure 22:
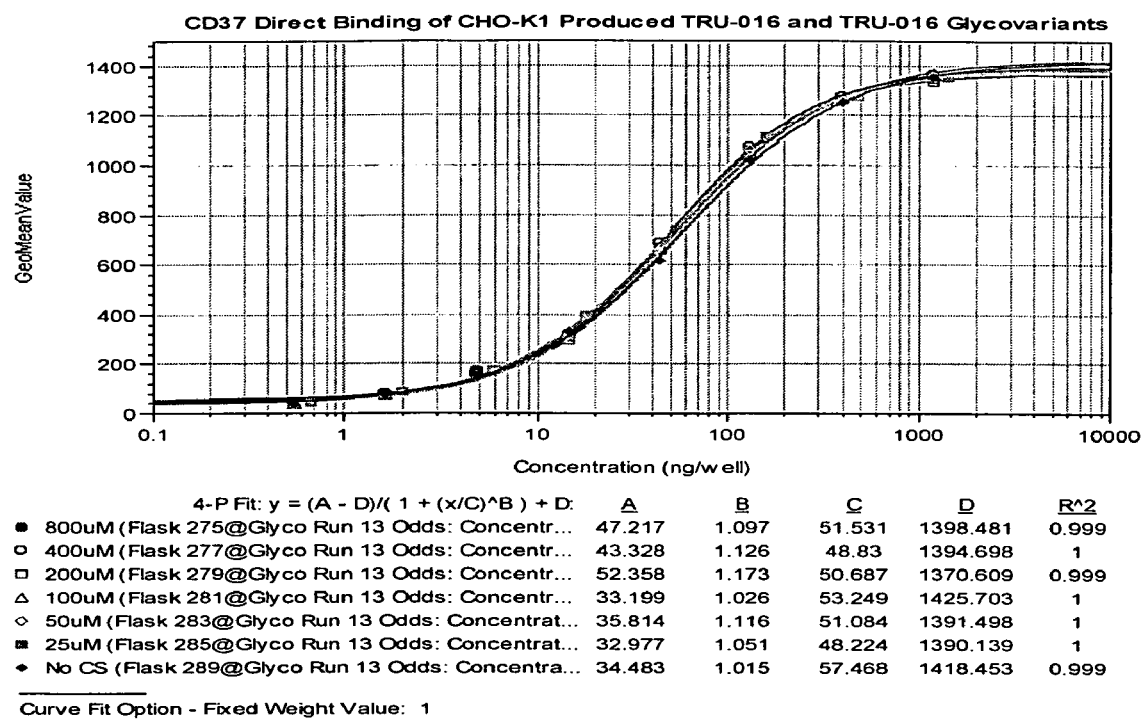
FIG. 22 depicts binding of CHO-K1 produced TRU-016 and CS-generated glycovariants thereof to the CD37 target antigen expressed on Daudi cells. Concentrations of CS utilized for generation of the tested glycovariants are as indicated.

To demonstrate that the enhanced binding of CS induced TRU-016 glycovariant samples to CD16 was not in part due to enhanced binding of the molecules to CD37, each of the different CS treated samples were compared to the control TRU-016 sample in the CD37 binding assay described in Example 9. As shown in FIG. 22, the dose response binding curves of TRU-016 glycovariants to CD37 expressing cells were virtually identical to each other and to that of the control TRU-016 sample, indicating that culture with CS did not alter the binding of TRU-016 to its specific target antigen.

Example 13

Figure 23:
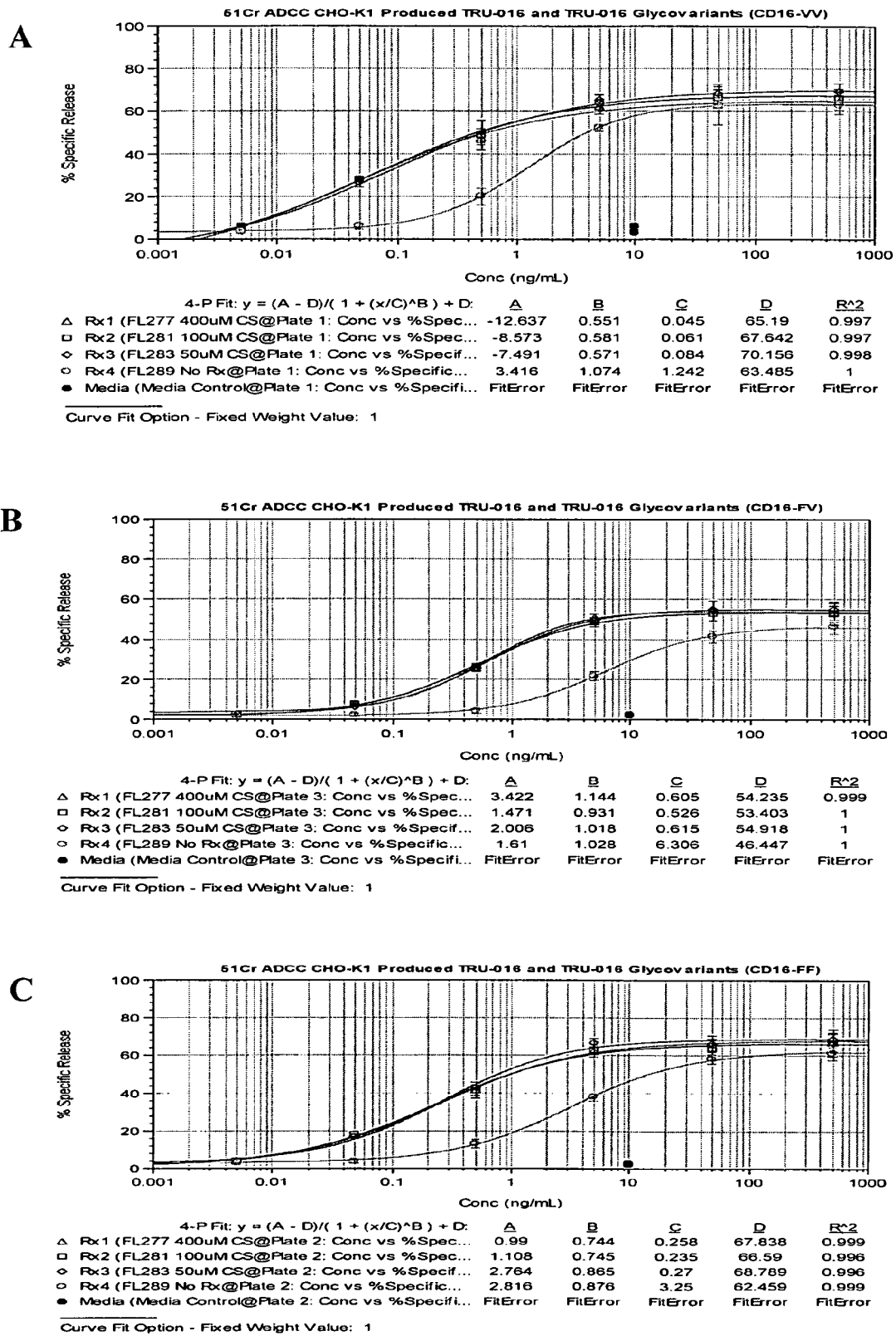
FIG. 23 depicts the results of Antibody Dependent Cellular Cytotoxicity (ADCC) assays performed with CHO-K1 produced TRU-016 and CS-generated glycovariants thereof. Concentrations of CS utilized for generation of the tested glycovariants are as indicated. A-C show the different donor PBL effector cell CD16 genotypes used for each experiment. A, homozygous high (V/V) binder; B, heterozygous (F/V) binder; C, homozygous low (F/F) binder.

Antibody Dependent Cellular Cytotoxicity (ADCC) Assay with CHO-K1 Produced TRU-016 Control and Glycovariant Samples Experiments were performed to determine the effect of increasing concentration of CS in the culture media on the functional activity of resulting TRU-016 as measured by its ability to potentiate ADCC. This assay was carried out as described in Example 10 although in this case, PBL effector cells from each of the three potential CD 16 genotypes [158 Phe/158 Phe (F/F—homozygous low binder), 158 Phe/158 Val (F/V—heterozygous binder) and 158 Val/158 Val (V/V—homozygous high binder)] were tested. As shown in FIG. 23 and Table 5, samples of TRU-016 produced in the presence of 400 µM, 100 µM and 50 µM CS were essentially equally active in enhancing ADCC compared to the untreated control. Furthermore, this observation was consistent regardless of the genotype of the PBL effector cell donor. The fold improvement in ADCC capacity, as determined by $EC_{50}$ comparison of the glycovariant samples versus control, appeared to be greatest in the case of the homozygous high binder (V/V) donor (maximum of 27.6-fold) compared to the heterozygous (F/V) (maximum 12-fold) and homozygous low binder (F/F) (maximum 13.8-fold) donors. In addition, with all three PBL donor types, there was observed a slightly higher level of target cell cytotoxity (2-8%) with the TRU-016 glycovariant molecules as compared to TRU-016 cultured in the absence of CS. This increased level of target cell cytotoxicity was most notable with the heterozygous donor's effector cells.

that there was no methotrexate present. Starting culture volume for each bioreactor was 1700 mLs with a starting density of $3.5 \times 10^5$ cells/mL. A total of eight bioreactors were run in pairs with CS at 0 µM, 300 µM, 350 µM and 400 µM final concentration (one of the 400 µM CS bioreactors was lost to contamination on day 2 of culture). Castanospermine was added at the initiation of culture in the bioreactors with no further addition during the culture period. Other culture conditions included a temperature set point of 37° C., pH set point of 6.9 and dissolved $O_2$ set point of 50%. Bioreactors were run in a fed-batch mode with L-glutamine and glucose added on an as needed basis. Soy hydrolysate (CHO Feed Bioreactor Supplement—C1615—Sigma) was added at 1% of starting culture volume on days 2, 4 and 6. Bioreactors were sampled daily for viable cell density, percent viable cells, media chemistries and osmolality. All cultures were harvested on day 8 when overall cell viability ranged from 39-50%.

Cell growth and viability in the bioreactors was quite comparable as shown for integral cell area (ICA) of the cultures in Table 6 and the fact that they were all harvested at the same time. Production of TRU-016, however, was somewhat inhib-

TABLE 5

| CS Treatment | V/V (high) Donor $EC_{50}$ (ng/mL) | V/V (high) Donor Fold Improvement | F/V (low/high) Donor $EC_{50}$ (ng/mL) | F/V (low/high) Donor Fold Improvement | F/F (low) Donor $EC_{50}$ (ng/mL) | F/F (low) Donor Fold Improvement |
|---|---|---|---|---|---|---|
| 400 µM | 0.05 | 27.6 | 0.61 | 10.4 | 0.26 | 12.6 |
| 100 µM | 0.06 | 20.4 | 0.53 | 12.0 | 0.24 | 13.8 |
| 50 µM | 0.08 | 14.8 | 0.62 | 10.3 | 0.27 | 12.0 |
| None | 1.24 | 1.0 | 6.31 | 1.0 | 3.25 | 1.0 |

Example 14

Effect of Castanospermine at Varying Concentrations on Protein Production in Bioreactors Prior to growth in bioreactors, DG44 CHO cells transfected with TRU-016 were grown in the absence of castanospermine in vented shake flasks as described in Example 8.

For the bioreactor run, 3 L Applikon bioreactors were used. Growth media for cells was as described in Example 8 except ited in all bioreactors containing CS in the culture medium as compared to the control, no CS, bioreactors (Table 7). Suppression of TRU-016 production ranged from 24.9-32% of the non-treated control bioreactors, somewhat less than the 35-40% that might have been predicted from shake flask experiments. As the ICAs of these bioreactors were quite similar, the primary explanation for loss of TRU-016 production may be a decreased specific productivity of the cell line when cultured in the presence of castanospermine (Table 6) as was seen in shake flask experiments.

TABLE 6

| Bioreactor | CS Concentration | Viability at Harvest (%) | TRU-016 Produced (µg/mL) | TRU-016 Produced as a % of Control[a] | ICA ($10^6$ cells * days/mL)[b] | Specific Productivity (pg/cell/day)[c] |
|---|---|---|---|---|---|---|
| R093 | CS - 0 µM | 41.0 | 434.1 | 101.5 | 50.0 | 8.69 |
| R094 | CS - 0 µM | 48.2 | 421.3 | 98.5 | 47.0 | 8.97 |
| R097 | CS - 300 µM | 42.4 | 321.3 | 75.1 | 46.2 | 6.96 |
| R098 | CS - 300 µM | 48.8 | 291.0 | 68.0 | 47.5 | 6.12 |
| R095 | CS - 350 µM | 39.0 | 314.7 | 73.6 | 46.6 | 6.75 |
| R096 | CS - 350 µM | 41.6 | 318.1 | 74.4 | 45.5 | 7.00 |
| R099 | CS - 400 µM | 50.4 | 311.0 | 72.7 | 47.9 | 6.49 |

[a] Based on an average (427.7 ug/mL) of TRU-016 produced in R093 and R094
[b] Integral Cell Area (ICA) = $((VCC_n + VCC_{n+1})/2) \times (t_{n+1} - t_n)$ where $VCC_n$ = viable cell density at time n and $VCC_{n+1}$ = viable cell density at time n + 1. Units = $10^6$ cells * days/mL
[c] Specific Productivity = total amount produced (ug/mL)/ICA. Units = pg/cell/day

Example 15

Assay for Simultaneous Binding of DG44 CHO Produced TRU-016 and TRU-016 Glycovariants to CD37 and FcγRIIIa (CD16)—Bioreactor Generated TRU-016

TRU-016 control and glycovariant proteins were purified from the supernatants of all bioreactors described in Example 14 and evaluated as described in Example 9 for their ability to simultaneously bind to the specific target antigen CD37 and to FcγRIIIa to determine what effect production of TRU-016 in the presence of varying concentrations of castanospermine had on these aspects of TRU-016 functional activity.

As shown in FIG. 24, TRU-016 glycovariants purified from bioreactors containing CS supplemented media at all three CS concentrations stated, displayed nearly identical binding curves over the concentration range tested and that all these samples demonstrated significantly enhanced binding, at least 4-5 fold, compared to the samples from the control, no CS reactors.

Example 16

Antibody Dependent Cellular Cytotoxicity (ADCC) Assay—Bioreactor Generated DG44 CHO Produced TRU-016 and TRU-016 Glycovariants Experiments were performed to determine the effect of increasing concentration of castanospermine in the culture media of DG44 CHO produced TRU-016 on the functional activity of resulting TRU-016 as measured by its ability to potentiate ADCC.

In addition to purification of TRU-016 from all bioreactors described in Example 14 via the abbreviated protein A scheme as detailed in Example 1 (termed PA samples), TRU-016 and TRU-016 glycovariant was purified from bioreactors R094 (no CS) and R099 (400 µM CS), respectively. This method included a 2 column process involving Protein A capture followed by a viral inactivation step at low pH and then a ceramic hydroxyapatite (CHT) polishing step. The samples from this purification method are referred to as CHT samples.

Figure 25:
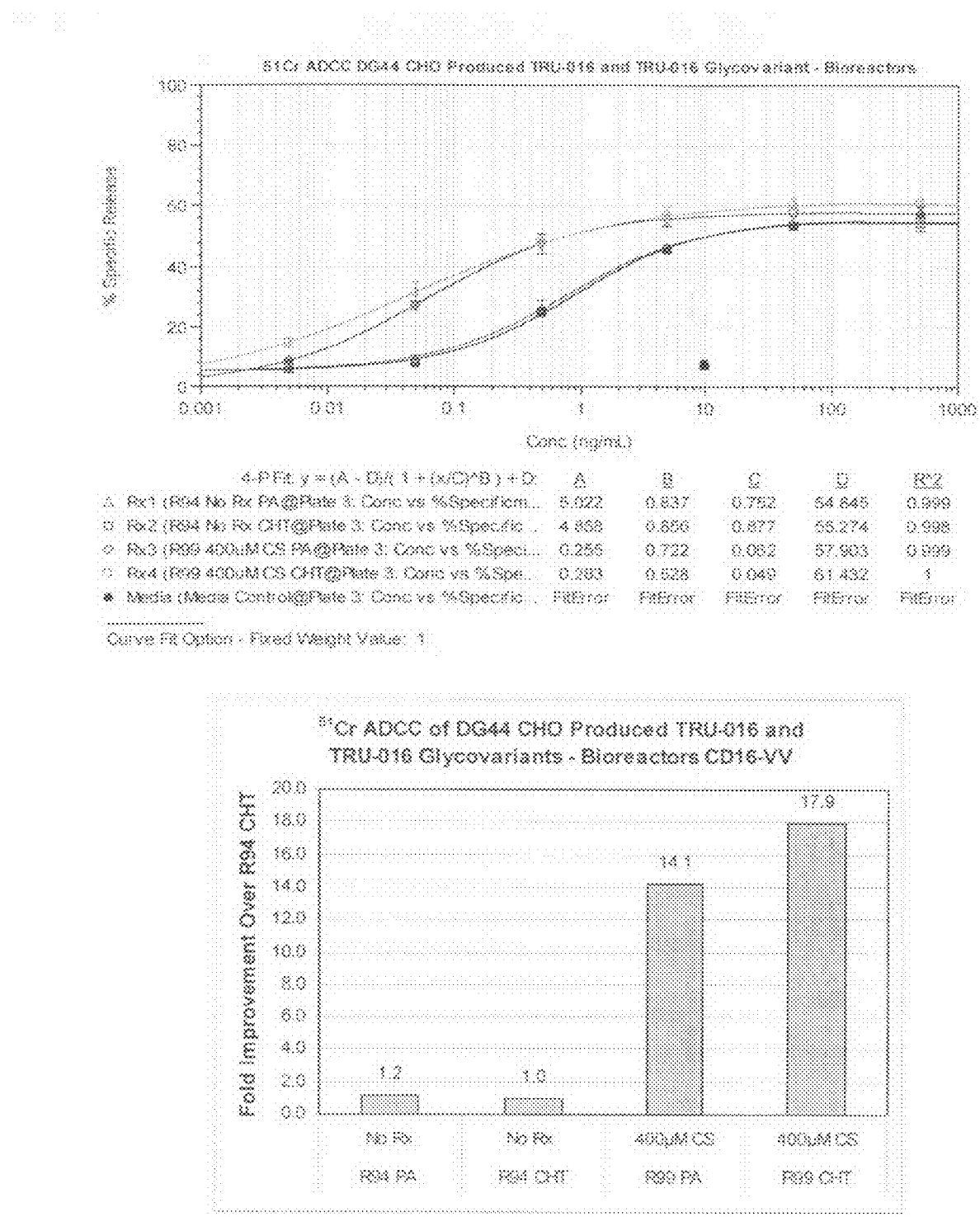
FIG. 25 depicts an Antibody Dependent Cellular Cytotoxicity (ADCC) assay performed with DG44 CHO produced TRU-016 and CS-generated glycovariants thereof. Concentrations of CS utilized for generation of the tested glycovariants are as indicated. These samples represented PA and CHT samples purified from bioreactor runs. Results are shown as raw data curves (A) as well as relative fold-improvement compared to the 0 µM CS (control) TRU-016 CHT sample (B).

Comparison of the two PA and CHT purified preparations from the 0 and 400 µM CS containing bioreactors for their ability to potentiate ADCC assay as described in Example 10 showed that the method of purification made little difference in how the respective samples performed in the assay (FIG. 25) and that inclusion of 400 µM CS in the culture media for DG44 CHO produced TRU-016 yielded a TRU-016 glycovariant that was 12-fold (PA sample) to 18-fold (CHT sample) more potent for ADCC compared to like-purified TRU-016 produced in the absence of CS.

Example 17

Analytical Characterization of TRU-016 Control and Glycovariants Using Liquid Chromatography Coupled to Mass Spectrometry (LCMS) Whole Mass Analysis LCMS analysis was used to confirm the peptide mass and to monitor changes in glycan distribution of TRU-016 immunoglycoprotein generated in the absence (TRU-016) and presence (TRU-016 glycovariant) of varying concentrations of CS. TRU-016 and glycovariants thereof exist as a dimer under non-reducing conditions. Therefore, to simplify the analysis of the heterogeneous mixture of glycoforms, analysis was performed on the reduced, monomeric species. Prior to analysis, the molecule was reduced with 20 mM DTT in 4.8M guanidine. Twenty pmol of monomeric protein was then injected onto a POROS R1 10 µm column and eluted with acetonitrile into an ESI-TOF (Agilent) mass spectrometer detector.

Deglycosylation prior to LCMS analysis by treatment with peptide-N-glycosidase F (PNGaseF) was used to confirm the parent peptide species. The resulting mass spectra were then deconvoluted and the glycan species identified by subtraction of the protein mass. Resulting masses were analyzed using GlycoMod to correlate to known glycoforms, e.g., the observed mass of 53630.7 Daltons (Da) corresponds to the theoretical mass of the native peptide (~52414 Da) plus that of the known glycan structure $Hex_2+(Man)_3(GlcNAc)_2$ (~1216 Da), to within 0.2 Da, or 4 PPM.

The relative abundance of individual glycopeptide species was then estimated by comparing intensities of the deconvoluted peaks of each species identified. The CS-dependent shift in glycoforms was then monitored by comparing the relative abundance of these deconvoluted mass species as a function of CS concentration.

This type of analysis was performed on purified TRU-016 control and glycovariants produced by DG44 CHO cells as well as CHO-K1 cells and the data are summarized in Tables 7 and 8, respectively. Based on this analysis, the observed mass species of the TRU-016 control produced in both CHO cell lines were consistent with the expected amino acid sequence with a typical, heterogeneous mammalian glycosylation pattern. The observed glycoforms were dominated by two glycans, $(Hex)_1(HexNAc)_2(Deoxyhexose)_1+(Man)_3(GlcNAc)_2$ and $(HexNAc)_2(Deoxyhexose)_1+(Man)_3(GlcNAc)_2$, which correlate to the G1F and G0F N-linked glycans, respectively. Non-fucosylated, oligomannose glycoforms represent only a small proportion (DG44 CHO produced, Table 7 or CHO-K1 produced, Table 8) of the observed glycans.

Upon production in culture media containing castanospermine, the observed distribution of glycan species on resulting TRU-016 glycovariants changed in a CS dose-dependent manner to predominantly high-hexose type glycoforms dominated by a $(Hex_7)+(Man)_3(GlcNAc)_2$ species. Thus, with increasing concentration of CS, the proportion of complex, fucosylated glycoforms decreased with a concomitant increase in the proportion of high-hexose glycans.

TABLE 7

| Glycoform Composition | Glycoform Type | Relative Proportion of Glycoform Type | | | | |
|---|---|---|---|---|---|---|
| | | None Control | 200 µM CS | 300 µM CS | 400 µM CS | 500 µM CS |
| Non-Glycosylated | Ø | 5.9 | 9.0 | 9.1 | 9.0 | 7.7 |
| $(Hex)_2(HexNAc)_2(DeoxyHex)_1 + (Man)_3(GlcNAc)_2$ G2F | Complex | 3.5 | —[a] | — | — | — |
| $(Hex)_1(HexNAc)_2(DeoxyHex)_1 + (Man)_3(GlcNAc)_2$ G1F | Complex | 30.9 | 8.1 | 6.0 | 3.4 | 3.7 |
| $(HexNAc)_2(DeoxyHex)_1 + (Man)_3(GlcNAc)_2$ G0F | Complex | 41.4 | 17.8 | 6.3 | 3.3 | 3.9 |
| $(Hex)_2 + (Man)_3(GlcNAc)_2$ | High hexose | 3.2 | 0.6 | — | — | — |
| $(Hex)_3 + (Man)_3(GlcNAc)_2$ | High hexose | 4.3 | — | — | — | — |
| $(Hex)_4 + (Man)_3(GlcNAc)_2$ | High hexose | 4.4 | — | — | — | — |
| $(Hex)_5 + (Man)_3(GlcNAc)_2$ | High hexose | 5.0 | 15.9 | 14.5 | 12.5 | 10.7 |
| $(Hex)_6 + (Man)_3(GlcNAc)_2$ | High hexose | 1.5 | — | — | — | — |
| $(Hex)_7 + (Man)_3(GlcNAc)_2$ | High hexose | — | 46.0 | 57.9 | 65.7 | 68.5 |
| $(Hex)_8 + (Man)_3(GlcNAc)_2$ | High hexose | — | 1.1 | 4.2 | 4.6 | 4.2 |
| $(Hex)_9 + (Man)_3(GlcNAc)_2$ | High hexose | — | 1.6 | 1.9 | 1.6 | 1.3 |

[a]Not detected

TABLE 8

| Glycoform Composition | Glycoform Type | Relative Proportion of Glycoform Type[a] | | | | | | |
|---|---|---|---|---|---|---|---|---|
| | | None Control | 25 µM CS | 50 µM CS | 100 µM CS | 200 µM CS | 400 µM CS | 800 µM CS |
| Non-Glycosylated | Ø | 0.8 | —[b] | 0.8 | — | 1.3 | 0.9 | 1.0 |
| $(Hex)_1(HexNAc)_2(DeoxyHex)_1 + (Man)_3(GlcNAc)_2$ G1F | Complex | 17.1 | 11.7 | 7.4 | 4.0 | 0.9 | — | — |
| $(HexNAc)_2(DeoxyHex)_1 + (Man)_3(GlcNAc)_2$ G0F | Complex | 75.9 | 53.3 | 28.5 | 17.1 | 5.6 | 3.0 | 1.7 |
| $(HexNAc)_2 + (Man)_3(GlcNAc)_2$ G0 | Complex | 2.9 | 1.7 | — | — | — | — | — |
| $(Hex)_5 + (Man)_3(GlcNAc)_2$ | High hexose | — | 13.3 | 16.3 | 13.3 | 8.5 | 5.2 | 5.3 |
| $(Hex)_7 + (Man)_3(GlcNAc)_2$ | High hexose | — | 19.8 | 46.8 | 63.2 | 81.9 | 87.7 | 87.8 |

[a]Average of results from duplicate cultures
[b]Not detected

Example 18

LCMS Tryptic Digest Glycoprofiling of TRU-016/CS-Generated Glycovariants

The purpose of this study was to determine semi-quantitative glycoprofiles for the glycopeptides in control and glycovariant lots of TRU-016. This study identifies the single peptide of TRU-016 which contains carbohydrate, shows the consistency of that glycosylated peptide between control and glycovariant products and illustrates the shift in glycoform that is associated with that single glycopeptide (containing the N-linked glycosylation site). LCMS of a tryptic digest was used to identify the N-linked glycosylation site and attached glycoforms, as a function of CS concentration in cell culture, as described below:

Samples analyzed:
TRU-016 control
Glycovariant TRU-016 200 µM CS
Glycovariant TRU-016 600 µM CS Protein samples were reduced using a 6 M Guanidine HCl, 0.002 M EDTA, 0.02 M Tris denaturing solution, pH 8.33. Five microliters of 1M DTT was added to make a final concentration of 5 mM and sample incubated at 37° C. for one hour.

Following reduction, sample was alkylated with 10 mM iodoacetamide. The sample was incubated for one hour while rocking at ambient temperature, transferred into a dialysis cassette and dialyzed overnight against 50 mM ammonium bicarbonate, pH 8.28. The samples were removed from the dialysis buffer and divided into 2 equal aliquots at 62.5 µg each. Reduced and alkylated protein was stored at −20° C. until needed.

One vial of each sample was removed and thawed at room temperature. To each vial, 1:12.5, w:w of trypsin at 0.5 mg/ml was added. Samples were incubated at 37° C. for 18 hours. The samples were transferred to HPLC vials and placed in the autosampler.

Mass Spectrometry data was collected on a Q-TOF Ultima mass spectrometer (Micromass/Waters) using electrospray ionization (ESI) in positive ion mode. Data was acquired from m/z 200-1950 in MS mode. Prior to analysis, the mass spectrometer was calibrated using a 5th order fit on fragment ions of Glu-Fibrinopeptide covering a range from m/z 175 to 1285.

The results of the analysis show that Asn333 (corresponds to Asn297 in Kabat numbering) is the only potential site of N-linked glycosylation in TRU-016. Detailed analysis of all observed mass species in the tryptic digest generated no evidence of O-linked glycosylation.

Tryptic map chromatograms for the test articles are shown in FIG. 26. The chromatograms were extracted for ions between m/z 600-1800 (the m/z range for the known N-linked tryptic glycopeptide). All ions found in this range were examined more closely to determine if these masses were potentially glycopeptides. The known mass of the peptide that contains Asn333 was subtracted from the observed masses and the resulting masses then analyzed using GlycoMod to correlate to known glycoform structures.

All observed glycopeptide masses were found to elute within 1 minute of each other. Once a potential candidate was identified, the ion abundance as determined by peak height was compiled to provide relative quantities of glycoforms. This data is summarized below. The sample which results from treatment with 600 µM CS is predominantly modified with high hexose type glycoforms, with the predominant species containing ten hexose units. The 200 µM CS sample was found to contain a distribution of glycoforms intermediate between the 600 µM CS sample and glycovariant control.

Chromatogram and extracted glycopeptide mass chromatograms of TRU-016 tryptic digest: The TRU-016 control consistently exhibits a profile with a glycopeptide mass species at ~30.6 minutes RT. The 600 µM CS-treated glycovariant exhibits a glycopeptide peak fully shifted to 30 minutes, while the 200 µM CS sample exhibits a mixture of peaks that elute between 30 and 30.6 minutes.

The tables below show relative abundance of glycoforms identified in the glycopeptide peaks illustrated above and the corresponding glycoform compositions identified by GlycoMod.

N-linked profile ASN$^{333}$ for TRU-016 control

| Glycoform Composition | Type | Relative abundance |
|---|---|---|
| $(Hex)_1 + (Man)_3(GlcNAc)_2$ | high mannose | 0.6% |
| $(Hex)_2 + (Man)_3(GlcNAc)_2$ | high mannose | 1.6% |
| $(HexNAc)_1(Deoxyhexose)_1 + (Man)_3(GlcNAc)_2$ | hybrid/complex | 0.9% |
| $(Hex)_3 + (Man)_3(GlcNAc)_2$ | high mannose | 2.1% |
| $(Hex)_1(HexNAc)_1(Deoxyhexose)_1 + (Man)_3(GlcNAc)_2$ | hybrid/complex | 0.2% |
| $(HexNAc)_2(Deoxyhexose)_1 + (Man)_3(GlcNAc)_2$ | hybrid/complex | 58.9% |
| $(Hex)_4 + (Man)_3(GlcNAc)_2$ | high mannose | 1.5% |
| $(Hex)_1(HexNAc)_2(Deoxyhexose)_1 + (Man)_3(GlcNAc)_2$ | hybrid/complex | 31.2% |
| $(Hex)_5 + (Man)_3(GlcNAc)_2$ | high mannose | 0.9% |
| $(Hex)_2(HexNAc)_2(Deoxyhexose)_1 + (Man)_3(GlcNAc)_2$ | hybrid/complex | 1.3% |
| $(Hex)_6 + (Man)_3(GlcNAc)_2$ | high mannose | 0.7% |

N-linked profile ASN$^{333}$ for Glycovariant (200 µM CS)

| Glycoform Composition | Type | Relative abundance |
|---|---|---|
| $(Hex)_1 + (Man)_3(GlcNAc)_2$ | high mannose | 0.8% |
| $(Hex)_2 + (Man)_3(GlcNAc)_2$ | high mannose | 2.3% |
| $(HexNAc)_1(Deoxyhexose)_1 + (Man)_3(GlcNAc)_2$ | hybrid/complex | 0.9% |
| $(Hex)_3 + (Man)_3(GlcNAc)_2$ | high mannose | 1.5% |
| $(Hex)_1(HexNAc)_1(Deoxyhexose)_1 + (Man)_3(GlcNAc)_2$ | hybrid/complex | 0.6% |
| $(HexNAc)_2(Deoxyhexose)_1 + (Man)_3(GlcNAc)_2$ | hybrid/complex | 36.0% |
| $(Hex)_4 + (Man)_3(GlcNAc)_2$ | high mannose | 2.4% |
| $(Hex)_1(HexNAc)_2(Deoxyhexose)_1 + (Man)_3(GlcNAc)_2$ | hybrid/complex | 24.9% |
| $(Hex)_5 + (Man)_3(GlcNAc)_2$ | high mannose | 10.9% |
| $(Hex)_2(HexNAc)_2(Deoxyhexose)_1 + (Man)_3(GlcNAc)_2$ | hybrid/complex | 3.2% |
| $(Hex)_6 + (Man)_3(GlcNAc)_2$ | high mannose | 1.1% |
| $(Hex)_7 + (Man)_3(GlcNAc)_2$ | high mannose | 14.7% |
| $(Hex)_8 + (Man)_3(GlcNAc)_2$ | high mannose | 0.6% |

N-linked profile ASN$^{333}$ for Glycovariant (600 µM CS)

| Glycoform Composition | Type | Relative abundance |
|---|---|---|
| $(Hex)_3 + (Man)_3(GlcNAc)_2$ | high mannose | 0.1% |
| $(HexNAc)_1(Deoxyhexose)_1 + (Man)_3(GlcNAc)_2$ | hybrid/complex | 0.9% |
| $(Hex)_4 + (Man)_3(GlcNAc)_2$ | high mannose | 0.5% |
| $(Hex)_1(HexNAc)_2(Deoxyhexose)_1 + (Man)_3(GlcNAc)_2$ | hybrid/complex | 1.3% |
| $(Hex)_4 + (Man)_3(GlcNAc)_2$ | high mannose | 6.2% |
| $(Hex)_2(HexNAc)_2(Deoxyhexose)_1 + (Man)_3(GlcNAc)_2$ | hybrid/complex | 0.3% |
| $(Hex)_6 + (Man)_3(GlcNAc)_2$ | high mannose | 2.3% |
| $(Hex)_7 + (Man)_3(GlcNAc)_2$ | high mannose | 87.7% |
| $(Hex)_8 + (Man)_3(GlcNAc)_2$ | high mannose | 0.5% |
| $(Hex)_9 + (Man)_3(GlcNAc)_2$ | high mannose | 0.1% |

The above tables illustrate that samples treated with increasing concentrations of castanospermine contain increasing amounts of high hexose, non-fucosylated glycoforms compared to the TRU-016 control. At higher concentrations, the glycan distribution is almost fully shifted to high hexose, non-fucosylated glycoforms, while at lower concentrations of CS a mixture of glycan types is observed, in a dose-dependent fashion.

Example 19

Monosaccharide Analysis of TRU-016 Control and Glycovariants

This procedure was used to determine the monosaccharide content of the N-linked glycoforms displayed on TRU-016 control versus TRU-016 glycovariant immunoglycoproteins. In this method, monosaccharides were released by hydrolysis then derivatized with a fluorescent modifier. Subsequent analysis of the labeled monosaccharides was accomplished using reverse phase chromatography coupled with fluorescence detection. Quantitation of the monosaccharides was accomplished by comparison of test article monosaccharide peak areas to the peak areas obtained from titration of known concentrations of labeled monosaccharide standards. The monosaccharide content of the sample was then compared to the mass of protein hydrolyzed and reported as the mole ratio of each monosaccharide per mole of the monomeric unit of the normally dimeric TRU-016 protein.

Samples analyzed included the TRU-016 control and TRU-016 glycovariant produced in the presence of 400 µM CS.

Monosaccharides were released from the protein by incubating 50 µg of each sample with 20% (v/v) trifluoroacetic acid at 100° C. for 4 hours. Following hydrolysis, the samples were dried down. Released monosaccharides were resuspended in 200 µL of labeling mixture containing 30 mg/mL fluorescent derivative (2-AA, 2-Aminobenzoic Acid), 20 mg/mL sodium cyanoborohydride, approximately 30 mg/mL sodium acetate and 15 mg/mL boric acid in methanol and incubated at 80° C. for 60 minutes. The derivatization reaction was quenched by the addition of 200 µL of mobile phase A [0.2% (v/v) n-butylamine, 0.5% (v/v) phosphoric acid, 1% (v/v) tetrahydrofuran]. A water blank was also hydrolyzed and derivatized to determine method specificity. Samples were then analyzed by reverse phase HPLC coupled with fluorescence detection. The quantity of monosaccharide in each sample was determined by comparison to standard curves.

Figure 27:
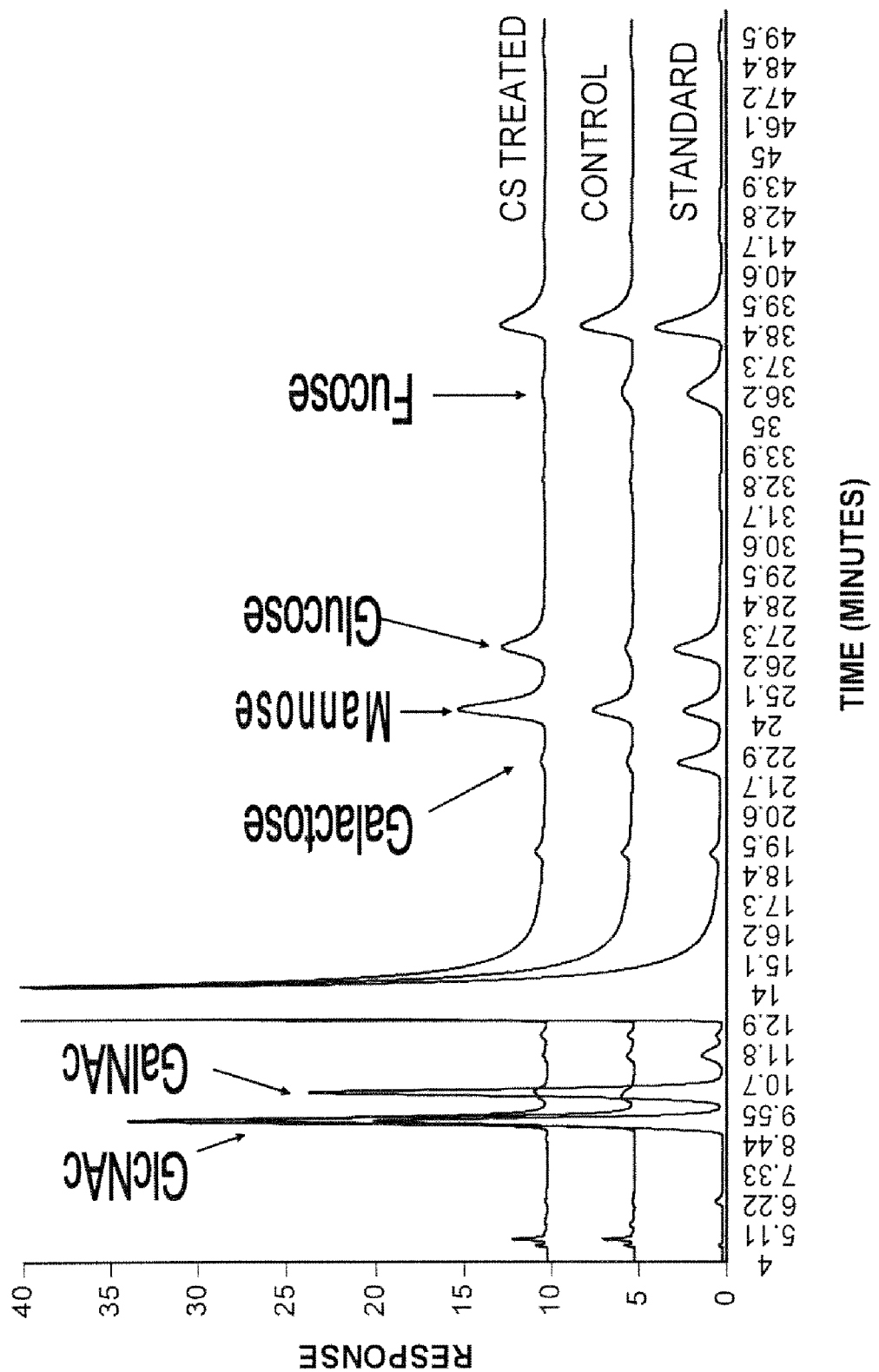
FIG. 27 depicts results from a monosaccharide analysis of TRU-016 and CS-generated glycovariants thereof. The glycovariant treated with 400 µM CS, the control, and the monosaccharide standards are each indicated by arrows.

Representative chromatograms of the monosaccharide standards, TRU-016 control and TRU-016 glycovariant (400 µM CS) are shown in FIG. 27. As seen in the chromatograms, the mannose content of the TRU-016 glycovariant was approximately double that of the TRU-016 control. GlcNAc content of the glycovariant decreased by about half from the TRU-016 control and fucose was absent in the TRU-016 glycovariant sample. In addition, glucose, which was below the limits of quantitation in the TRU-016 control, increased to 2-3 moles per mole of monomeric protein in the TRU-016 glycovariant sample. These results coupled with the preceeding LCMS data are consistent with a shift from complex, predominantly G0F glycosylation on the TRU-016 control to a primarily glucosylated high mannose form on the TRU-016 glycovariant.

It should be noted that TRU-016 glycosylation, as with all glycoproteins, is heterogeneous and there is potential for loss due to the harsh conditions of this assay and resultant low recovery. Thus, these assays tend to underestimate the actual monosaccharide content of a glycoprotein. In addition, all glycan species in the heterogeneous mixture contribute to the total monosaccharide content of a protein sample, so the molar content of individual monosaccharides may not correlate directly to any single glycan species.

Example 20

Oligosaccharide Analysis of TRU-016 Control Versus TRU-016 Glycovariant

The purpose of this study was to characterize the oligosaccharide content of TRU-016 control and glycovariant test articles. In this method, oligosaccharides were first released from denatured protein by enzymatic digestion with PNGase-F. The released oligosaccharides were then derivatized with a fluorescent label and separated by normal phase chromatography coupled with fluorescence detection. Each released glycan species will resolve to produce a characteristic oligosaccharide profile by which changes in glycosylation can be monitored.

Samples were initially reduced in a solution of 2% SDS and 1M beta mercaptoethanol for 5 minutes at 100° C. Enzymatic release of oligosaccharides was accomplished by incubation of samples with 2 µL PNGase-F at 37° C. for 3 hours. Following release, the oligosaccharides were fluorescently labeled using the LudgerTag 2-AA glycan labeling kit (QA-Bio, LLC, Palm Desert, Calif.), following the manufacturer's recommended procedures.

The glycans were purified from the excess labeling reagent using a QA-Bio S Cartridge following the procedures specified by the manufacturer. The labeled oligosaccharides were then separated by normal phase chromatography and monitored by fluorescence detection. For further analysis of individual glycans, a separate analysis of TRU-016 control was performed to collect fractions of the major glycan peaks for subsequent analysis by MALDI-TOF.

Figure 28:
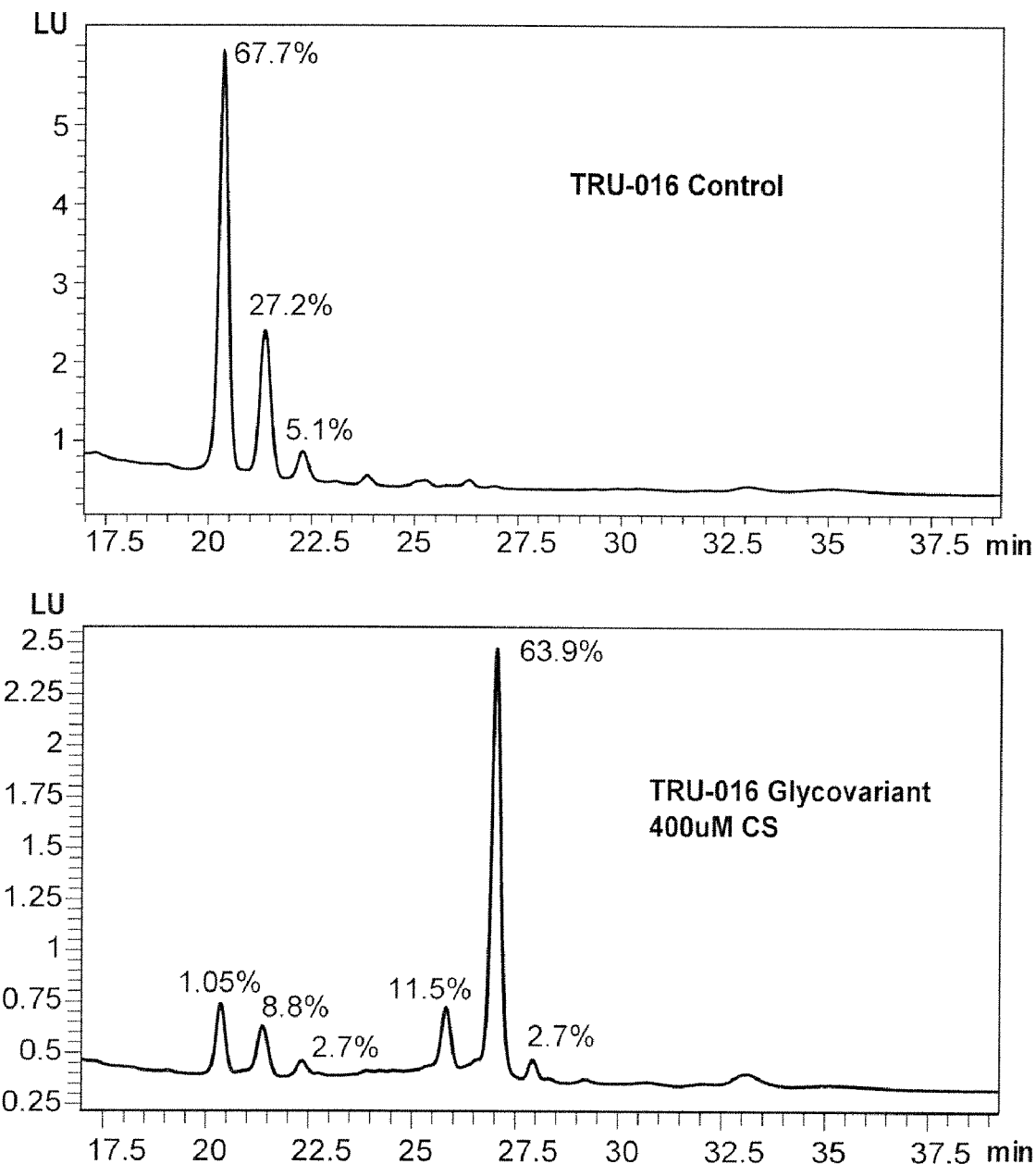
FIG. 28 depicts results from an oligosaccharide analysis of TRU-016 Control and CS-generated glycovariant products. The relative percent (peak area) of the major species is identified above the corresponding peaks.

Oligosaccharide profiles for the TRU-016 control and TRU-016 glycovariant (400 µM CS) are shown in FIG. 28 with relative percent of peak area for the major glycan species indicated. These profiles are consistent with LCMS and monosaccharide analysis data (already described) as well as the known elution profile of oligosaccharide standards. The major species in the control oligosaccharide profile correspond to the G0F, G1F and G2F glycans standards (not shown). Typically, these, fucosylated, complex oligosaccharide standards elute between 18.5 and 23 minutes, while non-fucosylated, high mannose oligosaccharides elute between 24.5 and 30 minutes with the conditions used for this analysis. Thus, the TRU-016 control oligosaccharides exhibit a profile consistent with fucosylated, complex glycans with only a very minor contribution from oligo-mannose glycans. The TRU-016 glycovariant, however, demonstrates a strong shift to high mannose oligosaccharides, with only a minor, residual contribution from fucosylated, complex glycans.

In addition to the analytical comparison of oligosaccharide profiles, a preparative analysis of TRU-016 control was performed and the major glycan species collected for further analysis. The two major glycans of TRU-016 were identified by this method:

Most abundant species (~20 minutes RT): $(HexNAc)_4(Hex)_3(DeoxyHex)_1$

Secondary species (~21.5 minutes RT): $(HexNAc)_4(Hex)_4(DeoxyHex)$,

These structures correspond to the G0F and G1F glycoforms.

The results of the oligosaccharide analysis of TRU-016 glycovariant samples are consistent with the LCMS and monosaccharide analyses and with a shift from complex, fucosylated glycoforms to non-fucosylated, glucosylated, high mannose forms.

Analytical Summary

Taken together, the LCMS, monosaccharide and oligosaccharide analyses demonstrate that production of TRU-016 in the presence of a sufficient amount of castanospermine alters the N-linked oligosaccharide content from primarily fucosylated, complex type glycans (G0F and G1F) to a family of non-fucosylated, glucosylated, high hexose glycans dominated by a $(Hex)_7+(Man)_3(GlcNAc)_2$ glycoform. Monosaccharide analysis of the glycovariant demonstrates the presence of 2 or more moles of glucose per mole of monomeric protein. Because there is only one N-linked glycosylation site per monomeric unit of TRU-016, this data indicates that the composition of the major N-linked glycan species, generated by production of TRU-016 in the presence of castanospermine, is $(Glc)_3(Man)_4+(Man)_3(GlcNAc)_2$ and/or $(Glc)_2(Man)_5+(Man)_3(GlcNAc)_2$.

Monitoring the CD16 binding/ADCC activity of the glycovariant as a function of CS concentration in the cell culture allows identification of the CS concentration at which these functional activities become maximal. In this same manner, LCMS analysis of glycoform composition as a function of CS concentration allows monitoring of the shift in composition as it relates to CS concentration and, hence, to CD16 binding/ADCC enhancement. For example, production of TRU-016 by CHO-K1 cells in the presence of 50 μM CS (Table 9) yields a glycovariant product that has maximal ADCC activity while the glycan composition has shifted to ~50% $(Hex)_7+(Man)_3(GlcNAc)_2$. This indicates that a complete shift to a single glycoform is not necessary to achieve the observed increase in activity. This data further suggests that the glycoforms attached to the two N-linked sites in dimeric SMIP molecules need not be identical or need not both consist of the non-fucosylated, glucosylated, high mannose form to achieve optimal CD16 binding or ADCC. Modification of only one of the SMIP N-linked oligosaccharides to the non-fucosylated, glucosylated, high mannose type may be sufficient to maximize the CD16 binding and ADCC properties of the SMIP.

While the compositions and methods of this invention have been described in terms of the above-described exemplary embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The references cited herein throughout, to the extent that they provide exemplary details supplementary to those set forth herein, are all specifically incorporated herein by reference.

What is claimed is:

1. A composition comprising recombinant immunoglycoprotein molecules comprising a N-linked glycosylation site for linkage of oligosaccharide, wherein said immunoglycoprotein molecules have a glucose content characterized by a ratio of glucose molecules per said N-linked glycosylation site of at least 1.5.

2. The composition of claim 1, wherein said ratio is at least 2.

3. The composition of claim 1, wherein said ratio is at least 2.5.

4. The composition of any of claims 1, 2, and 3 wherein said recombinant immunoglycoprotein molecules in a reduced state each comprise a single N-linked glycosylation site.

5. A composition of recombinant immunoglycoprotein molecules comprising a N-linked glycosylation site for linkage of oligosaccharide, wherein at least 60% of said N-linked oligosaccharides of said N-linked glycosylation site have a glucose content from two to three glucose molecules.

6. A composition of recombinant immunoglycoprotein molecules comprising a N-linked glycosylation site for linkage of oligosaccharide, wherein at least 60% of said N-linked oligosaccharides of said N-linked glycosylation site have a glucose content of three glucose molecules.

7. A composition of any of claims 1, 2, 3, 5, and 6 wherein said immunoglycoprotein molecules exhibit at least 5-fold higher ADCC compared to control immunoglycoprotein molecules of the same encoded amino acid sequence produced in CHO-K1 cells in the absence of carbohydrate modifier.

8. A composition of any of claims 1, 2, 3, 5, and 6 wherein at least 60% of the N-linked oligosaccharides of said N-linked glycosylation site contain no fucose.

9. A composition comprising recombinant immunoglycoprotein molecules comprising a N-linked glycosylation site for linkage of oligosaccharide wherein said molecules exhibit the following characteristics:
   a) said immunoglycoprotein molecules have a glucose content characterized by a ratio of glucose molecules per said N-linked glycosylation site of at least 1.5;
   b) at least 60% of said N-linked oligosaccharides of said N-linked glycosylation site have a glucose content from two to three glucose molecules;
   c) at least 5-fold higher ADCC compared to control immunoglycoprotein molecules of the same encoded amino acid sequence produced in CHO-K1 cells in the absence of castanospermine; and
   d) at least 60% of the N-linked oligosaccharides of said N-linked glycosylation site contain no fucose.

10. A composition of any of claims 1, 2, 5, 6, and 9 and a sterile pharmaceutically acceptable carrier or diluent.

11. The composition of claim 10 which is sterile.

12. A composition of any of claims 1, 2, 5, 6, and 9 comprising at least 100 liters of culture medium.

13. A composition of any of claims 1, 2, 5, 6, and 9 comprising at least 100 g of immunoglycoprotein molecules and a pharmaceutically acceptable carrier or diluent.

14. The composition of claim 10 wherein the recombinant immunoglycoprotein molecules are bispecific in antigen-binding.

15. The composition of claim 10 wherein the recombinant immunoglycoprotein molecules are trispecific in antigen-binding.

16. The composition of any of claims 1, 2, 5, 6, and 9 wherein the recombinant immunoglycoprotein molecule is a small modular immunopharmaceutical.

17. The composition of claim 16 wherein the small modular immunopharmaceutical comprises amino acids 24-496 of SEQ ID NO: 2.

* * * * *

SEQUENCE LISTING

<160> NUMBER OF SEQ ID NOS: 2

<210> SEQ ID NO 1
<211> LENGTH: 1510
<212> TYPE: DNA
<213> ORGANISM: Artificial sequence
<220> FEATURE:
<223> OTHER INFORMATION: TRU-016 polynucleotide

<400> SEQUENCE: 1

```
aagcttgccg ccatggattt tcaagtgcag attttcagct tcctgctaat cagtgcttca        60
gtcataattg ccagaggagt cgacatccag atgactcagt ctccagcctc cctatctgca       120
tctgtgggag agactgtcac catcacatgt cgaacaagtg aaaatgttta cagttatttg       180
gcttggtatc agcagaaaca gggaaaatct cctcagctcc tggtctcttt tgcaaaaacc       240
ttagcagaag gtgtgccatc aaggttcagt ggcagtggat caggcacaca gttttctctg       300
aagatcagca gcctgcagcc tgaagattct ggaagttatt tctgtcaaca tcattccgat       360
aatccgtgga cgttcggtgg aggcaccgaa ctggagatca aaggtggcgg tggctcgggc       420
ggtggtgggt cgggtggcgg cggatcgtca gcggtccagc tgcagcagtc tggacctgag       480
tcggaaaagc ctggcgcttc agtgaagatt tcctgcaagg cttctggtta ctcattcact       540
ggctacaata tgaactgggt gaagcagaat aatggaaaga gccttgagtg gattggaaat       600
attgatcctt attatggtgg tactacctac aaccggaagt tcaagggcaa ggccacattg       660
actgtagaca aatcctccag cacagcctac atgcagctca agagtctgac atctgaggac       720
tctgcagtct attactgtgc aagatcggtc ggccctatgg actactgggg tcaaggaacc       780
tcagtcaccg tctcttcaga tctggagccc aaatcttctg acaaaactca cacatctcca       840
ccgtgcccag cacctgaact cttgggtgga ccgtcagtct tcctcttccc cccaaaaccc       900
aaggacaccc tcatgatctc ccggacccct gaggtcacat gcgtggtggt ggacgtgagc       960
cacgaagacc ctgaggtcaa gttcaactgg tacgtggacg gcgtggaggt gcataatgcc      1020
aagacaaagc cgcgggagga gcagtacaac agcacgtacc gtgtggtcag cgtcctcacc      1080
gtcctgcacc aggactggct gaatggcaag gagtacaagt gcaaggtctc caacaaagcc      1140
ctcccagccc ccatcgagaa aaccatctcc aaagccaaag gcagccccg agaaccacag      1200 gtgtacaccc tgcccccatc ccgggatgag ctgaccaaga accaggtcag cctgacctgc      1260
```

```
ctggtcaaag gcttctatcc aagcgacatc gccgtggagt gggagagcaa tgggcaaccg    1320
gagaacaact acaagaccac gcctcccgtg ctggactccg acggctcctt cttcctctac    1380
agcaagctca ccgtggacaa gagcaggtgg cagcagggga acgtcttctc atgctccgtg    1440
atgcatgagg ctctgcacaa ccactacacg cagaagagcc tctccctgtc tccgggtaaa    1500
tgagtctaga                                                            1510

<210> SEQ ID NO 2
<211> LENGTH: 496
<212> TYPE: PRT
<213> ORGANISM: Artificial sequence
<220> FEATURE:
<223> OTHER INFORMATION: TRU-016 polypeptide

<400> SEQUENCE: 2
```

Met Asp Phe Gln Val Gln Ile Phe Ser Phe Leu Leu Ile Ser Ala Ser
1               5                   10                  15

Val Ile Ile Ala Arg Gly Val Asp Ile Gln Met Thr Gln Ser Pro Ala
            20                  25                  30

Ser Leu Ser Ala Ser Val Gly Glu Thr Val Thr Ile Thr Cys Arg Thr
        35                  40                  45

Ser Glu Asn Val Tyr Ser Tyr Leu Ala Trp Tyr Gln Gln Lys Gln Gly
    50                  55                  60

Lys Ser Pro Gln Leu Leu Val Ser Phe Ala Lys Thr Leu Ala Glu Gly
65                  70                  75                  80

Val Pro Ser Arg Phe Ser Gly Ser Gly Ser Gly Thr Gln Phe Ser Leu
                85                  90                  95

Lys Ile Ser Ser Leu Gln Pro Glu Asp Ser Gly Ser Tyr Phe Cys Gln
            100                 105                 110

His His Ser Asp Asn Pro Trp Thr Phe Gly Gly Gly Thr Glu Leu Glu
        115                 120                 125

Ile Lys Gly Gly Gly Gly Ser Gly Gly Gly Gly Ser Gly Gly Gly Gly
    130                 135                 140

Ser Ser Ala Val Gln Leu Gln Gln Ser Gly Pro Glu Ser Glu Lys Pro
145                 150                 155                 160

Gly Ala Ser Val Lys Ile Ser Cys Lys Ala Ser Gly Tyr Ser Phe Thr
                165                 170                 175

Gly Tyr Asn Met Asn Trp Val Lys Gln Asn Asn Gly Lys Ser Leu Glu
            180                 185                 190

Trp Ile Gly Asn Ile Asp Pro Tyr Tyr Gly Gly Thr Thr Tyr Asn Arg
        195                 200                 205

Lys Phe Lys Gly Lys Ala Thr Leu Thr Val Asp Lys Ser Ser Ser Thr
    210                 215                 220

Ala Tyr Met Gln Leu Lys Ser Leu Thr Ser Glu Asp Ser Ala Val Tyr
225                 230                 235                 240

Tyr Cys Ala Arg Ser Val Gly Pro Met Asp Tyr Trp Gly Gln Gly Thr
                245                 250                 255

Ser Val Thr Val Ser Ser Asp Leu Glu Pro Lys Ser Ser Asp Lys Thr
            260                 265                 270

His Thr Ser Pro Pro Cys Pro Ala Pro Glu Leu Leu Gly Gly Pro Ser
        275                 280                 285

Val Phe Leu Phe Pro Pro Lys Pro Lys Asp Thr Leu Met Ile Ser Arg
    290                 295                 300

Thr Pro Glu Val Thr Cys Val Val Val Asp Val Ser His Glu Asp Pro

-continued

```
305                 310                 315                 320
Glu Val Lys Phe Asn Trp Tyr Val Asp Gly Val Glu Val His Asn Ala
                325                 330                 335
Lys Thr Lys Pro Arg Glu Glu Gln Tyr Asn Ser Thr Tyr Arg Val Val
                340                 345                 350
Ser Val Leu Thr Val Leu His Gln Asp Trp Leu Asn Gly Lys Glu Tyr
                355                 360                 365
Lys Cys Lys Val Ser Asn Lys Ala Leu Pro Ala Pro Ile Glu Lys Thr
                370                 375                 380
Ile Ser Lys Ala Lys Gly Gln Pro Arg Glu Pro Gln Val Tyr Thr Leu
385                 390                 395                 400
Pro Pro Ser Arg Asp Glu Leu Thr Lys Asn Gln Val Ser Leu Thr Cys
                405                 410                 415
Leu Val Lys Gly Phe Tyr Pro Ser Asp Ile Ala Val Glu Trp Glu Ser
                420                 425                 430
Asn Gly Gln Pro Glu Asn Asn Tyr Lys Thr Thr Pro Pro Val Leu Asp
                435                 440                 445
Ser Asp Gly Ser Phe Phe Leu Tyr Ser Lys Leu Thr Val Asp Lys Ser
                450                 455                 460
Arg Trp Gln Gln Gly Asn Val Phe Ser Cys Ser Val Met His Glu Ala
465                 470                 475                 480
Leu His Asn His Tyr Thr Gln Lys Ser Leu Ser Leu Ser Pro Gly Lys
                485                 490                 495
```